(12) United States Patent
Klessel et al.

(10) Patent No.: US 8,499,635 B2
(45) Date of Patent: *Aug. 6, 2013

(54) TRANSDUCER ARRAY IMAGING SYSTEM

(75) Inventors: Jodi Schwartz Klessel, Blue Bell, PA (US); Kevin S. Randall, Ambler, PA (US); Joseph A. Urbano, Audubon, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/544,350

(22) Filed: Jul. 9, 2012

(65) Prior Publication Data
US 2012/0272738 A1 Nov. 1, 2012

Related U.S. Application Data

(63) Continuation of application No. 11/595,033, filed on Nov. 10, 2006, now Pat. No. 8,220,334.

(51) Int. Cl.
*G01N 29/04* (2006.01)

(52) U.S. Cl.
USPC .......... 73/602; 73/596; 73/611; 310/322

(58) Field of Classification Search
USPC .............. 73/602, 596, 611; 600/437, 443, 600/447, 459
See application file for complete search history.

(56) References Cited

U.S. PATENT DOCUMENTS

| | | | |
|---|---|---|---|
| 4,074,223 A | 2/1978 | Eggleton et al. |
| 4,140,022 A | 2/1979 | Maslak |
| 4,246,792 A | 1/1981 | Matzuk |
| 4,394,642 A | 7/1983 | Currie et al. |
| 4,413,629 A | 11/1983 | Durley, III |
| 4,489,392 A | 12/1984 | Lewis |
| 4,604,697 A | 8/1986 | Luthra et al. |
| 4,853,904 A | 8/1989 | Pesque |
| 5,014,712 A | 5/1991 | O'Donnell |
| 5,229,933 A | 7/1993 | Larson, III |
| 5,247,524 A | 9/1993 | Callon |
| 5,278,757 A | 1/1994 | Hoctor et al. |
| 5,295,485 A | 3/1994 | Shinomura et al. |
| 5,520,187 A | 5/1996 | Snyder |

(Continued)

FOREIGN PATENT DOCUMENTS

EP 0762142 A1 3/1997

OTHER PUBLICATIONS

U.S. Appl. No. 11/595,025, filed Nov. 10, 2006, Randall et al.
U.S. Appl. No. 11/595,027, filed Nov. 10, 2006, Urbano et al.

(Continued)

*Primary Examiner* — J M Saint Surin

(57) ABSTRACT

Embodiments contemplate methods and devices for conducting ultrasound interrogation of a medium. An ultrasound echo wave may be received at a first transducer element of a transducer array in a handheld probe. The ultrasound echo wave may also be received at a second transducer element of the transducer array. The ultrasound echo wave may also be received at a third transducer element of the transducer array. The handheld probe may process into digital data the ultrasound echo wave received at the first transducer element and the ultrasound echo wave received at the second transducer element. The processing may preclude data representative of the ultrasound echo wave received at the third transducer element from being included in the digital data. The processing may include reducing the digital data and the reduced digital data may be transmitted to a location relatively remote from the handheld probe.

30 Claims, 23 Drawing Sheets

U.S. PATENT DOCUMENTS

| | | |
|---|---|---|
| 5,522,077 A | 5/1996 | Cuthbert et al. |
| 5,544,654 A | 8/1996 | Murphy et al. |
| 5,581,036 A | 12/1996 | Chang et al. |
| 5,590,658 A | 1/1997 | Chiang et al. |
| 5,621,345 A | 4/1997 | Lee et al. |
| 5,640,960 A | 6/1997 | Jones et al. |
| 5,685,307 A | 11/1997 | Holland et al. |
| 5,690,114 A | 11/1997 | Chiang et al. |
| 5,709,209 A | 1/1998 | Friemel et al. |
| 5,713,363 A | 2/1998 | Seward et al. |
| 5,722,412 A | 3/1998 | Pflugrath et al. |
| 5,738,099 A | 4/1998 | Chang |
| 5,774,499 A | 6/1998 | Ahn et al. |
| 5,817,024 A | 10/1998 | Ogle et al. |
| 5,825,749 A | 10/1998 | Terayama et al. |
| 5,839,442 A | 11/1998 | Chiang et al. |
| 5,846,205 A | 12/1998 | Curley et al. |
| 5,865,733 A | 2/1999 | Malinouskas et al. |
| 5,893,363 A | 4/1999 | Little et al. |
| 5,921,932 A | 7/1999 | Wright et al. |
| 5,951,479 A | 9/1999 | Holm et al. |
| 5,957,846 A | 9/1999 | Chiang et al. |
| 5,964,709 A | 10/1999 | Chiang et al. |
| 6,029,116 A | 2/2000 | Wright et al. |
| 6,056,693 A | 5/2000 | Haider |
| 6,102,863 A | 8/2000 | Pflugrath et al. |
| 6,113,547 A | 9/2000 | Catallo et al. |
| 6,117,085 A | 9/2000 | Picatti et al. |
| 6,135,961 A | 10/2000 | Pflugrath et al. |
| 6,142,946 A | 11/2000 | Hwang et al. |
| 6,148,224 A | 11/2000 | Jensen |
| 6,174,286 B1 | 1/2001 | Ramamurthy et al. |
| 6,208,636 B1 | 3/2001 | Tawil et al. |
| 6,230,000 B1 | 5/2001 | Tayloe |
| 6,231,510 B1 | 5/2001 | Negrin et al. |
| 6,231,511 B1 | 5/2001 | Bae |
| 6,248,075 B1 | 6/2001 | McGee et al. |
| 6,251,073 B1 | 6/2001 | Imran et al. |
| 6,275,505 B1 | 8/2001 | O'Loughlin et al. |
| 6,364,839 B1 | 4/2002 | Little et al. |
| 6,423,002 B1 | 7/2002 | Hossack |
| 6,436,047 B1 | 8/2002 | Ramamurthy et al. |
| 6,440,072 B1 | 8/2002 | Schuman et al. |
| 6,450,958 B1 | 9/2002 | Linkhart et al. |
| 6,471,651 B1 | 10/2002 | Hwang et al. |
| 6,491,634 B1 | 12/2002 | Leavitt et al. |
| 6,497,664 B1 | 12/2002 | Randall et al. |
| 6,508,763 B1 | 1/2003 | Urbano et al. |
| 6,514,201 B1 | 2/2003 | Greenberg |
| 6,527,719 B1 | 3/2003 | Olsson et al. |
| 6,527,721 B1 | 3/2003 | Wittrock et al. |
| 6,551,246 B1 | 4/2003 | Ustuner et al. |
| 6,569,102 B2 | 5/2003 | Imran et al. |
| 6,584,103 B1 | 6/2003 | Hanaoka et al. |
| 6,679,847 B1 | 1/2004 | Robinson et al. |
| 6,685,645 B1 | 2/2004 | McLaughlin et al. |
| 6,689,063 B1 | 2/2004 | Jensen et al. |
| 6,695,783 B2 | 2/2004 | Henderson et al. |
| 6,725,076 B1 | 4/2004 | Jensen |
| 6,743,175 B2 | 6/2004 | Greenberg |
| 6,780,154 B2 | 8/2004 | Hunt et al. |
| 6,859,659 B1 | 2/2005 | Jensen |
| 6,860,854 B2 | 3/2005 | Robinson |
| 7,022,075 B2 | 4/2006 | Grunwald et al. |
| 7,052,459 B2 | 5/2006 | Washburn et al. |
| 7,207,940 B2 | 4/2007 | Satoh |
| 7,257,158 B1 | 8/2007 | Figueredo et al. |
| 7,431,698 B2 | 10/2008 | Bruestle |
| 2003/0139664 A1 | 7/2003 | Hunt et al. |
| 2004/0068188 A1 | 4/2004 | Robinson |
| 2004/0171935 A1 | 9/2004 | Van Creveld et al. |
| 2004/0181154 A1 | 9/2004 | Peterson et al. |
| 2004/0225220 A1 | 11/2004 | Rich |
| 2005/0041844 A1 | 2/2005 | Yamanaka |
| 2005/0043622 A1 | 2/2005 | Jensen |
| 2005/0054922 A1 | 3/2005 | Yudkovitch et al. |
| 2005/0131700 A1 | 6/2005 | Washburn et al. |
| 2005/0148878 A1 | 7/2005 | Phelps et al. |
| 2005/0154304 A1 | 7/2005 | Robinson |
| 2005/0243812 A1 | 11/2005 | Phelps |
| 2006/0036171 A1 | 2/2006 | Oberhoff et al. |
| 2006/0058655 A1 | 3/2006 | Little |
| 2007/0016050 A1 | 1/2007 | Moehring et al. |
| 2007/0161904 A1 | 7/2007 | Urbano |
| 2007/0167752 A1 | 7/2007 | Proulx et al. |
| 2008/0110263 A1 | 5/2008 | Klessel et al. |
| 2008/0114246 A1 | 5/2008 | Randall et al. |
| 2008/0114249 A1 | 5/2008 | Randall et al. |
| 2008/0114251 A1 | 5/2008 | Weymer et al. |
| 2008/0114253 A1 | 5/2008 | Randall et al. |
| 2008/0114255 A1 | 5/2008 | Schwartz et al. |
| 2009/0007414 A1 | 1/2009 | Phelps et al. |

OTHER PUBLICATIONS

U.S. Appl. No. 11/595,033, filed Nov. 10, 2006, Klessel et al.
U.S. Appl. No. 11/595,164, filed Nov. 10, 2006, Randall et al.
U.S. Appl. No. 11/595,171, filed Nov. 10, 2006, Urbano et al.
U.S. Appl. No. 11/595,334, filed Nov. 10, 2006, Urbana, Joshep A.
U.S. Appl. No. 11/595,335, filed Nov. 10, 2006, Randall et al.
U.S. Appl. No. 11/595,336, filed Nov. 10, 2006, Randall et al.
U.S. Appl. No. 11/595,340, filed Nov. 10, 2006, Urbano et al.
U.S. Appl. No. 11/595,341, filed Nov. 10, 2006, Randall et al.
U.S. Appl. No. 11/595,557, filed Nov. 10, 2006, Randall et al.
U.S. Appl. No. 11/595,601, filed Nov. 10, 2006, Urbano et al.
U.S. Appl. No. 11/595,674, filed Nov. 10, 2006, Randall et al.
U.S. Appl. No. 11/595,701, filed Nov. 10, 2006, Urbano et al.
U.S. Appl. No. 11/595,706, filed Nov. 10, 2006, Weymer et al.
U.S. Appl. No. 11/595,728, filed Nov. 10, 2006, Randall et al.
U.S. Appl. No. 11/595,729, filed Nov. 10, 2006, Randall et al.
Bae et al., "Bidirectional pixel based focusing in conventional B-mode ultrasound imaging", Electronic Letters, Oct. 29, 1998, 34(22), 2105-2107.
Bae et al., "Grating Lobe Reduction in Ultrasonic Synthetic Focusing", Electronics Letters, Jul. 4, 1991, 27(14), 1225-1227.
Bonnefous et al., "Time Domain Formulations of Pulse-Doppler Ultrasound and Blood Velocity Estimation by Cross Correlation", Ultrasonic Imaging, 1986, 8, 73-85.
Chang et al., "Phase-Error-Free Quadrature Sampling Technique in the Ultrasonic B-Scan Imaging System and Its Application to the Synthetic Focusing System", IEEE Transactions on Ultrasonics, Ferroelectrics, and Frequency Control, May 1993, 40(3), 216-223.
Cho et al., "Multi-Order Sampling for Digital Beamforming of Wide-Band Signals", IEEE Transactions on Ultrasonics, Ferroelectrics, and Frequency Control, May 1996, 43(3), 495-499.
Coldani et al., "An Instrument to Measure Velocity Profile by Means of Ultrasound Techniques", Journal of Mechanics in Medicine and Biology, 2003, 3(1), 21-30.
Direct Medical Systems, Installation Manual, "PUPS (Pocket Ultrasound Probe System)", http://www.innovasound.us, Direct Medical Systems LLC, Oct. 4, 2010, 4 Pages.
Flax et al., "Phase-Aberration Correction Using Signals From Point Reflectors and Diffuse Scatterers: Basic Principles", IEEE Transactions on Ultrasonics, Ferroelectrics, and Frequency Control, Nov. 1988, 35(6), 758-767.
Han et al., "P3G-6 Error-Free Pulse Compression Method for Ultrasound Beamforming Using Sigma-Delta Modulation", IEEE Ultrasonics Symposium, Vancouver, BC, Oct. 2-6, 2006.
International Patent Application No. PCT/US2007/23491, International Preliminary Report on Patentability, Feb. 26, 2009, 8 pages.
International Patent Application No. PCT/US2007/23491, International Search Report, Jun. 11, 2008, 2 pages.
International Patent Application No. PCT/US2007/23491, Written Opinion, Jun. 11, 2008, 5 pages.
Jensen, A. J., "Artifacts in blood velocity estimation using ultrasound and cross-correlation", Medical and Biological Engineering and Computing, 1994, 32(4) (Suppl.), s165-s170.
Jensen, A. J., "Directional Synthetic Aperture Flow Imaging", IEEE Transactions on Ferroelectrics, and Frequency Control, Sep. 2004, 51(9), 1107-1118.

Jensen, A. J., "Equipment and methods for synthetic aperture anatomic and flow imaging", IEEE Ultrasonics Symposium, 2002, 1555-1564.

Jensen, A. J., "Range/velocity limitations for time-domain blood velocity estimation", Ultrasound in Medicine and Biology, 1993, 19(9), 741-749.

Jensen, A. J., "Velocity Vector Estimation in Synthetic Aperture Flow and B-Mode Imaging", IEEE, 2004, 32-35.

Karaman et al., "Adaptive Multi-element Synthetic Aperture Imaging with Motion and Phase Aberration Correction", IEEE Transactions on Ferroelectrics, and Frequency Control, Jul. 1998, 45(4), 1077-1087.

Karaman et al., "Synthetic Aperture Imaging for Small Scale Systems", IEEE Transactions on Ferroelectrics, and Frequency Control, May 1995, 42(3), 429-442.

Karaman et al., "VLSI Circuits for Adaptive Digital Beamforming in Ultrasound Imaging", IEEE Transactions on Medical Imaging, Dec. 1993, 12(4), 711-720.

Kasai et al., "Real-Time Two-Dimensional Blood Flow Imaging Using an Autocorrelation Technique", IEEE Transactions on Sonics and Ultrasonics, May 1985, SU-32(3), 458-464.

Ketterling et al., "Operational Verification of a 40-MHz Annular Array Transducer", IEEE Transactions on Ferroelectrics, and Frequency Control, Mar. 2006, 53(3), 623-630.

Kim et al., "Pipelined Sampled-Delay Focusing in Ultrasound Imaging Systems", Ultrasonic Imaging, 1987, 9, 75-91.

Linebarger et al., "A Fast Method for Computing the Coarray of Sparse Linear Arrays", IEEE Transactions on Antennas and Propagation, Sep. 1992, 40(9), 1109-1112.

Lockwood et al., "Real-Time 3-D Ultrasound Imaging Using Sparse Synthetic Aperture Beamforming", IEEE Transactions on Ferroelectrics, and Frequency Control, Jul. 1998, 45(4), 980-988.

Meng, X., "A Discussion of Second Order Sampling for Bandpass Signal", Signal Processing Proceedings, 1998, 51-52.

Nikolov et al., "Three-Dimensional Real-Time Synthetic Aperture Imaging Using a Rotating Phased Array Transducer", IEEE International Ultrasonics Symposium, Munich, 2002, 2-5.

Nock et al., "Synthetic Receive Aperture Imaging with Phase Correction for Motion and for Tissue Inhomogeneities—Part I: Basic Principles", IEEE Transactions on Ferroelectrics, and Frequency Control, Jul. 1992, 39(4), 489-495.

O'Donnell, M., "Coded Excitation System for Improving the Penetration of Real-Time Phased-Array Imaging Systems", IEEE Transactions on Ultrasonics, Ferroelectrics and Frequency Control, 1992, 39(3), 341-351.

O'Donnell, M., "Correlation-Based Aberration Correction in the Presence of Inoperable Elements", IEEE Transactions on Ferroelectrics, and Frequency Control, Nov. 1992, 39(6), 700-707.

Payne et al., "Towards an Integrated Hand-Held Multi-Element Array Transducer for Ultrasound Imaging", Acoustic Sensing and Imaging, Mar. 29-30, 1993, Conference Publication No. 369, 13-16.

Powers, J. E., "Ultrasound Phased Array Delay Lines Based on Quadtrature Sampling Techniques", IEEE Transactions on Sonics and Ultrasonics, Nov. 1980, SU-27(6), 287-294.

Song et al., "A New Digital Phased Array System for Dynamic Focusing and Steering with Reduced Sampling Rate", Ultrasonic Imaging, 1990, 12, 1-16.

Tavli et al., "Correlation Processing for Correction of Phase Distortions in Subaperture Imaging", IEEE Transactions on Ferroelectrics, and Frequency Control, Nov. 1999, 46(6), 1477-1488.

Thomenius E. K., "Evolution of Ultrasound Beamformers", IEEE Ultrasonics Symposium, (1996), 1615-1622.

Tomov et al., "Compact FPGA-Based Beamformer Using Oversampled 1-bit A/D Converters", EEE Transactions on Ferroelectrics, and Frequency Control, May 2005, 52(5), 870-880.

Trahey et al., "Synthetic Aperture Imaging with Phase Correction for Motion and for Tissue Inhomogeneities—Part II: Effects of and Correction for Motion", IEEE Transactions on Ferroelectrics, and Frequency Control, Jul. 1992, 39(4), 496-501.

USB Ultrasound Probe User Manual, Direct Medical Systems LLC, Aug. 2006.

Vaughan et al., "The Theory of Bandpass Sampling", IEEE Transactions on Signal Processing, Sep. 1991, 39(9), 1973-1984.

Ylitalo, J., "On the signal-to-noise ratio of a synthetic aperture ultrasound imaging method", European Journal of Ultrasound, 1996, 3, 277-281.

Zoltowski et al., "Beamspace Root-Music for Minimum Redundancy Linear Arrays", IEEE Transactions on Signal Processing, Jul. 1993, 41(7), 2502-2507.

Transducer Element 601

Memory 613 ———————————————————————⌒——— 701
Memory 614 ————————————————————710 ⌒——————— 702
Memory 615 ———————————————————⌒————— 703

Transducer Element 602

Memory 616 ——————————————————⌒—————— 704
Memory 617 —————————————————⌒——————— 705
Memory 618 ————————————————⌒———————— 706

Transducer Element 603

Memory 619 ———————————————————⌒————— 707
Memory 620 ——————————————————⌒—————— 708
Memory 621 —————————————————⌒——————— 709

|←——— 2T ———→|

Figure 7

| Time | Write | Read |
|---|---|---|
| 1 | 1a | . |
| 2 | 2a | . |
| 3 | 3a | . |
| 4 | 4a | . |
| 5 | 5a | . |
| 6 | 1b | 1a |
| 7 | 2b | 1a |
| 8 | 3b | 2a |
| 9 | 4b | 2a |
| 10 | 5b | 3a |
| 11 | T | 3a |
| 12 | T | 4a |
| 13 | T | 4a |
| 14 | T | 5a |
| 15 | T | 5a |
| 16 | 1a | 1b |
| 17 | 2a | 1b |
| 18 | 3a | 2b |
| 19 | 4a | 2b |
| 20 | 5a | 3b |
| 21 | T | 3b |
| 22 | T | 4b |
| 23 | T | 4b |
| 24 | T | 4b |
| 25 | T | 4b |
| 26 | T | 5b |
| 27 | T | 5b |
| 28 | T | 5b |
| 29 | T | 5b |
| 30 | 1b | 1a |
| 31 | 2b | 1a |
| 32 | 3b | 1a |
| 33 | 4b | 1a |
| 34 | 5b | 2a |
| 35 | T | 2a |
| 36 | T | 2a |
| 37 | T | 2a |
| : | : | : |

Figure 23

TRANSDUCER ARRAY IMAGING SYSTEM

CROSS-REFERENCE TO RELATED APPLICATIONS

This application is a continuation of U.S. patent application Ser. No. 11/595,033, titled "Transducer Array Imaging System", filed on Nov. 10, 2006, and currently pending. This application is related to U.S. patent application Ser. No. 11/595,171, titled "Transducer Array Imaging System", filed on Nov. 10, 2006 and U.S. patent application Ser. No. 11/595,336, titled "Transducer Array Imaging System", filed on Nov. 10, 2006. The contents of all three applications hereby incorporated by reference herein in their respective entirety, for all purposes.

BACKGROUND

Many transducer-array based systems, such as ultrasound imaging systems and including radar, sonar, optical, and audible sound systems and the like, use a remote module sometimes referred to as a probe. The probe typically houses an array of transducers and the system typically performs coherent signal processing. In the case of medical ultrasound, a user places the probe on the patient and the transducers emit energy (e.g., ultrasound waves) into the patient's body. The transducer array also receives energy that is reflected or echoed by the patient's body back to the transducers. The received echo waves are converted to electrical signals. The electrical signals are processed by the medical imaging system in order to create a visual representation of the targeted area inside the patient's body. Other non-medical uses of ultrasound include non-destructive testing of various materials.

Currently, medical imaging systems use typically large multi-conductor cables to carry the electrical signals from the probe to the system's main processing unit. Because of the large number of transducer elements typically required, a significant amount of energy is required to be carried by the cable. The relatively large cable creates difficulties electrically, medically, and physically.

From a physical perspective, for example, the cable is ergonomically burdensome. From an electrical perspective, the larger cable degrades the electrical interface to the main unit and adds capacitance to the system. By adding capacitance to the system, the impedance of the cable is significantly lower than the transducer array. As a result, the transducers may need to be powered with greater currents. Also, the cable capacitance may undesirably result in a lower signal-to-noise ratio (SNR).

From a medical perspective, the cable creates a problem where sterility is an issue. A probe used in a sterile field must either be sterilizable, or must be covered with a sterile sheath. With a cabled probe, the probe is covered with a sterile sheath that extends back over the cable, yet the covered cable eventually extends out of the sterile field because the main unit it not sterilizable. As the probe is used, the attached cable slides into and out of the sterile field. Once the cable slides out of the sterile field, the necessary sterility is compromised. As a result, a user is limited in using and moving the cabled probe.

SUMMARY

The disclosed embodiments include a method, system, and device for conducting ultrasound interrogation of a medium. The method includes transmitting a non-beamformed or beamformed ultrasound wave into the medium, receiving more than one echoed ultrasound wave from the medium, and converting the received echoed ultrasound wave into digital data. The novel method may further transmit the digital data. In some embodiments, the transmitting may be wireless. The novel device may include transducer elements, an analog-to-digital converter in communication with the transducer elements, and a transmitter in communication with the analog-to-digital converter. The transducers may operate to convert a first electrical energy into an ultrasound wave. The first electrical energy may or may not be beamformed. The transducers also may convert an echoed ultrasound wave into a second electrical energy. The analog-to-digital converter may convert the electrical energy into digital data, and the transmitter may transmit the digital data.

Embodiments contemplate methods and devices for conducting ultrasound interrogation of a medium. In one or more embodiments an ultrasound echo wave may be received at a first transducer element of a transducer array in a handheld probe of an ultrasound system. The ultrasound echo wave may also be received at a second transducer element of the transducer array in the handheld probe of the ultrasound system. Embodiments also contemplate that the ultrasound echo wave may be received at a third transducer element of the transducer array in the handheld probe of the ultrasound system. Embodiments also contemplate processing into digital data the ultrasound echo wave received at the first transducer element and the ultrasound echo wave received at the second transducer element. In one or more embodiments, the processing may preclude data representative of the ultrasound echo wave received at the third transducer element from being included in the digital data. Also, embodiments contemplate that the processing may include reducing the digital data without beamforming data representative of the ultrasound echo wave received at the first transducer element with data representative of the ultrasound echo wave received at the second transducer element. In one or more embodiments the digital data may be transmitted to a location relatively remote from the handheld probe.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 7 is an example illustration of signals transmitted from each of transducer elements and received back on respective transducer elements;

FIG. 23 is a chart representing a sequence of writes and reads to a ping-pong frame buffer.

DETAILED DESCRIPTION

Figure 1:
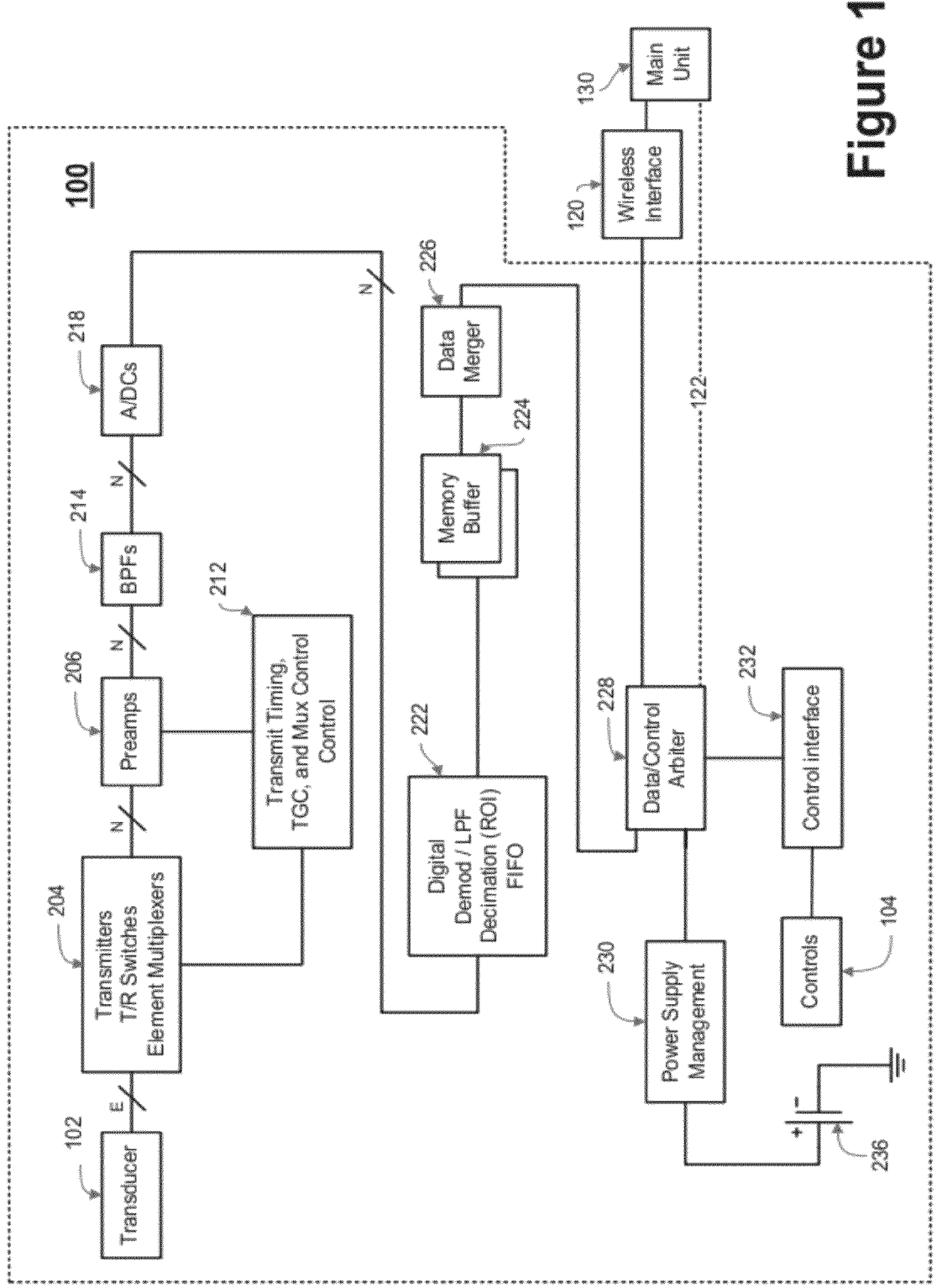
FIG. 1 is a block diagram illustrating various components of an example probe.

The subject matter of the described embodiments is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Similarly, with respect to the components shown in the Figures, it should be appreciated that many other components may be included with the scope of the embodiments. The components are selected to facilitate explanation and understanding of the embodiments, and not to limit the embodiments to the components shown.

There are many transducer array systems contemplated by the disclosed embodiments. Most of the description focuses on a description of a diagnostic medical ultrasound system, however the disclosed embodiments are not so limited. The description focuses on diagnostic medical ultrasound systems solely for the purposes of clarity and brevity. It should be appreciated that disclosed embodiments apply to numerous other types of methods and systems.

In a transducer array system, the transducer array is used to convert a signal from one format to another format. For example, with ultrasound imaging the transducer converts an ultrasonic wave into an electrical signal, while a RADAR system converts an electromagnetic wave into an electrical signal. While the disclosed embodiments are described with reference to an ultrasound system, it should be appreciated that the embodiments contemplate application to many other systems. Such systems include, without limitation, RADAR systems, optical systems, audible sound reception systems. For example, in some embodiments, the audible sound reception system may be used at a sporting event to detect on-field sounds with a large microphone and wirelessly transmit the sound back to a main unit.

In addition, although the disclosed embodiments are described with reference to a medical ultrasound system, it should be appreciated that the embodiments contemplate application to many other types of ultrasound system. For example, the disclosed embodiments apply to non-destructive testing systems. Such non-destructive testing systems may be used to inspect metal, wood, plastics, etc. for structural integrity and/or to ascertain certain characteristics of the material. For example, the embodiments may be used to inspect piping for cracks and/or to determine their thickness. Also, non-destructive testing systems may be used to inspect material connections, like metal welds, and the like.

Also, although the disclosed embodiments are described with reference to a diagnostic system, it should be appreciated that the embodiments contemplate application to many other types of systems, including, for example, therapeutic ultrasound systems.

FIG. 1 is a block diagram illustrating various components of an example probe 100 according to one embodiment. It should be appreciated that any or all of the components illustrated in FIG. 1 may be disposed within a housing (not shown in FIG. 1) having any form factor. Probe 100 may include circuitry that is represented in FIG. 1 as a series of blocks, each having a different function with respect to the operation of probe 100. While the following discussion treats each of the blocks as a separate entity, an embodiment contemplates that any or all of such functions may be implemented by hardware and/or software that may be combined or divided into any number of components. For example, in one embodiment the functions represented by any or all of the blocks illustrated in FIG. 1 may be performed by components of a single printed circuit board or the like.

Transducer 102 represents any number of transducer elements that may be present in probe 100. Electroacoustic ultrasound transducer types include piezoelectric, piezoceramic, capacitive, microfabricated, capacitive microfabricated, piezoelectric microfabricated, and the like. Some embodiments may include transducers for sonar, radar, optical, audible, or the like. Transducer 102 elements may be comprised of individual transmitter and receiver elements. For example, transmitter 204 includes one or more transmitters that drive each of the transducer elements represented by transducer 102, as well as transmit and/or receive switch circuitry that isolates transmitter 204 from a receiver channel (which may be part of preamp 206 in FIG. 1) during the transmit event. The transmitters may produce a focused, unfocused or defocused transmit beam, depending on the intended application. For example, the focused beam may be useful when high peak acoustic pressure is desired as is the case of harmonic imaging. One embodiment uses defocused transmit beams to provide insonfication or interrogation of a relatively larger spatial region as required for synthetic transmit focusing. The transmit beam may be configured to elicit return echo information that is sufficient to produce an ultrasound image along an imaging plane.

Probe 100 receiver circuitry (not shown in FIG. 1) may include a low-noise, high-gain preamplifier 206 for each receive channel (e.g., manufactured by Texas Instruments model number VCA2615 dual-channel variable gain amplifier or the like). Any number of receive channels may be present in an embodiment. Preamplifier 206 may provide variable gain throughout a data acquisition time interval. Preamplifier 206 may be followed by bandpass filter 214 that may operate to reduce the noise bandwidth prior to analog-to-digital (A/D) conversion.

Transmit timing, time-gain control (TGC) and multiplexer control 212 may in some embodiments provide timing and control of each transmit excitation pulse, element multiplexer setting, and TGC waveform. An example unipolar transmitter channel circuit may include, for example, a transistor functioning as a high-voltage switch followed by a capacitor. The capacitor may be charged to a high voltage (e.g., 100V), and then discharged through the transistor upon excitation by a trigger pulse. Similar transistor-based switches may also be used for transmit/receive isolation, element-to-channel multiplexing, etc. Other embodiments may include more sophisticated transmitters capable of bipolar excitations and/or complex wave shaping and/or the like.

To focus the transmitted ultrasound energy at a desired spatial location, in some embodiments, the excitation pulse of each transducer element may be delayed in time relative to the other elements. Such a delay pattern may cause the ultrasound waves from excited elements to combine coherently at a particular point in space, for example. This may be beneficial for a focused and/or an acoustic transmit focused system, for example. Alternatively, the transmit waveforms may be delayed in such a way as to defocus the beam. This may be beneficial for a system employing synthetic transmit focusing, for example.

In some embodiments, a TGC portion of block 212 may provide a programmable analog waveform to adjust the gain of variable gain preamplifier 206. The analog waveform may be controlled by a user through a user interface such as, for example, a set of slide controls used to create a piece-wise linear function. In some embodiments, this piece-wise linear function may be calculated in software, and then programmed into sequential addresses of a digital memory, for example. The digital memory may be read out sequentially at a known time interval beginning shortly after the transmit excitation pulse, for example. In some embodiments, output of the memory may be fed into a digital-to-analog converter (DAC) to generate the analog waveform. In some embodiments, time may be proportional to the depth of the ultrasound echoes in the ultrasound receiver. As a result, echoes emanating from tissue deep within a patient's body may be attenuated more than those from shallow tissue and, therefore, require increased gain. The controlling waveform may also be determined automatically by the system by extracting gain information from the image data, for example. Also, in some embodiments, the controlling waveform may be predetermined and stored in the memory, and/or determined during system operation.

One embodiment may include a multiplexer within block 204 for multiplexing a relatively large array of transducer 102 elements into a smaller number of transmit and/or receive channels. Such multiplexing may allow a smaller ultrasound aperture to slide across a full array on successive transmit events. Both transmit and receive apertures may be reduced to the same number of channels or they may differ from each other. For example, the full array may be used for transmitting while a reduced aperture may be used on receive. It should be appreciated that any combination of full and/or decimated arrays on both transmit and receive are contemplated by the disclosed embodiments.

Multiplexing also may provide for building a synthetic receive aperture by acquiring different subsets of the full aperture on successive transmit events. Multiplexing may also provide for the grouping of elements by connecting adjacent elements on either transmit or receive. Grouping by different factors is also possible such as, for example, using a group of three elements on transmit and a group of two elements on receive. One embodiment may provide multiplexing for synthetic transmit focusing mode and multiplexing for acoustic transmit focusing mode and provide for switching from one mode to the other, for example, on frame boundaries. Other multiplexing schemes are also possible and are contemplated by the disclosed embodiments.

Multiplexing may be controlled by using transmit timing, TGC and multiplexer control 212. Various transmit and/or receive elements may be selected when imaging a particular spatial region. For example, ultrasound echo data for an image frame may be acquired by sequentially interrogating adjacent sub-regions of a patient's body until data for the entire image frame has been acquired. In such a case, different sub-apertures (which may include elements numbering less than the full array) may be used for some or all sub-regions. The multiplexer control function may be programmed to select the appropriate sub-aperture (transmit and/or receive), for example, for each transmit excitation and each image region. The multiplexer control function may also provide control of element grouping.

Analog to Digital (A/D) converter 218 may convert the analog image data received from probe 100 into digital data using any method. Digital demodulator 222 may include any type of digital complex mixer, low-pass filter and re-sampler after each A/D converter channel, for example. In some embodiments, the digital mixer may modulate the received image data to a frequency other than a center frequency of probe 100. It some embodiments, this function may be performed digitally rather than in the analog or sampling domains to provide optimum flexibility and minimal analog circuit complexity. The low-pass filter may reduce the signal bandwidth after mixing and before re-sampling when a lower sampling rate is desired. One embodiment may use quadrature sampling at A/D converter 218 and, therefore, such an embodiment may not require a quadrature mixer to translate the digital data (e.g., radio frequency (RF)) signals of transducer 102 to a baseband frequency. However, complex demodulation by means of an analog or digital mixer or the like may also be used in connection with an embodiment.

Memory buffer 224 may have sufficient storage capacity to store up to, for example, two frames of data. Such a frame-sized buffer 224 may allow frames to be acquired at a rate substantially higher than the rate at which frames can be transferred to main unit 130 (or some other device) across wireless interface 120, for example. Such a configuration may, in an embodiment, be preferable to acquiring each frame over a longer time interval because a longer time interval may reduce a coherence of the acquired data throughout the frame. If frame transmission rates are at least as fast as frame acquisition rates, a smaller memory buffer 224 may be used in some embodiments. One embodiment uses a "ping-pong" buffer fed by the receiver channels as memory buffer 224. Data from multiple channels may be time interleaved into memory buffer 224. For example, 32 receiver channels each sampled at the rate of 6 MHz would produce a total baseband data rate of 192M words per second, which is well within the rates of conventional DDR2 SDRAM. The ping-pong nature of memory buffer 224 may allow new data to fill buffer 224 while previously acquired data is read from memory and sent to wireless interface 120, for example.

Memory buffer 224 is followed by data merger 226. Data merger 226 may operate to merge receive channel data into one or more data streams before advancing the data stream to wireless interface 120 for transmission to main unit 130, for example. Data from data merger 226 may be sent across wireless interface 120 (and/or across wired interface 122) at a rate that is appropriate for the transmission medium. The data from the receive channels may be multiplexed in some fashion prior to transmission over wireless interface 120 and/or wired interface 122. For example, time-division multiplexing (TDM) may be used. Other types of multiplexing are also possible such as, for example, frequency-division multiplexing (FDM), code-division multiplexing (CDM), and/or some combination of these or other multiplexing techniques.

In addition to image data transfer, control information may be transferred between probe 100 and main unit 130. Such control data may be transferred over the same communication link, such as wireless interface 120 and/or wired interface 122, or some other communication link. Control commands may be communicated between main unit 130 and probe 100 (and/or some other devices). Such control commands may serve various purposes, including for example, instructing a mode of operation and/or various imaging parameters such as maximum imaging depth, sampling rate, element multiplexing configuration, etc. Also, control commands may be communicated between probe 100 and main unit 130 to communicate probe-based user controls 104 (e.g., button pushes) and probe operational status (e.g., battery level from power supply management 230), and the like.

The probe's status may include an indicator and/or display of certain values relevant to the operation of the system. For example, the indicator may be visible, audio, and/or some combination thereof. Without limitation, the indicator may indicate power status, designation of device, type of device, frequency range, array configuration, power warnings, capability of a remote unit, quality of transmission of digital data, quantity of errors in transmission of digital data, availability of power required for transmission of digital data, change in transmission rate, completion of transmission, quality of data transmission, look-up tables, programming code for field programmable gate arrays and microcontrollers, transmission characteristics of the non-beamformed ultrasound wave, processing characteristics of the echoed ultrasound wave, processing characteristics of the digital data, and/or transmission characteristics of the digital data, etc. Also, the indicator may show characteristics of a power source like capacity, type, charge state, power state, and age of power source.

In some embodiments, data/control arbiter 228 may be responsible for merging control information and image data communicated between probe 100 and main unit 130. The control information may be passed from control interface 232, where it is collected to data/control arbiter 228 for transmission to main unit 130. In some embodiments, control and image data may be distinguishable from each other when sent across wireless interface 120 and/or wired interface 122 to facilitate proper handling at main unit 130. In other embodiments, there may be no such distinction. In addition, data/control arbiter 228 may accept control commands from main unit 130 (and/or another device) and respond by appropriate programming of probe 100 circuitry, memory-based tables, registers, etc.

It will be appreciated that in an embodiment where probe 100 is to be used in a sterile environment, the use of wireless interface 120 to main unit 130 may be desirable, as the use of wireless interface 120 avoids many of the problems associated with having a physical connection between probe 100 and main unit 130 that passes into and out of a sterile field. In other embodiments, certain sheathing or sterilization techniques may eliminate or reduce such concerns. In an embodiment where wireless interface 120 is used, controls 104 may be capable of being made sterile so as to enable a treatment provider to use controls 104 while performing ultrasound imaging tasks or the like. However, either wireless interface 120 or wired interface 122, or a combination of both, may be used in connection with an embodiment.

Probe 100 circuitry also includes power supply 236, which may operate to provide drive voltage to the transmitters as well as power to other probe electronics. Power supply 236 may be any type of electrical power storage mechanism, such as one or more batteries or other devices. In one embodiment, power supply 236 may be capable of providing approximately 100V DC under typical transmitter load conditions. Power supply 236 also may also be designed to be small and light enough to fit inside a housing of probe 100, if configured to be hand held by a treatment provider or the like. In addition, power supply management circuitry 230 may also be provided to manage the power provided by power supply 236 to the ultrasound-related circuits of probe 100. Such management functions include monitoring of voltage status and alerts of low-voltage conditions, for example.

Controls 104 may be provided to control probe 100. Control interface 232 may pass user input received from controls 104 to data/control arbiter 228 for processing and action, if necessary. Such control information may also be sent to the main unit 130 through either wireless interface 120 and/or wired interface 122. In addition to sending data to main unit 130, wireless interface 120 may also receive control or other information from main unit 130. This information may include, for example, image acquisition parameters, look-up tables and programming code for field programmable gate arrays (FPGAs) or microcontrollers residing in probe 100, or the like. Controller interface 232 within probe 100 may accept and interpret commands from main unit 130 and configure probe 100 circuitry accordingly.

Now that an example configuration of components of probe 100 has been described, an example configuration of components of main unit 130 will be discussed with reference to FIG. 2. It should be noted that any or all of the components illustrated in FIG. 2 may be disposed within one or more housings (not shown in FIG. 2) having any form factor.

As discussed above, probe 100 may be in communication with main unit 130 by way of wireless interface 120 and/or wired interface 122. It will be appreciated that in an embodiment most data transfer occurs from probe 100 to main unit 130, although in some embodiments more data may be transferred from main unit 130 to probe 100. That is, large amounts of image data sent from probe 100 may be received by main unit 130, as well as control information or the like. Control information is managed and, in many cases, generated by Central Processing Unit (CPU) controller 332. CPU controller 332 may also be responsible for configuring circuitry of main unit 130 for an active mode of operation with required setup parameters.

In some embodiments, data/control arbiter 310 may be responsible for extracting control information from the data stream received by wireless interface 120 and/or wired interface 122 and passing it to CPU 332 while sending image data from the data stream to input buffer 312. Data/control arbiter 310 may also receive control information from CPU 332, and may transfer the control information to probe 100 via wireless interface 120 and/or wired interface 122.

A user, such as a treatment provider or the like, may control the operations of main unit 130 using control panel 330. Control panel 330 may include any type of input or output device, such as knobs, pushbuttons, a keyboard, mouse, and/or trackball, etc. Main unit 130 may be powered by any type of power supply (not shown in FIG. 2) such as, for example, a 120 VAC outlet along with AC-DC converter module, and/or a battery, etc.

To facilitate forming an image on display 350 (e.g., pixel-forming—a process that generates an ultrasound image from the image data received from probe 100), the incoming image data may be stored in input buffer 312. In an embodiment, input buffer 312 may be capable of storing up to approximately two frames of data, for example, and may operate in a "ping-pong" fashion whereby a previously received frame of data is processed by pixelformer 322 while a new incoming frame is written to another page of memory in input buffer 312. Pixelformer 322 may be any combination of hardware and/or software that is capable of transforming raw image data received from the receive channels and the transmit events (e.g., from probe 100) into a pixel-based image format. This may be performed, in just one example, by coherently combining data from various transmit and receive elements, or groups of elements, to form an image focused optimally at each pixel. Many variations of this approach may be used in connection with an embodiment. Also, this function may include a beamformer that focuses samples along beam directions. The focused sample data may be converted to a Cartesian format for display on display 350.

Once a frame of complex pixel data has been formed, it may be stored in frame buffer 324 for use by either flow estimator 326 and/or image processor 328. In an embodiment, flow estimator 326 uses, for example, Doppler or cross-correlation methods to determine one or more flow characteristics from the received image (e.g., ultrasound echo) data. Once the flow estimation parameters have been computed, they may be encoded into data values and either stored in frame buffer 324 for access by image processor 328 and/or sent directly to image processor 328. Note that the term "pixel" as used herein typically refers to an image sample, residing on a Cartesian polar and/or non-uniform coordinate grid, computed by processing captured echo signal data. Actual display pixels may differ from these image pixels in various ways. For example, the display pixels, as presented on display 350, may be a scaled, resized, filtered, enhanced, or otherwise modified version of the image pixels referred to herein. These functions may be performed by a processor, for example, image processor 328. Pixel also may refer to any finite level, value, or subcomponent of an image. For example, an image that is made up of a number of subcomponents, both visual and otherwise, may be referred to as a pixel.

Spectral Doppler processor (SDP) 320 may receive focused baseband data from pixelformer 322 from one or more spatial locations within the image region in a periodic or other fashion. The spatial locations may be referred to as range gates. SDP 320 may perform high-pass filtering on the data to remove signal contributions from slow moving tissue or the like. The remaining higher frequency signals from blood flow may be in the normal audio frequency range and these signals may be conventionally presented as an audible signal by speaker 318. Such audio information may, for example, assist a treatment provider in discerning a nerve from a blood vessel and/or a vein from an artery. SDP 320 may also perform spectral analysis via a discrete Fourier transform computation, or other means, to create an image representing a continuously updated flow velocity display (i.e., a time-varying spectrogram of the blood flow signal). The velocity data may be sent through image processor 328 for further processing and display.

A user of main unit 130 may use microphone 314 for controlling main unit 130 using, for example, voice recognition technology. Alternately, or in addition to using microphone 314 for control purposes, a user may use microphone 314 for taking notes while examining a patient. Audio notes may be saved separate from, or along with, video data.

Audio codec 316 may accept audio data input from microphone 314 and may interface with CPU 332 so audio data received by audio codec 316 may be stored and/or interpreted by CPU 332. Such audio interpretation may facilitate system control by way of, for example, voice commands from a user of main unit 130. For example, frequently-used system commands may be made available via voice control. Such commands may also be made available by way of control panel 330, for example. Audio storage facilitates audio annotation of studies for recording patient information, physician notes and the like. The audio data may first be converted to a compressed format such as MP3 before storing in, for example, storage 338. Other standard, proprietary, compressed or uncompressed formats may also be used in connection with an embodiment. Speaker 318 may provide audio output for reviewing stored annotation or for user prompts from main unit 130 resulting from error conditions, warnings, notifications, etc. As mentioned above, Doppler signals may also be output to speaker 318 for user guidance in range gate and/or steering line placement and vessel identification.

Video interface 334 may be in communication with image processor 328 to display 350 by way of CPU 332. Display 350 may be any device that is capable of presenting visual information to a user of main unit 130 such as, for example, an LCD flat panel, CRT monitor, composite video display or the like. Video data may also be sent to storage 338, which may be a VCR, disk drive, USB drive, CD-ROM, DVD or other storage device. Prior to storage, for example, still image frames of data may be encoded in a compressed format such as JPEG, JPEG2000 or the like. Image clips or sequences may be encoded in a format such as MJPEG, MJPEG2000 or a format that includes temporal compression such as MPEG. Other standard or proprietary formats may be used as well.

Image processor 328 may accept either complex and/or detected tissue image data and then filter it temporally (i.e., frame to frame) and spatially to enhance image quality by improving contrast resolution (e.g., by reducing acoustic speckle artifact) and by improving SNR (e.g., by removing random noise). Image processor 328 may also receive flow data and merge it with such tissue data to create a resultant image containing both tissue and flow information. To accomplish this, image processor 328 may use an arbitration process to determine whether each pixel includes flow information or tissue information. Tissue and/or flow pixels may also be resized and/or resealed to fit different pixel grid dimensions either prior to and/or after arbitration. Pixels may also be overwritten by graphical or textual information. In an embodiment, both the flow arbitration and graphical overlay may occur just prior to image display to allow the tissue and flow images to be processed independently.

Temporal filtering typically may be performed on both the tissue and flow data prior to merging the data. Temporal filtering can yield significant improvements in SNR and contrast resolution of the tissue image and reduced variance of the flow image while still achieving a final displayed temporal resolution suitable for clinical diagnosis. As a result, relatively higher levels of synthetic aperture subsampling may be provided, thereby reducing the required and/or desired number of receiver channels (and, consequently, in some embodiments power consumption of probe 100). Temporal filtering typically involves filtering data from frame to frame using either an FIR or IIR-type filter. In one embodiment, a simple frame averaging method may be used as discussed below, for example.

Temporal filtering and/or persistence is commonly applied to frames of ultrasound data derived from, for example, tissue echoes. When the acquisition frame rate exceeds the rate of motion of anatomical structures, low-pass filtering across frames can reduce random additive noise while preserving or enhancing image structures. Also, minute degrees of motion—commonly due to patient or operator movement—help to reduce image speckle, which is caused by the interference of acoustic energy from randomly distributed scatterers that are too small to be resolved with the frequency range of ultrasound probe 100. Speckle is coherent by its nature so, in the absence of motion, it may produce the same pseudo-random noise pattern on each image frame. However, small amounts of motion diversify the speckle enough to make low-pass filtering across frames effective at reducing it.

A simple method of temporal filtering may involve averaging neighboring frames. An example of the recursive version of a moving-average filter is described as follows where $X(n)$ is the input frame acquired at time n, $Y(n)$ is the corresponding output frame, and k is a frame delay factor that sets the size of the averaging window:

$$Y(n)=Y(n-1)+X(n)-X(n-k) \quad (1)$$

Another simple low-pass filter is a first-order IIR filter of the form:

$$Y(n)=C \times Y(n-1)+(1-C) \times X(n) \quad (2)$$

In such an embodiment, the coefficient C sets the filter's time constant and the degree of low-pass filtering applied to the frame sequence. It should be appreciated that Equations (1) and (2) are just examples of possible filters and filtering techniques that may be used in connection with an embodiment.

Control panel 330 may provide pushbuttons, knobs, etc., to allow the user to interact with the system by changing modes, adjusting imaging parameters, and so forth. Control panel 330 may be operatively connected to CPU 332 by way of, for example, a simple low bandwidth serial interface or the like. Main unit 130 may also include one or more I/O interfaces 336 for communication with other devices, computers, a network or the like by way of a computer interface such as USB, USB2, Ethernet or WiFi wireless networking, for example. Such interfaces allow image data or reports to be transferred to a computer or external storage device (e.g., disk drive, CD-ROM or DVD drive, USB drive, flash memory, etc.) for later review or archiving, and may allow an external computer or user to control main unit 130 remotely.

There are at least two techniques used for interrogating a medium and processing the data needed to create an ultrasound image: synthetic transmit focusing and acoustic transmit focusing. In synthetic transmit focusing, the interrogating ultrasound waves may be transmitted into the medium, from various locations in the array, in an unfocused or defocused manner, and reflected waves are received and processed. Somewhat differently, with acoustic transmit focusing the interrogating ultrasound waves may be transmitted in a way that provides focus at certain spatial locations in the medium, and therefore the transmitted ultrasound wave cooperates to form a "beam." Various embodiments contemplate synthetic transmit focusing, acoustic transmit focusing, and/or a combination of both. One embodiment contemplates dynamically switching between synthetic transmit focusing and acoustic transmit focusing modes periodically. For example, color flow data acquisition may use acoustic transmit focusing while tissue imaging may use synthetic transmit focusing. Color flow and tissue data may be collected on some alternating basis, for example. Other embodiments may include the use of non-beamformed techniques, in which, a beam may not be formed and/or be partially formed. Similarly, these beamformed and non-beamformed techniques may be used after the medium is interrogated in evaluating the echoed ultrasound waves and/or the digital data from which these waves are formed.

Figure 3:
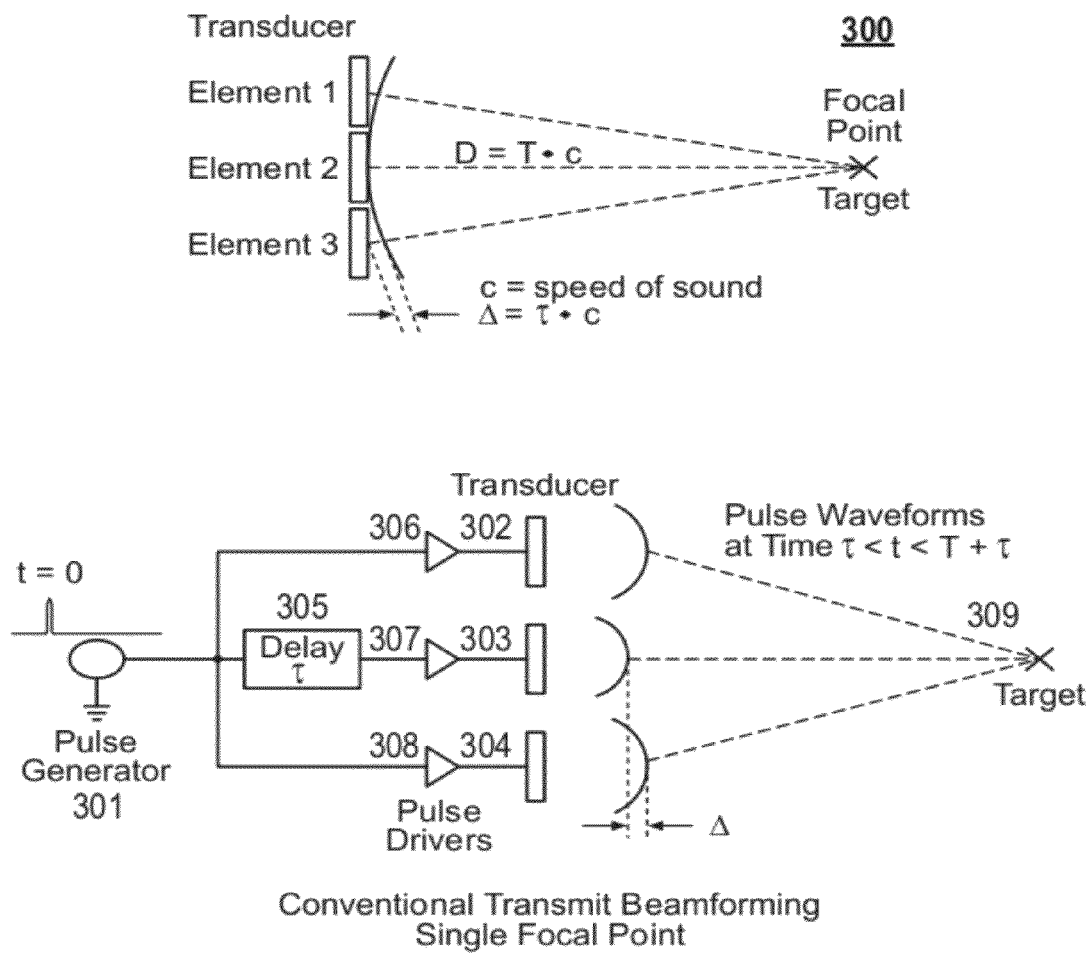
FIG. 3 is a block diagram of a system for transmitting an acoustic transmit focused wave.

FIG. 3 is a block diagram of a system 300 for transmitting an acoustic transmit focusing wave. As shown in FIG. 3, a pulse generator 301 provides a signal to a transducer element 302, a transducer element 303, and a transducer element 304. The signal provided by pulse generator 301 to transducer element 303 may be provided via a delay module 305. Although not shown in FIG. 3, it should be appreciated that other delay modules may be provided between other transducers. Also, although just three transducers are shown in FIG. 3, it should be appreciated that many other transducer and arrays of transducers are contemplated in the embodiments.

Each of the transducers may receive the signal via a respective pulse driver. For example, a pulse driver 306 may be in communication with transducer element 302, a pulse driver 307 may be in communication with transducer element 303, and a pulse driver 308 may be in communication with transducer element 304. The transducers may be acoustic transducers that convert the signal provided by pulse generator 301 from an electrical signal to an acoustic and/or ultrasonic wave. In some embodiments, the size (physical or electrical) of the transducer elements may be sufficiently small to allow the transducer elements to effectively act as point radiators in a predetermined frequency range. The timing of the pulses provided to the transducers and thus the timing of the acoustic waves created by the transducers may be of any nature, according to the contemplated embodiments. For example, the arrangement may be a phased array whereby transmit focal points are typically located at equal radial distances from a common vertex. The transmit beams are usually located at equal angular distances from each other and may span a total of 90 degrees or more. While the transmit focus is typically located at one point along the beam, echo data is usually collected along the entire beam length starting at the vertex and ending at a point corresponding to some maximum imaging depth. At radial locations other than the transmit focal point, the transmit beam diverges with the beam becoming increasingly unfocused at radial locations furthest from the focal point.

The acoustic waves created by the transducers interrogate a particular point or target 309 within a medium. Target 309 may be of any size or dimension. In some embodiments, target 309 may be considered to be a point-reflector, such that its dimensions are relatively small compared to the wavelength of the ultrasound wave. In this embodiment, the target may be considered to effectively be a Dirac delta function in space, such that the reflected echo wave provides a substantial replica of the wave that hits and interrogates target 309.

In just one example, target 309 is some distance "D" from a center line of transducer element 303. With "c" as the speed of sound, the amount of time it takes an ultrasound wave to travel from transducer element 303 to target 309 is calculated as $T=D/c$. The distance from transducer element 304 to target 309 is D+A, so A is the difference between transducer element 304 distance to target 309 and transducer element 303 distance to target 309. The time it takes to travel the distance $\Delta$ is $\tau=\Delta/c$.

In some embodiments, it may be desirable to apply delays between the pulse generator signals and transducer elements for some purpose. For example, in one embodiment, it may be desirable to provide delays to create a more focused wavefront at a particular point, like target 309. In a focused wavefront, the ultrasound waves generated by each transmitting transducer element may sum substantially constructively at one location within the field of view (FOV) and relatively destructively at the other locations in the FOV. In this example, it may be that transducer elements 302 and 304 create their ultrasound waves first in time, followed by transducer element 303 at a time $\tau$ later. FIG. 3 captures an example of the emitted acoustic waves some time later, for example, $t<T+\tau$. These waves created by the transducers will converge and constructively interfere at the focal location, creating a pressure wave that is the coherent sum of the three transmit waves. The waves will all arrive at the focal point at time $t=T+\tau$. Typically, under normal conditions, at the other points in space, the waves will not constructively sum.

Figure 4:
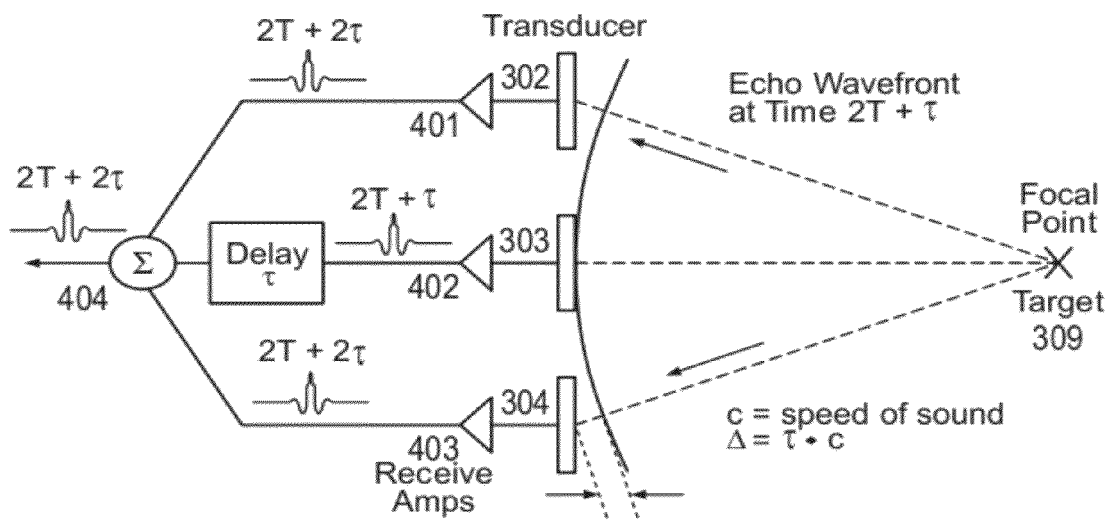
FIG. 4 is a block diagram of a system for receiving an acoustic transmit focused wave.

FIG. 4 is a block diagram of a receive beamformer system. As shown in FIG. 4, target 309 reflects the transmitted ultrasound wave back to transducers 302-304. Although transducers 302-304 are shown as being the same as the transducers that transmitted the interrogating ultrasound wave, the embodiments are not so limited. Instead, it should be appreciated that the echo wave may be received by any available transducers, including only a portion of the transmitting transducers and/or different transducers. Any combination thereof is contemplated.

As shown in FIG. 4, target 309 reflects at least a portion of the transmitted ultrasound wave back to the transducers. As a result of the smaller target dimensions, in this example, the reflected wave is substantially hemispherical. Although FIG. 4 illustrates the echo waves as sinusoidal pulses (typical of ultrasound transducers), it should be appreciated that the echo waves contemplated by the embodiments may be of any characteristic. Also, it should be appreciated that the echo waves may have any type of characteristic frequency $F_c$, that may be modulated with an envelope that may be modeled as Gaussian and/or other windowing function. For example, where $F_{bw}$ is the bandwidth of the modulation envelope, a fractional bandwidth, $F_{bw}/F_c$ may be 50% to 70% (at the −6 dB points) for typical transducers.

In this example, at a time $2T+\tau$, the reflected acoustic wave reaches transducer element 303. The transducers act to convert the acoustic wave into electrical energy. Transducer element 303 may provide the electrical energy signal to an amplifier 402 that amplifiers the electrical energy signal as required by the remainder of the system. At a later time, for example, $2T+2\tau$, the reflected wave reaches transducer elements 302 and 304.

Transducer elements 302 and 304 convert the acoustic wave into electrical energy that is amplified, respectively, by amplifiers 401 and 403. The electrical energy provided by the transducers may be either analog or digital signals. Also, the analog electrical signals may be analog and later converted to digital signals, for example, using analog-to-digital (A/D) converters (not shown). Such conversion to digital signals may be accomplished at any point in the system, as contemplated by the embodiments. Time delay 305 causes a delay in the electrical signal from amplifier 402, such that the electrical signals from the three amplifiers arrive at a summer 404 substantially simultaneously, or at least in close enough proximity of time to allow the signals to sum constructively. Such time delay may be accomplished on both analog and digital electrical signals.

Summer 404 adds the three electrical signals, and the summed signal is transmitted to further circuitry (not shown) for further processing and analysis. For example, in just one embodiment, the summed signal may have its magnitude, amplitude and/or phase sent to a processor who determines the corresponding values and converts the values into an image value (e.g., brightness). B-Mode typically refers to determining an image's brightness value based on the amplitude of the summed echo signals near a transmitted center frequency.

Another method for interrogating a medium and processing the data needed to create an ultrasound image involves synthetic transmit focusing. With synthetic transmit focusing methods, each pixel of an image may be formed from data acquired by multiple transmit events from various locations of the transducers. Generally, with synthetic transmit focusing, sequentially acquired data sets may be combined to form a resultant image.

On the transmit side of a synthetic transmit focusing system, it may be desirable to interrogate as broad an area of the medium as possible. Broad interrogation may be accomplished using many techniques.

Figures 5A, 5B, 5C:
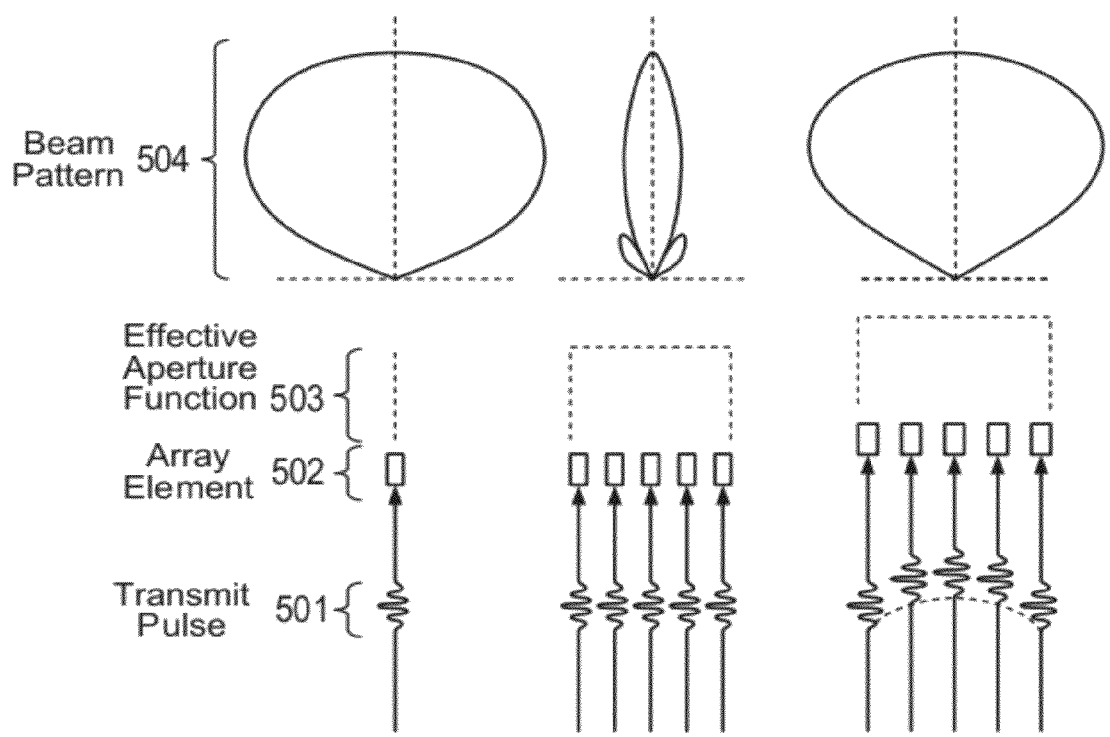
FIGS. 5A-5C provide an example of different possible configurations and techniques for providing interrogation of a medium.

FIGS. 5A-5C illustrate examples of different possible configurations and techniques for providing such interrogation. In particular, FIGS. 5A-5C provide examples of a transmit pulse or pulses 501, an arrangement or array of transducer elements 502, an effective aperture 503, and a resultant beam pattern 504. For example, as shown in FIG. 5A, sequentially providing transmit pulses a single transducer element (for example of an array of transducers) may create a broad beam pattern. Another example shown in FIG. 5B illustrates providing a series of transmit pulses each to an individual transducer at substantially the same time. Finally, as shown in FIG. 5C, providing a transmit pulse to each transducer in a certain sequence may also create a broad beam pattern. FIG. 5C provides just one example of a defocused transmit, which may permit greater signal-to-noise ratio (SNR) and better sensitivity off the center line of the transducer elements. Although the beam pattern created by FIG. 5B may not be as broad as the example in FIG. 5A or 5C, it may be sufficient in certain contemplated embodiments.

Figure 6:
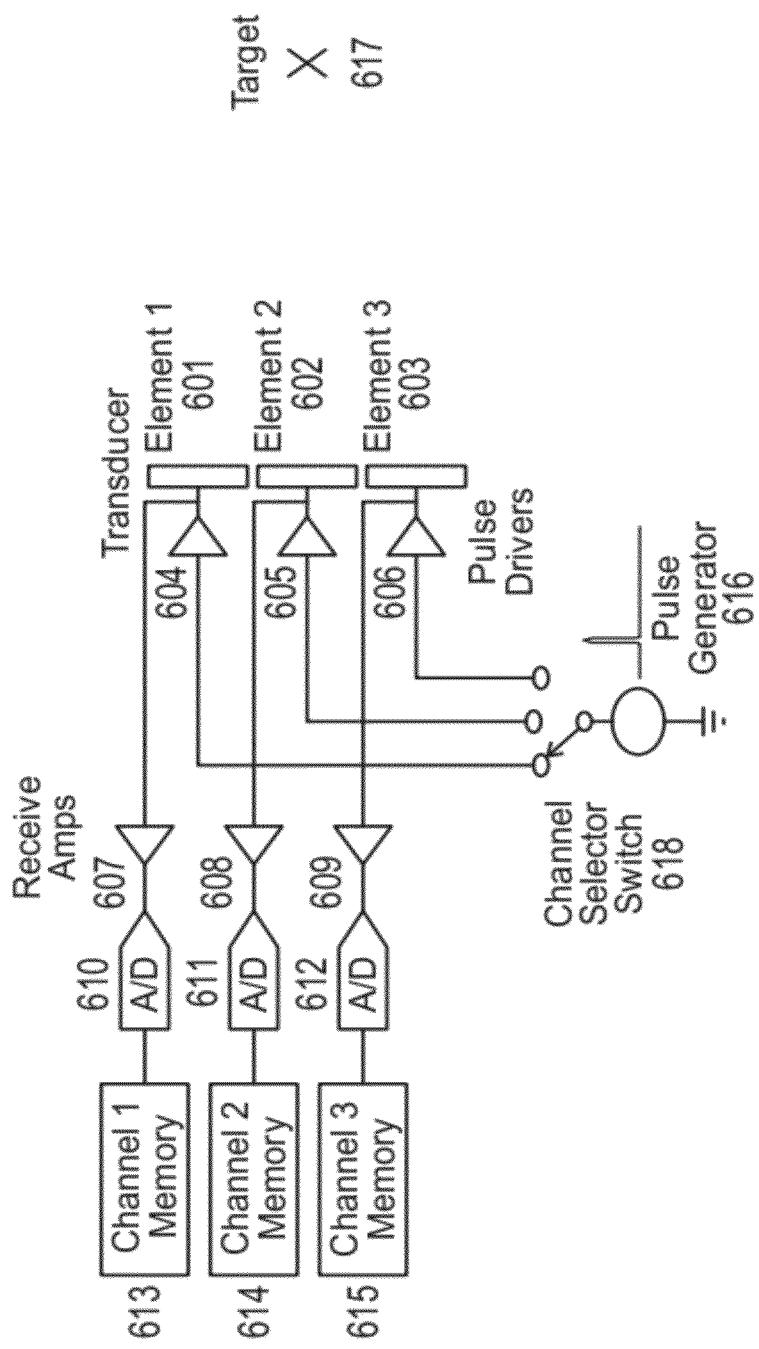
FIG. 6 is a block diagram of a synthetic transmit focus ultrasound system.

FIG. 6 is a block diagram of a synthetic transmit focus ultrasound system 600. As shown in FIG. 6, a target 617 may be interrogated by ultrasound waves transmitted from transducers 601-603. Also, the echo ultrasound waves reflected from target 617 may be received by transducers 601-603.

On the transmit side, a pulse generator 616 provides an electrical signal to a channel selector switch 618. Channel selector switch 618 may be programmed to direct the signal from pulse generator 616 to each of pulse drivers 604-606 (and then onto transducers 601-603) at any one time. As a result, channel selector switch 618 may provide one of many sequenced signals to the transducer elements. Once a signal is sent to a transducer an acoustic or ultrasound wave is created.

The ultrasound wave may hit target 617 or another part of the medium. Certain parts of the ultrasound wave may be reflected to create reflected echo waves. Certain parts of the reflected ultrasound waves may return to one or more of transducer elements 601-603 and/or to other transducer elements (not shown). The reflected echo wave or waves may be converted by transducer elements 601-603 or the other transducer elements into an electrical signal. The electrical signal may be provided to one of receive amplifiers 607-609, depending upon which transducer element the ultrasound wave is received. Each amplifier 607-609 may provide the electrical signal to a respective A/D converter 610-612, which converts the analog signals from each receiver amplifier 607-609 to a digital signal.

The digital signal may then be stored in a respective channel memory device 613-615. By storing digital data in channel memory devices 613-615, subsequent processing may be performed on the data. For example, in just one embodiment, the digital data may be processed to identify the characteristics of target 617 or of any other location in the medium. Because the digital data is stored with its corresponding parameters, the digital data may be used to identify any point in the medium. This processing is not limited to being performed immediately after receiving the digital data, but may be conducted at some time substantially after the digital data is received in channel memory devices 613-615.

In some embodiments (e.g., a wireless probe), it may be desirable to operate certain components intermittently. This may be desirable, for example, to conserve power consumption and/or to reduce overall maintenance. For example, in some embodiments, A/D converters 610-612 may be turned off and on as needed. For example, A/D converters 610-612 may operate just long enough so that energy from a particular transducer element 601-603 has sufficient time to propagate out to the desired portions of the medium, reflect back from these portions, and return to a transducer element 601-603. After this is accomplished in some embodiments, A/D converters 610-612 may be disabled and/or placed in a low-power state. In other embodiments, (e.g., wired probe that receives power from a main unit) it may not be necessary to turn off A/D converters 610-612, or any other component.

FIG. 7 provides an example illustration of signals transmitted from each of transducer elements 601-603 and received back on respective transducer elements 601-603 and stored in channel memory devices 613-621. It should be appreciated that although just three transducer elements and channel memory devices are described, either one or many of such components may be used. Three of such devices are described merely to provide clarity of explanation with brevity.

FIG. 7 illustrates each of transducer elements 601-603 separately transmitting an ultrasound wave that is received on each of transducer elements 601-603. For example, as shown in FIG. 7, transducer element 601 may transmit an ultrasound wave that is received by transducer element 601 and stored in channel memory device 613 as echo wave 701. Similarly, for example, transducer element 601 may transmit an ultrasound wave that is received by transducer element 602 and stored in channel memory device 614 as echo wave 702. In addition, transducer element 601 may transmit an ultrasound wave that is received by transducer element 603 and stored in channel memory device 615 as echo wave 703. Also, with respect to an ultrasound wave transmitted from transducer element 602, echo wave 704 may be stored in channel memory device 616, echo wave 705 may be stored in channel memory device 617, and echo wave 706 may be stored in channel memory device 618. With respect to an ultrasound wave transmitted from transducer element 603, echo wave 707 may be stored in channel memory device 619, echo wave 708 may be stored in channel memory device 620, and echo wave 709 may be received on channel memory device 621.

In this one example embodiment, there may be nine echo waves 701-709. Echo waves 701-709 each serve as a sequence of data points, representing reflection of a transmitted ultrasound wave from various points in the medium. For example, each data point may be stored in a predetermined location, so as to later identify the data point for subsequent processing. Each data sequence is acquired by sampling the reflected echo waves 701-709 beginning at a time 0 and ending at a time greater than $2T+2\tau$. If a distance from target 617 to transducer element 602 is D, then a distance from transducer element 601 to target 617 may be considered to be $D+\Delta$. A round trip distance (i.e., from transducer element 601 to target 617 and back to transducer element 601) may be represented as $2D+2\Delta$, and a corresponding round trip time may be considered to be $2T+2\tau$.

For example, for an ultrasound wave transmitted from transducer element 601 and received by transducer element 602, echo wave 702, a peak value 710 may be found at time $2T+\tau$. Similarly, as shown in FIG. 7, the echo pulses add coherently for the round trip distances and/or times for the other transmit/receive transducer element pairs. Also, in some embodiments, the coherent adding may not occur at any other point in space. As a result, the received data points may be synthetically focused or added mathematically by, for example, superposition of the echo data. This may be accomplished in addition to or in lieu of analysis and processing of physical acoustic pressure summation in the image field.

As a result of not simply separating transmit and receive focus, it is possible to also process transmit and receive delays to synthesize a round-trip focus at any point of interest. Yet, it should be appreciated that in some embodiments, it may be desirable to also decompose the focusing into transmit and receive components in addition to or in lieu of the synthetic transmit focusing techniques. For example, it should be appreciated that it may be desirable to treat a one-way time from a transmit transducer element to a target as transmit focusing, and treat a one-way time from the target to the receive transducer element as receive focusing.

Also, synthetic transmit focusing used with or without acoustic transmit focus techniques may permit improved transmit focus throughout the image field. For example, because transmit focusing may at least in part be created via mathematical summation, focusing may be performed at a multitude of depths within the medium (e.g., each image pixel location), instead of or in addition to a limited number of discrete focal points. This may be accomplished, in some embodiments, by computing round trip distances and/or times for any point in the image field and summing or processing the data samples corresponding to that point from many transmit/receive combinations to synthesize a focus at the particular point. For example, in just one embodiment a focus may be synthesized for a particular point in the medium by computing a round trip distance and/or time from each transmit transducer element to the target and back to each receive transducer element (e.g., for three transmit transducer elements and three receiver transducer elements, there may be nine transmit/receive pairs as shown in FIG. 7). A processor may then extract from a predetermined database and/or data store (e.g., channel memory devices 613-621) certain data points that correspond to those round-trip distances and/or times. These data points may then be summed, for example, or processed in some way to permit image formation.

Synthetic transmit focusing and/or partial synthetic transmit focusing techniques may require additional considerations when substantially significant image motion is present. Consequently, in some embodiments, the synthetic transmit focusing or partial synthetic transmit focusing techniques may use methods and techniques to track movement of the medium. For example, in embodiments where the transmit transducer elements fire sequentially, the echoes from targets in the medium may be collected over a period of time. If the targets move during the time period, the distance and/or time data of the echo waves may be changed from one interval to the next. As a result, spatial and contrast resolution of the image may be degraded. Although movement of the medium does not minimize the utility of the suggested techniques, it may be desirable in some embodiment to track, and perhaps even correct for such movement. Alternatively, some embodiments may restrict the medium such that movement does not occur. Also, some embodiments may decrease the acquisition interval and reduce the time of acquisition, thus reducing the likelihood of movement during the shorter acquisition period. Also, in some embodiments a number of transmit elements may be reduced in response to detected motion, thus reducing the acquisition time and the effect of motion on the resulting image.

Some embodiments may quantify signal-to-noise ratio (SNR). For example, assuming M receive transducer elements and N transmit transducer elements, and a receive channel noise floor of $e_n$; if the system is using acoustic transmit focusing techniques, then the acoustic echo information from the selected beam direction may be acquired in a single transmit event, so the receive beamformer has $M*e_n$ of noise in its output. This is due in part to each receive transducer element contributing its noise floor to the output sum. With the synthetic transmit focusing techniques, there is $M*N*e_n$ of noise in the output, because each receive transducer element adds noise to a data record each time echo data is captured from a transmit transducer element. In other words, each receive transducer element runs N times (e.g., sequentially) to capture the data from the transmit transducer elements. This may be different than some embodiments that use acoustic transmit focusing techniques, where the signals from the transmit transducer elements are returning at substantially the same time, and therefore may be captured in substantially one pass.

It should be appreciated that some embodiments contemplate the use of a reduced redundancy array of transducer elements. For example, an N-element phased array system typically has $N^2$ transmit/receive transducer element combinations. In some embodiments, almost half of the combinations may be redundant or otherwise unnecessary. In the embodiments that employ a reduced redundancy array of transducer elements, certain transmit/receive transducer element combinations may be ignored or otherwise decimated in some manner.

Reduced redundancy arrays may be accomplished using a number of techniques. For example, some embodiments may employ transmitting from a group of transmit transducer elements substantially simultaneously, instead of or in addition to using a single element for each transmit event. Also, in some embodiments, increasing the spacing of the transmit transducer elements and/or element groups reduces a number of transmit events for each image frame. This may permit a greater frame rate and/or a reduced computation rate in the image processing. Some embodiments may reduce redundancy by turning off certain transmit transducer elements. This may be accomplished on successive transmit events, where each event is constrained to elements nearby the transmitted group. Those skilled in the art may refer to such techniques as Multi-element Synthetic Aperture Focusing (MSAF). Other sparse array and synthetic focusing methods are also contemplated embodiments.

In some embodiments the transmit/receive transducer elements may be used in groups that may or may not be overlapping. Overlapping transmit/receive transducer element groups may facilitate the use of lower voltages to drive the transmitter transducer elements. Alternatively, in some embodiments, using the same voltage to drive a group of transmitter transducer elements may provide greater transmit power than may be achieved by driving a single element, for example.

Synthetic transmit focus techniques may allow some embodiments to reduce a number of required element transmit events per image frame. Such a reduction may allow for a relative increase in the power efficiency, and therefore improve self-powered considerations, like the operational time of a battery and/or battery size.

Some embodiments may use a single transmit transducer element to create perhaps a less directional ultrasound wavefront, and/or a wavefront that better approximates a point source (e.g., a hemispheric wavefront). As discussed with reference to FIGS. 5A-5C, an element group fired substantially simultaneously may produce a plane wave. Yet, in some embodiments, it may be desirable to have either a plane wave and/or a reasonably hemispheric wave. For example, the hemispheric wave may permit the received echo waves to interrogate a larger portion of the medium. For a group of transducer transmit elements, a defocused wavefront may emulate a point source that is synthesized by proper defocusing of the transmit beam. This technique may permit greater transmitted energy with lower drive voltages while also producing a less directional wavefront.

Figure 8:
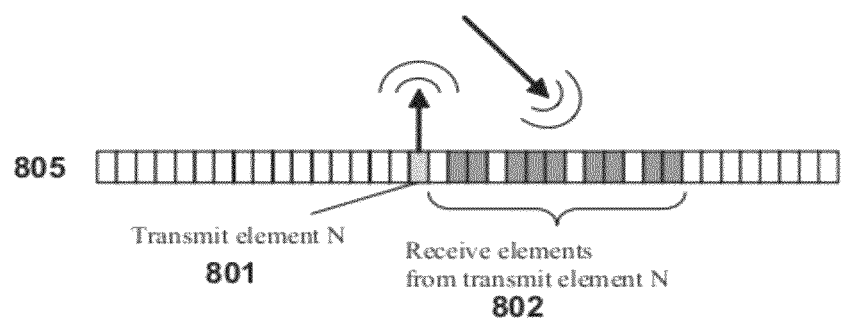
FIG. 8 illustrates just one example technique of decimating a number of transducer elements that receive an echo ultrasound wave.

FIG. 8 illustrates just one example technique of decimating the number of transducer elements 805 that receive the echo ultrasound wave. As shown in FIG. 8, a transmitting transducer element 801 may transmit from a single transducer element and be received on less than a total number of available transducer receiver elements 802. In the example of FIG. 8, there are nine receive transducer elements 802 (shown shaded) available to receive the reflected echo wave. In some embodiments, the available receiving transducer elements may vary depending upon a particular transmitting transducer element and/or the location of the target, for example. The receive transducer elements may be changed to a different pattern of elements, for example, to accommodate the transducer edges.

Image formation involving acoustic transmit focus techniques involves the use of a scan line that often is perpendicular to the tangent of transmitting transducer array. The scan line may also be steered at different angles using phased array techniques, well known to those skilled in the art. Typically, the scan lines are acquired sequentially beginning at one end of an image frame and continuing throughout the frame. However, in some embodiments, samples along the scan lines do not necessarily align with the pixels on a Cartesian grid. With respect to a phased array system, the scan line sample density may be non-uniformly distributed throughout the image frame with a higher density of samples occurring in the near-field. Scan lines may then be processed to allow conversion to an image Cartesian format. For example, with B-Mode imaging, well known to those skilled in the art, processing may involve magnitude detection, log compression, spatial and temporal filtering, for example. A two-dimensional interpolation method (e.g., bilinear interpolation) may then be performed to convert to the Cartesian image format.

The disclosed embodiments contemplate using image processing techniques convenient for acoustic transmit focusing. Also, with respect to synthetic transmit focusing methods, the disclosed embodiments contemplate using additional image processing techniques. For example, in some embodiments, synthetic transmit focusing techniques may form image pixels directly and/or indirectly from collected data samples. One such technique employs coherent summation of the signal samples from each transmit/receive pair of array elements for each pixel.

With acoustic transmit focusing, it may be that samples along the beam may not line up with image pixels. As a result, interpolation of the beam samples may be required to compute and determine the precise pixel value. In some embodiments, the beam sample may align with the image pixel and thus no interpolation may be necessary.

With synthetic transmit focusing techniques, each pixel may be able to be formed from the collected data values determined for each part of the medium. In particular, with synthetic transmit focusing because each pixel has its own receive path and is formed by combining signals from multiple transmit transducer elements and receive transducer element pairs, it may not be necessary to conduct scan conversion or processing. In other words, because synthetic transmit focus techniques provide both transmit and receive dynamic focusing capability, the formation of the pixels of the corresponding image may be determined directly from the roundtrip paths from transmit transducer elements to the target (or pixel) and back to receive transducer elements. Therefore, forming a pixel on an image derives from synthetic transmit focusing because each pixel can be ideally focused on both transmit and receive.

Some embodiments may provide acoustic transmit focusing techniques and synthetic transmit focusing techniques simultaneously for combination modes that may require both techniques such as color flow, for example. Some embodiments may alternate between acoustic transmit focusing and synthetic transmit focusing techniques dynamically and, perhaps, on a periodic basis. A variety of other combinations of acoustic transmit focusing and synthetic transmit focusing techniques are contemplated by the disclosed embodiments.

In some embodiments, received echo signals may be substantially simultaneously acquired from all, or part, of the transducer element array, for example, on each transmit event. Some embodiments may create each pixel by time and amplitude adjustments for each transmit and receive transducer element pairing. Also, time delay resolution may be improved by using interpolation techniques among the received data samples (e.g., linear interpolation between sample pairs in Cartesian space and/or polar space, spline, non-linear interpolation, and the like).

Although, it may not always be possible to accomplish such direct pixel formation with acoustic transmit focusing techniques, it should be appreciated that such pixel forming techniques may be used. Also, such pixel forming techniques may be used in combination with data sample interpolation techniques. In addition, with synthetic transmit focus methods, both pixel forming techniques and interpolation techniques may be used to create an image from the data points.

In some embodiments, it may be that all of the available transmit/receive transducer element pairs are used to create the pixel. The following equation is one example of how to determine the data sample index (n) for a single transmit/receive transducer element pair:

$$n = F_S \times c \times \{SQRT((X_P-X_T)^2+(Y_P-Y_T)^2)+SQRT((X_P-X_R)^2+(Y_P-Y_R)^2)\}$$

The variables $X_P$ and $Y_P$ are the coordinate dimensions of the pixel to be formed. The variables $X_R$ and $Y_R$ are the coordinate dimensions of the receive transducer element and the variables $X_T$ and $Y_T$ are the coordinate dimensions of the transmit transducer element or virtual center of a group of transmit elements. The variables $F_S$ and c are the data sampling rate and the speed of sound in tissue (typically 1540 m/s), respectively. This calculation may be performed for each transmit/receive element transducer pair contributing to each pixel. Note that for a linear array, $Y_R$ is zero. The disclosed embodiments also contemplate that such synthetic focusing techniques can be readily extended to three dimensions, as is well understood by those skilled in the art.

The first part of the equation relates to dynamic transmit focusing and the second part dynamic receive focusing. In the case of a fixed acoustic transmit focus system, the origin of the transmit beam is fixed at ($X_T$, $Y_T$) for samples and/or pixels formed from that transmit event. If receive beams are formed, the equation simplifies further because the distance along the beam vector is merely proportional to the sample count of the vector. Therefore, for an acoustic transmit focusing system, the equation above reduces to the following, with D representing the radial distance along the beam:

$$n = F_S \times S \times \{D+SQRT((X_P-X_R)^2+(Y_P-Y_R)^2)\}$$

Note that in this case, $X_P$ and $Y_P$ are the coordinate dimensions of samples along the beam. If the transmit and receive beam origins are the same, the equation may be expressed as follows with $\Theta$ representing the beam angle relative to the horizontal axis along the array dimension:

$$n = F_S \times S \times \{D+SQRT((C \times \cos(\Theta)-X_R)^2+(D \times \sin(\Theta)-Y_R)^2)\}$$

For T transmitter elements and R receiver elements, the number of such calculations per output pixel in a synthetic transmit focusing system may be proportional to the product of T and R. Also, a number of calculations required in an acoustic transmit focusing system to compute samples along the beam may be proportional to R.

In some embodiments, the computing complexity necessary to accomplish the synthetic transmit focusing techniques may be greater. For example, consider a linear transducer array probe with N transducer elements. If each column of pixels in the image is made to align with the center of each transducer element in the array, there may be as many beams as transducer elements. With respect to synthetic transmit focusing techniques, transmitting on the transducer elements in the array individually may require N transmissions to create an image frame. With respect to acoustic transmit focusing techniques, it may be assumed that an equal number of transducer transmissions may be required if there is one transmission per beam. If beam samples are made to align with image pixels, signals from R receive elements may be combined to form each sample or pixel per beam.

Therefore, for the synthetic transmit focusing techniques, N×R signal combinations per pixel may be required, and thus in just some embodiments the computational requirements of synthetic transmit focusing system may be N times greater than the acoustic transmit focusing system. Due to the potential increased computational burden of synthetic transmit focusing, in some embodiments, it may be desirable to select and limit the number of transmit/receive transducer element pairs (T×R) necessary to form each pixel. This may be accomplished by aperture restricting criteria known in the art as f-number and/or acceptance angle. In addition, maximum transmit/receive aperture sizes that are smaller than the full array may be enforced.

Some embodiments may use interpolation (e.g., linear and/or sample) as well as demodulation techniques, like using quadrature-sampled baseband data with phase adjustment. It should be appreciated that these techniques may be used with synthetic transmit focusing techniques, acoustic transmit focusing techniques, and any combinations thereof. Also, these example techniques are not inclusive, but it should be appreciated that alternative methods of demodulation and interpolation, perhaps with appropriate phase adjustment, are contemplated by the disclosed embodiments. In addition, compensation techniques may be used to preserve coherence.

In some embodiments, echo signals received by the receive transducer elements may be characterized by a carrier frequency Fc (with an angular frequency of Wc=2πFc), modulated by a pulse envelope where the fractional bandwidth is typically 50% to 70% (at −6 dB). In some embodiments, it may be desirable to quadrature demodulate the received echo signals to extract a modulation envelope. With quadrature demodulation, resulting baseband analytic pair signals (e.g., I+jQ) may include information from the original modulation signal. As a result, having the demodulation frequency, and the modulation signal (I+jQ), permits the echo signals to be recreated, which may be desirable in some embodiments.

In some embodiments, for example where a lower data rate is desired, baseband sampling techniques may be employed. In some embodiments, if the baseband analytic pair includes the modulation information that was in the original echo signals, the data may be used for acoustic transmit focusing and/or synthetic transmit focusing techniques, instead of, or in addition to, recreating the original echo signals before beamforming. In either case, in using the baseband analytic pair with respect to acoustic transmit focusing, partial acoustic transmit focusing, and/or synthetic transmit focusing, the data consequent from the demodulation process that is included with the baseband signals may be accounted for in some embodiments. In addition, in some embodiments, carrier frequency information may be accounted for as well. Accounting for these additional considerations may be accomplished in any of the disclosed embodiments, including acoustic transmit focusing and synthetic transmit focus techniques, for example.

Considering the example described with respect to FIG. 7, round-trip time from transducer element 602 to the target and back to transducer element 602 is 2T, and round-trip time from transducer element 602 to the target and back to transducer element 601 is 2T+τ. As discussed, the signals will have phase coherence and add constructively. Using this example and applying it to demodulation prior to acoustic transmit focusing and/or synthetic transmit focusing, may provide the following: x(t)=M(t)Fc(t), where x(t) is the round-trip impulse response of the transducer elements, M(t)=Mi(t)+jMq(t) is the modulation envelope of the round-trip impulse response, and C(t)=sin(Wc t) where Wc is the characteristic center frequency of the particular transducer element. It should be appreciated that a round trip impulse response of the transducer element may be two passes through the element's one-way impulse response. Therefore, a round-trip impulse response may be the self-convolution of the one-way impulse response. The echo signals e(t) from the target can be written as follows:

Echo from transmit on transducer element 602, received on transducer element 602:

$$e_{22}(t) = M(t-2T)C(t-2T),$$
$$= Mi(t-2T)\sin(Wc(t-2T)) +$$
$$jMq(t-2T)\sin(Wc(t-2T))$$

Echo from transmit on transducer element 602, received on transducer element 601:

$$e_{21}(t) = Mi(t-(2T+\tau))\sin(Wc(t-(2T+\tau))) + jMq(t-(2T+\tau))\sin(Wc(t-(2T+\tau)))$$

As discussed, quadrature demodulation may be used on the received echo signals. In these embodiments, using quadrature demodulation, each echo signal may be multiplied by an in-phase and a quadrature sine wave to get two baseband components. For the echo from transmit on transducer element 602, received on transducer element 602, the following:

$$d_{i22}(t)=\sin(Wct)e_{22}(t)=\sin(Wct)Mi(t-2T)\sin(Wct-Wc(2T))+j\sin(Wct)Mq(t-2T)\sin(Wct-Wc(2T))$$

and $$d_{q22}(t)=\cos(Wct)e_{22}(t)=\cos(Wct)Mi(t-2T)\sin(Wct-Wc(2T))+j\cos(Wct)Mq(t-2T)\sin(Wct-Wc(2T))$$

Where the analytic baseband signal $d_{22}(t)=d_{i22}(t)+j\, d_{q22}(t)$
Using the trigonometric relations $\sin(a)\sin(b)=\frac{1}{2}[\cos(a-b)-\cos(a+b)]$ and $\cos(a)\sin(b)=\frac{1}{2}[\sin(a+b)-\sin(a-b)]$, provides:

$$d_{i22}(t)=\tfrac{1}{2}\{Mi(t-2T)[\cos(Wc(2T))-\cos(2Wct-Wc(2T))]+jMq(t-2T)[\cos(Wc(2T))-\cos(2Wct-Wc(2T))]\}$$

In some embodiments, it may be desirable to look just at the baseband component. In these embodiments, it may be desirable to filter the $\cos(2Wct-Wc(2T))$ term, which represents a twice frequency (2Fc) component, and setting this term to zero, provides:

$$d_{i22}(t)=\tfrac{1}{2}\{Mi(t-2T)\cos(Wc(2T))+jMq(t-2T)\cos(Wc(2T))\}$$

Using the other substitution and lowpass filtering for the quadrature component gives the following:

$$d_{q22}(t)=\tfrac{1}{2}\{Mi(t-2T)\sin(Wc(2T))+jMq(t-2T)\sin(Wc(2T))\}$$

and the analytic baseband signal is:

$$d_{22}(t) = \frac{1}{2}\{[Mi(t-2T)+jMq(t-2T)*$$
$$[\cos(Wc(2T))-j\sin(Wc(2T))]\}$$
$$= \frac{1}{2}M(t-2T)e^{jWc2T}$$

This expression provides the original envelope information (e.g., M(t−2T)), and also includes a residual demodulator phase term ($e^{jWc2T}$). The residual demodulator phase term is present because the phase of the demodulator signals at that point in time phase rotates the envelope function by some amount. In other words, the phase rotation is essentially random because there typically is no relationship between the round-trip times and the demodulator signal phase. In some embodiments, the random phase rotation may be acceptable because in those embodiments, phase term may not impact the imaging process. For example, with respect to beam-formed techniques, B-Mode techniques that respond to amplitude, and Doppler mode techniques that analyze phase change with respect to time, absolute phase values may not be required.

Similarly, for the echo from transmit on transducer element 602, received on transducer element 601, the following:

$$d_{21}(t)=\tfrac{1}{2}M(t-(2T+\tau))e^{jWc(2T+\tau)}$$

Accomplishing synthetic transmit focus techniques with the baseband components advances the $d_{22}(t)$ signal by 2T, and advances the $d_{21}(t)$ signal by 2T+τ. Summing these terms along with contributions from the other transmit/receive transducer element pairs for the target, provides the following:

$$pd=\Sigma_{n=1\ldots 3}\Sigma_{m=1\ldots 3}d_{nm}(t_{round\;trip})=d_{21}(2T+\tau)+d_{22}(2T)+\text{seven other terms}.$$

The variable pd represents pixel data summation over the transmit/receive transducer element pairs at the target.

In the synthetic transmit focus example, the demodulator phase term may represents a phase error between the two signals that needs correction or compensation, in some embodiments. This is due, in part, to the fact that modulation envelope M(t) components are phased aligned, but not the demodulator phase terms, because the demodulator phase term may no longer be a function of time.

The disclosed embodiments contemplate many ways to compensate for the demodulator phase term. One example technique for compensating for demodulator phase term contemplates applying an additional phase rotation term to $d_{21}(t)$ to account for a later arrival time of the signal on transducer element 601. By considering the difference in the times of flight of the two signals, it may be appropriate to apply a phase rotation of $e^{-jWc\tau}$ to $d_{21}$ to achieve phase alignment of $d_{21}$ and $d_{22}$. In some embodiments, a similar phase adjustment may be applied to the other transmit/receive transducer element pairs to phase align them to $d_{22}(t)$ before summing to get pd.

In implementing the above technique, in some embodiments the phase rotation correction that may need to be applied to the baseband signals before summation may need to be the modulo-$2\pi$ remainder of the total phase error. For example, assuming the same signals derived for $d_{nm}(t)$ as above, and sampling at a demodulator frequency with a fractional bandwidth of the echo signals less than 100%, the demodulated (baseband) signal bandwidth may be less than ½ the demodulator frequency. Therefore, the signals may be adequately sampled, at least in accordance with Nyquist criterion, well known to those skilled in the art. If a sample clock is chosen to sample at zero phase of the demodulation signal, then the D samples may have zero phase relative to the demodulator signal. Therefore, calculating the pixel data sum pd using the nearest-neighbor samples (i.e., sample nearest to the actual round-trip time for that transmit/receive transducer element pair) may eliminate any differential demodulator phase error between signals in the summation, because the modulo-$2\pi$ phases of the data points in the summation would be zero.

In some embodiments, where interpolation between adjacent samples is used, it may be advisable to use a "fractional time" between samples to determine a quantity of additional phase shift to apply to equalize the interpolated sample to zero phase. The modulo-$2\pi$ remainder of the phase error is $2\pi$ times the "fractional time" between actual samples, and the sampling process gives a phase reference of the demodulator, the phase is at zero at the sample times, and it traverses $2\pi$ between the samples.

A sampled version of the demodulated echo signals may be represented as $ds_{nm}$, with $ds_{nm}(t_0)$ as the digitally sampled demodulated echo signal falling at (continuous time) $t_0$, and ignoring quantization effects provides $ds_{nm}(t_0)=d_{nm}(t_0)$. Assuming that one of the sample times is at 2T, then $ds_{22}(2T)$ is one of the stored samples from transducer element 602. Because the time 2T is at the sample time, the demodulator phase at that moment is an integer multiple of $2\pi$. The phase term of $d_{22}(2T)$ is $e^{jn2\pi}=1$, the expression for $d_{22}(2T)$ becomes:

$$ds_{22}(2T)=d_{22}(2T)=½[Mi(0)+j\,Mq(0)], \text{ with } M(0) \text{ decomposed into analytic pair}$$

Evaluating $d_{21}(2T+\tau)$ by decomposing i into an integer number of sample times and a remainder part, as follows:

$n_\tau=\text{int}(\tau Fc)$ where int( ) denotes the integer part operator then $\tau_{int}=n_\tau/Fc$ is the time that corresponds to an integer number of sample cycles.

and:

$\tau_{rem}=\tau-n_\tau/Fc$ is the time remainder

So that:

$$\tau=\tau_{int}+\tau_{rem}$$

Defining fractional time $\tau_{frac}=\tau_{rem}Fc$; $0\leq\tau_{frac}<1$, where $\tau_{frac}$ is the "fractional time" or fraction of the sample interval between these samples where the actual time of flight falls, the expression can be written for $\tau$ as follows:

$$\tau=\tau_{int}+\tau_{frac}/Fc$$

The sample times substantially immediately before and substantially immediately after the time $2T+\tau$ are:

$$t=2T+\tau_{int} \text{ and } t=2T+\tau_{int}+1/Fc$$

substituting $\tau_{int}=\tau-\tau_{rem}$ gives $2T+\tau_{int}=2T+\tau-\tau_{rem}$ and $$2T+\tau_{int}+1/Fc=2T+\tau+(1/Fc-\tau_{rem}) \text{ so:}$$

$$ds_{21}(2T+\tau_{int})=d_{21}(2T+\tau-\tau_{rem})=½[Mi(-\tau_{rem})+jMq(-\tau_{rem})] \text{ and}$$

$$ds_{21}(2T+\tau_{int}+1/Fc)=d_{21}(2T+\tau+(1/Fc-\tau_{rem}))=½[Mi(1/Fc-\tau_{rem})+jMq(1/Fc-\tau_{rem})]$$

Again, the phase terms are eliminated because the phase is a multiple of 2T at the sample points.

Using linear interpolation between the samples gives an approximation of the I and Q components of $d_{21}(2T+\tau)$. Also, applying a negative phase shift proportional to the fractional time interpolation cancels the additional phase rotation from the differential time component $\tau$. The interpolated (computed) value result is $ds_{21\,interp}(2T+\tau)$ is as follows:

$$ds_{21\,interp}(2T+\tau)=[\tau_{frac}(ds_{21}(2T+\tau_{int}+1/Fc))+(1-\tau_{frac})(ds_{21}(2T+\tau_{int}))]e^{-j2\pi\tau_{frac}}$$

Notably, the expression varies as a function of $\tau_{frac}$ and the two samples. The linear interpolation into the I and Q components of the A/D samples yields:

$$ds_{21\,interp}(2T+\tau)\approx¼[\tau_{frac}Mi(1/Fc-\tau_{rem})+(1-\tau_{frac})Mi(-\tau_{rem})+j\tau_{frac}Mq(1/Fc-\tau_{rem})+j(1-\tau_{frac})Mq(-\tau_{rem})]e^{-j2\pi\tau_{frac}}$$

The expression shows the sample times and constituent signal components from the input signal that are represented in the interpolated data point. Forming the pixel data sum provides:

$$pd=\Sigma_{n=1\ldots3}\Sigma_{m=1\ldots3}d_{nm}(t_{round\,trip})=d_{22}(2T)+ds_{21\,interp}(2T+\tau)+7 \text{ other interpolated terms.}$$

There is no loss of generality by assuming that 2T was a sample time, because the other terms in the expression for pd need to be interpolated to align with this arbitrary phase choice. The phase of the demodulator signals is essentially random with respect to any given pixel location on the screen for any given transmit/receive transducer element pair because the round-trip time for each transmit/receive transducer element pair to each pixel in the image area may be different. In other words, the demodulator signal phase typically does not align precisely with more than one sample point for one transmit/receive transducer element pair at a pixel location in the image area. In some embodiments, arranging the demodulator signals may yield an advantage because interpolation and phase adjustment typically will be done on many samples used to create the pixel data.

For linear interpolation, the above may be decomposed into an operation on each of the adjacent sample points. For example, for the A/D sample point prior to the round-trip time, multiplication of the data point is by the factor $(1-\tau_{frac})$ $e^{-j2\pi\tau_{frac}}$, and for the data point following the round-trip time, multiplication of the data point is by the factor $(\tau_{frac})$ $e^{-j2\pi\tau_{frac}}$.

In some embodiments, it may be desirable to convert to Cartesian notation, for example, to implement in conventional multiply-accumulators (MACCs). Generalizing the resulting operations on the sample data as a series of complex multiply-accumulations to form the pixel data point, as follows:

$$pd = \Sigma_{n=1\ldots3}\Sigma_{m=1\ldots3}\Sigma_{t-,t+}ds_{nm}(t)$$

t− and t+ refer to the sample points preceding and following the computed round trip time.

$ds_{nm}(t)$ may be expressed as the complex multiplication $(a+jb)(d_i(t)+j\,d_q(t))$, where the term $(a+jb)$ is the Cartesian conversion of the fractional time weighting and phase correction factor and the terms $d_i(t)$ and $d_q(t)$ are the in-phase and quadrature signal components at time (t) as defined previously. For example, for the data sample from time t+, $$a = \tau_{frac}\cos(-2\pi\tau_{frac}) \text{ and } b = \tau_{frac}\sin(-2\pi\tau_{frac})$$

And for the data sample from time t−, $$a = (1-\tau_{frac})\cos(-2\pi\tau_{frac}) \text{ and } b = (1-\tau_{frac})\sin(-2\pi\tau_{frac})$$

In some embodiments, each complex multiplication may require four multiply-accumulate (MACC) operations. Therefore, linear interpolation between samples with phase adjustment may require as many as 8 MACC operations per transmit/receive transducer element pair in the pixel summation. Also, coefficients a and b may include amplitude weighting to correct for signal path attenuation and element factor and/or to achieve a desired array apodization. These factors may impact the system's point spread function, which may be fine-tuned by appropriate amplitude weighting of the signals from each element for a given point in space (i.e., per pixel). In some embodiments, amplitude weighting may be used to adjust the point spread function for each pixel individually, for example. Also, some embodiments may use linear interpolation on quadrature-sampled baseband data with the described phase adjustment technique. Of course, it should be appreciated that the embodiments are not so limited and that various other methods of demodulation and interpolation with appropriate phase adjustment are contemplated by the disclosed embodiments.

Certain embodiments may accommodate other types of distortions. For example, motion of the target or medium may introduce a form of phase distortion. These motion or movement errors may be due to the relatively large time interval over which the data is acquired and coherently combined. Typically, the degree of distortion may be proportional to the rate of motion and the length of the acquisition time interval. One such example of a system that collects the data over a large time interval is the synthetic transmit focus technique. This distortion may be in addition to the phase distortion discussed.

In some embodiments, the motion distortion may be accommodated or corrected using a variety of techniques. For example, reducing a redundancy in an array reduces a number of transmit events necessary to acquire a frame of data, and thus mitigates the likelihood of movement. Constraining the subset of transmit and/or receive transducer elements to a subset of the array may also reduce phase distortion due to motion, albeit perhaps at the expense of reduced lateral resolution and SNR in some embodiments.

Decimating or reducing certain ultrasound transducers from receiving and/or transmitting ultrasound waves also may reduce transmitted data bandwidth. Such reduction may be accomplished on beamformed, partially beamformed and non-beamformed techniques. Also, by reducing a data at the beginning of the system, further reductions may be achieved, like memory and processing concerns. The decimation of the ultrasound transducers may be accomplished based on a number of considerations, like a region of interest, where the region of interest is a function of a displayed image. Also, the decimation may be based on a display resolution of an image frame, a rate of the transmission of the digital data, and a displayed region of interest of the medium. The decimation may be varied as a function of a capability of a remote unit, quality of transmission of digital data, quantity of errors in transmission of digital data, and availability of power, for example.

Also, correcting phase errors in Multi-element Synthetic Aperture Systems, well known to those skilled in the art, using cross-correlation processing also are contemplated by the disclosed embodiments. Such cross-correlation techniques may correct for phase errors due to either tissue motion and/or to tissue inhomogeneities. In some embodiments, adaptive correction may require greater computational complexity. In some embodiments, it may be desirable to reduce such complexity while still providing correction. One technique of reducing the complexity may be to constrain the correlation to a region of interest. This region of interest may be determined, for example, by a user. For an image that is relatively stationary and/or homogeneous, and has small regions of motion, such a technique may be satisfactory in some embodiments.

Other target and/or tissue motion may occur due to operator movement and may be relatively intermittent. This motion may be corrected and/or accommodated by detecting the presence of motion, quantifying it by a "motion factor", and adapting to it by changing acquisition parameters. Such changing acquisition parameters may trade off image quality for acquisition speed, in some embodiments. For example, such changing acquisition parameters may include adjustment of image acquisition parameters such as maximum transmit or receive aperture size, f-number, acceptance angle, aperture sparsity, etc. It should be appreciated that the motion factor may also be used to adjust non-coherent processing parameters such as frame averaging or persistence commonly applied to detected B-Mode image data. While in some embodiments not as susceptible to motion as coherent processing, frame averaging also produces poor results due to a high rate of tissue motion, which may be acceptable in some embodiments.

In a probe environment, there may be a wired or wireless communication channel between the probe and the main unit. With regard to ultrasound imaging, the communication channel typically should be able to handle high transmission rates and have relatively large data bandwidth. Also, because of the nature of the ultrasound device in medical settings, the communication channel may be sufficiently robust and provide relative immunity from interference of nearby wireless devices, and random electromagnetic noise. In addition, the communication channel may permit the main unit to communicate with and be operable with other wireless and wired probes and systems. For example, the main unit may be able to distinguish certain probes from other probes within proximity.

The communication channels may include more than one channel to increase the data bandwidth available for communication between the probe device and the main unit. Additional channels also may permit interoperability with multiple wireless systems and/or probes, for example, within a certain vicinity of the main unit. It should be appreciated that the communication channels may refer to communication in either direction; namely from the probe to the main unit and from the main unit to the probe.

Robustness and dependability of the communication channel may be facilitated through a variety of methods and techniques. For example, channel redundancy may be used particularly in the presence of interference or noise. In some embodiments, this may be accomplished by switching channels (e.g., automatically) when a channel is occupied by another system, if an excessive or otherwise predetermined amount of data errors are detected, and/or if signal quality is deemed deficient. Another method of improving interoperability may include each transmitter (e.g., either in the probe or main unit) to automatically adjust its signal level depending on signal conditions perceived by the corresponding receiver (e.g., either in the main unit or probe). Robustness also may be implemented in some embodiments by allowing the communication channel to operate in as wide a band as possible to minimize the effects of narrowband interference.

It should be appreciated that such functionality may be a part of the primary communication channel and/or alternate or additional communication channels. As such, the additional channels may be of the same communication type as the primary channel. Alternatively, in some embodiments, the primary and additional channels may have some distinguishing characteristics, like different operating frequencies, orthogonal characteristics (e.g., time, phase, and/or code division multiplexed).

In just one example, in the wireless context, ultra wideband (UWB) techniques may be used for the communication channel to allow the communication channels to allow multiple data streams between transceivers in close proximity. At present, UWB permits data rates of up to 1 Gbits/s for a single link. For example, an interface device that may be employed by some embodiments may include the WiQuest™ chipset, part number WQST110/101. In some embodiments, a probe may have multiple parallel wireless channels running simultaneously using UWB communication methods. Also, it should be appreciated that multiple parallel communication channels may be included in some embodiments to provide a greater data rate. In some embodiments, it may be desirable to use fewer communication channels to reduce physical size and power required of the additional components needed to achieve additional communication channels.

It should also be appreciated that in addition to the primary channel being the same or different than the alternate channel, the alternate channels may be different from one another. For example, in some embodiments, some alternate channels may be based on infrared (IR) technology while the other alternate channels may be based on radio frequency (RF) communication.

In some embodiments, using different or similar main and alternate channels may permit communicating between certain devices, while preventing communication between other devices. Also, it should be appreciated that multiple receive devices on the probe and/or main unit and/or multiple communication channels may be employed. The multiple receive devices may be located in certain locations on the devices to provide a larger area of coverage.

Alternate communication channels may be set up such that one channel is wireless while another channel is wired. Also, some channels may be digital and some channels may be dedicated to data (e.g., the same or different data), while other channels may be dedicated to control data. The various channels may cooperate to increase a transfer rate of the digital ultrasound data and/or minimize a transfer of errors in the digital ultrasound data. Certain channels may provide a greater directional communication path than another communication channel and/or allow the main unit to initiate communication with the remote unit or vice versa. Also, one or more of the channels may communicate a unique identifier with the data, where the unique identifier is used for initiating communication with the remote unit, synchronizing communication with the remote unit, and ensuring communication with a predetermined remote unit. The type of data that is communicated on a particular channel may be varied based upon a capability of the remote unit, power status of the remote unit, capability of the main unit, power status of the main unit, frequency range, array configuration, power warnings, quality of transmission of the data, quantity of errors in transmission of the data, availability of power of the main unit, availability of power of the remote unit, a change in transmission rate, and/or transmission characteristics of the data, etc.

In addition to employing multiple receivers, it should be appreciated that in some embodiments the main unit and/or probe may employ multiple antenna devices in communication with the receivers. For example, in the RF wireless context, the main unit may have more than one receive antennae in order to use antenna diversity to combat multipath effects such as distortion and signal nulls. The multiple antennae and diversity may help improve robustness by providing better signal coverage. Also, in some embodiments, the multiple antennae may be physically separated from each other to reduce multipath propagation effects. In some embodiments, signals may be chosen based on amplitude, phase, SNR, etc.

Using a wireless probe or a wired probe using a relatively smaller cable to communicate, in some embodiments may dictate that additional processing is performed within the probe device and/or outside of the main unit. The disclosed embodiments contemplate several techniques for allowing some processing to occur both within and outside of the probe. For example, in some embodiments, synthetic transmit focus techniques may be used. In some of those embodiments, synthetic transmit focus may allow the received echo waves to be partially beamformed, non-beamformed, and/or some combination thereof.

Some embodiments may include a receive beamformer in the probe that conducts partial or full beamforming. Also, some embodiments may include a transmit beamformer in the probe that conducts partial or full beamforming. These embodiments may be used in lieu of, or in combination with, the synthetic transmit focusing techniques.

Multibeam acquisition methods may be used in some embodiments to acquire data in various scan directions, and/or a relatively large region of the image frame. This may be accomplished in some embodiments substantially simultaneously. By requiring fewer transmit events, multibeam acquisition may provide increased acquisition of image frames. Some embodiments may decrease the rate at which image frames are acquired in order to permit greater signal-to-noise-ratio (SNR) and/or improved resolution, etc. by acquiring greater amounts of data per frame. In other embodiments, an image frame may be acquired using multibeam acquisition using just one transmit event. Some embodiments may employ techniques other than multibeam acquisition, particularly where reduced data bandwidth is desirable, and the embodiments contemplate such alternatives.

In addition to providing techniques for allowing some processing to occur within the probe, some embodiments may require to minimize such processing and or corresponding components. For example, in some embodiments, it may be necessary to reduce the physical size of the probe (e.g., size and/or weight) in order to permit easier use and manipulation by the user. In addition, in those embodiments where the probe includes its own source of power, like a battery, it may be desirable to reduce the required size and weight of the battery for similar user dexterity reasons.

Notwithstanding these techniques, data bandwidth from the probe may be minimized in order to operate within the certain requirements of wireless technology. Techniques that address this need include baseband sampling and matching the sample rate to the final display resolution. Other methods to better manage the data rate from a wireless probe include the use of a frame buffer within the probe and adaptively managing the probe data rate in response to the available wireless bandwidth. A proposed wireless interface is described with particular attention to features novel to the art of wireless ultrasound probes. Actual data rates are provided for a perspective on alternative system designs.

In some embodiments, the nature of the wireless communication may be modified based on various conditions. For example, an available communication capacity of a particular remote, main or other communication unit may be monitored and the communication (wireless or wired) of the ultrasound data may be changed to another transmission rate based on the available communication capacity. The rate may be increased, decreased, and/or changed in some other way (e.g., transmission protocol technique, etc.). Also, a power level of one of the units may be used to adjust the data rate. For example, the rate may be increased, decreased, and/or changed in some other way (e.g., transmission protocol technique, etc.) based on the power level. The power may be provided by a direct current (DC) source like a battery, for example.

Also, other unit performance characteristics may be changed as a function of some operating characteristic of the probe and/or main unit, like the power level or power source and/or the temperature of the probe or main unit. The temperature of the probe may be determined by thermal sensors located proximate to a transducer in the probe and/or proximate a surface of a probe enclosure. These changes may be based upon performance characteristics like an image quality provided by the probe, a drive voltage provided to a transducer in the probe, a voltage waveform provided to the transducer in the probe, a quantity of element used to transmit digital data representative of the ultrasound echo wave, and an acquisition frame rate. The techniques also may provide for giving an indication representative of the changes in the performance characteristics of the probe, main unit, and/or other device. For example, the indication may be a power saving mode light.

The user may change a power state of the probe from a low power state to a relatively more active power state by activating a portion of the user interface, holding the probe, and/or simply moving the probe. These changes in power state may include on to off, off to on, lower power to higher power, and/or higher power to lower power, for example.

Figure 9:
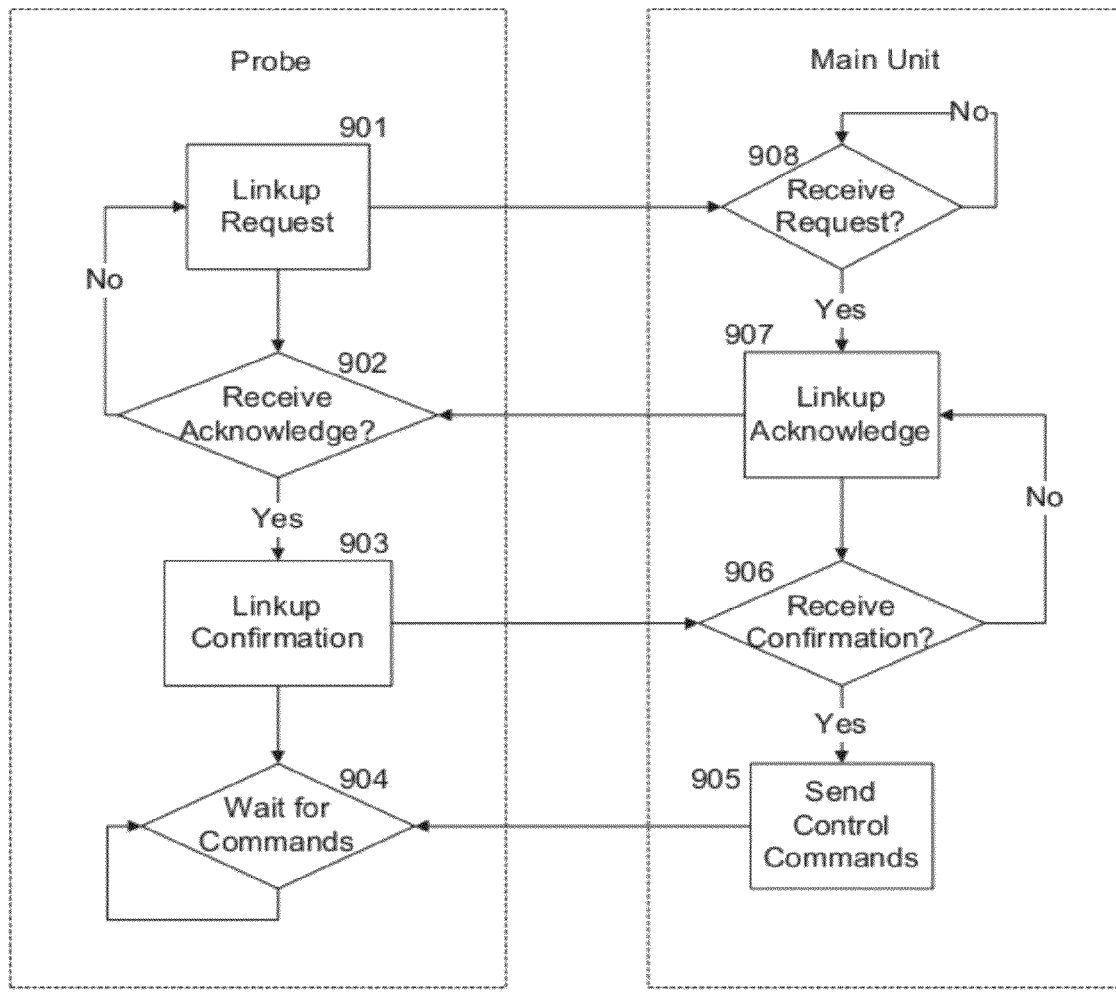
FIG. 9 is a flow diagram of a method for establishing a link between a probe and a main unit.

FIG. 9 is a flow diagram of a method 900 for establishing a link between a probe and a main unit. It should be appreciated that although the method includes just the probe and the main unit, the link may involve other components and processes. Also, the embodiments contemplate other methods for establishing such a link.

The primary and/or alternate channels also may be used to sense a proximity of the main unit from the probe and vice versa. For example, in some embodiments, the primary and/or alternate channels may employ IR, capacitive, inductive, magnetic, and/or any other technique commonly used in sensing a proximity of one device from another.

Proximity sensing may be employed for a variety of purposes, all of which are contemplated by the disclosed embodiments. For example, in some embodiments, it may be desirable to establish an exclusive link between a particular probe and a particular main unit based on a proximity between the two and/or between other devices. Since determining proximity may be difficult using signal properties of a primary RF communication channel, for example, an alternate channel may be utilized in order to facilitate the linkup process. Some alternate communication channels described above (e.g., IR) may be highly directional while others may be specifically designed for proximity sensing. These channels may be used alone and/or in conjunction with another communication channel, for example, during the linkup process.

An exclusive link between probe and main unit may serve a variety of purposes including providing for interoperability of multiple wireless probe-based systems in close proximity to one another, for example. This characteristic of the exclusive link, in some embodiments, may include a temporal limitation. For example, it may be desirable to allow the exclusive link to endure for at least one operating session and/or over some predetermined period of time.

The exclusive link may be initiated by either the probe or the main unit or by some other means. For example, a user may press a button or the like located on the probe, main unit or other device. The exclusive link may be established by communicating a particular data sequence and/or particular data character between the main unit and the probe.

Also, the linkup process may allow the main unit and remote unit (or another unit) to distinguish and/or identify each other. For example, the distinction may be accomplished by determining a proximity of the main unit to the remote units, a relative strength of a signal communicated by the main unit with the remote units, a predetermined identifier, and/or an absence of the another remote unit. The predetermined identifier may include a registered identifier and/or an identifier used in a previous communication between the main unit and the remote units. This also may be accomplished through the use of control data that is unique to the main unit and the remote unit, where the control data initiates, synchronizes and/or ensures communication between the main unit and the remote unit. This communication may be facilitated by the use of one or more antennae located the main unit and the remote unit. The antennae may be arranged to prevent multipath effects including distortion and signal nulls.

In one embodiment, as shown in FIG. 9, for example, the probe may initiate communication with a nearby main unit by transmitting a "linkup request" command at 901 over the wireless communication channel, for example. At 908, it is determined whether the main unit has received the linkup request. If the main unit has not received the linkup request, the main unit continues at 908 to wait for the linkup request. If the main unit has received the linkup request, in some embodiments, the main unit may respond with a "linkup acknowledge" command at 907 sent back to the probe. This "linkup acknowledge" command may provide information relevant to the communication. For example, the "linkup acknowledge" may indicate that the probe is within sufficient range of the main unit to permit wireless communication. Also, the proximity sensing and linkup communication may allow either the probe and/or main unit to automatically wake up from a low-power state, standby mode, and/or otherwise change power status.

At 902, the probe determines whether is has received the linkup acknowledge. If the probe has not received the linkup acknowledge, the method may return to 901 to wait for another linkup request. This return may occur after a predetermined condition, like a timeout or another predetermined period of time.

If the probe has received the linkup acknowledge, in some embodiments, at 903 the probe may communicate back to the main unit with a "linkup confirmation" command to indicate that the communication is established. At 906, the main unit may determine if it has received the linkup confirmation. If the main unit has not received the linkup confirmation the method may return to 907 to wait for another linkup acknowledge. This return may occur after a predetermined condition, like a timeout or another predetermined period of time. If the main unit has received the linkup confirmation, in some embodiments, at 905 the main unit may communicate back to the main unit with a "linkup complete" command to indicate that the linkup is complete. Along with the linkup complete commands the main unit may provide control commands to the probe. At 904, the probe may loop to wait for the commands.

It should be appreciated that the linkup commands may be initiated by either the probe, main unit, and/or some other device, and thus the particular commands may be sent by any of the devices. Also, it should be appreciated that additional communication and corresponding commands relevant to the linkup of the devices are contemplated by the disclosed embodiments. In addition, the linkup may be attempted a certain number of predefined times before it is ceased.

In order to facilitate the linkup process, in some embodiments, both the probe and main unit may be pre-assigned unique identifier codes or identification numbers (e.g., serial numbers), that may be communicated between the main unit and probe (and perhaps other devices) during the linkup process.

The identifier codes may allow, for example, subsequent exclusivity with respect to further communications between the probe and main unit and allow interoperability with multiple wireless probe-based systems in close proximity. It should be appreciated that in some embodiments, interoperability may be a consideration during the linkup process. For example, interoperability and exclusivity may be appropriate where there are multiple main units and/or probes or the like within the wireless communication range that may respond to the probe's and/or main unit's request. In some embodiments, it may be desirable to permit the probe and/or main unit that are in closest proximity to one another to linkup, while in other embodiments it may be appropriate to use other metrics (e.g., signal strength, power status and availability, use selection, most recently linked, etc.).

It should be appreciated that other techniques for accomplishing discrimination between the probe, main unit and/or other devices are contemplated within the disclosed embodiments. For example, non-wireless or wired communication techniques may be used in some embodiments. The techniques may include making electrical and/or magnetic contact between the probe and main unit and/or by allowing a user to press a button on the main unit.

It should be appreciated that the linkup process may be automatic or manual, or a combination of both. For example, some embodiments may permit the entire linkup process to occur without requiring the probe, operator or other device to make contact with the main unit. Other embodiments may require the user to initiate certain portions of the process manually. For example, the user may select a probe type from a displayed list of available probes resulting in the main unit sending a linkup request to probes of the selected type.

In some embodiments, it may be that after the linkup process has been completed, the probe and main unit may include some information (e.g., their identification numbers) in some or all subsequent communication. This may permit the devices to avoid subsequent conflicts or miscommunication with nearby systems. In addition, the probe and main unit may store their own and each other's identification numbers in order to facilitate subsequent linkups after a particular session is terminated or placed in a non-operative mode. For example, the identification numbers may be stored temporarily or permanently in non-volatile memory such as EEPROM, Flash PROM, or battery powered SRAM, well known to those skilled in the art. In this way, if the link between the probe and main unit link is terminated or discontinued for some period, either device (or another device) may attempt to reestablish the link. Such attempted reestablishment of the link may be accomplished automatically (e.g., periodically), upon some operator action, or based on some other input.

Figure 2:
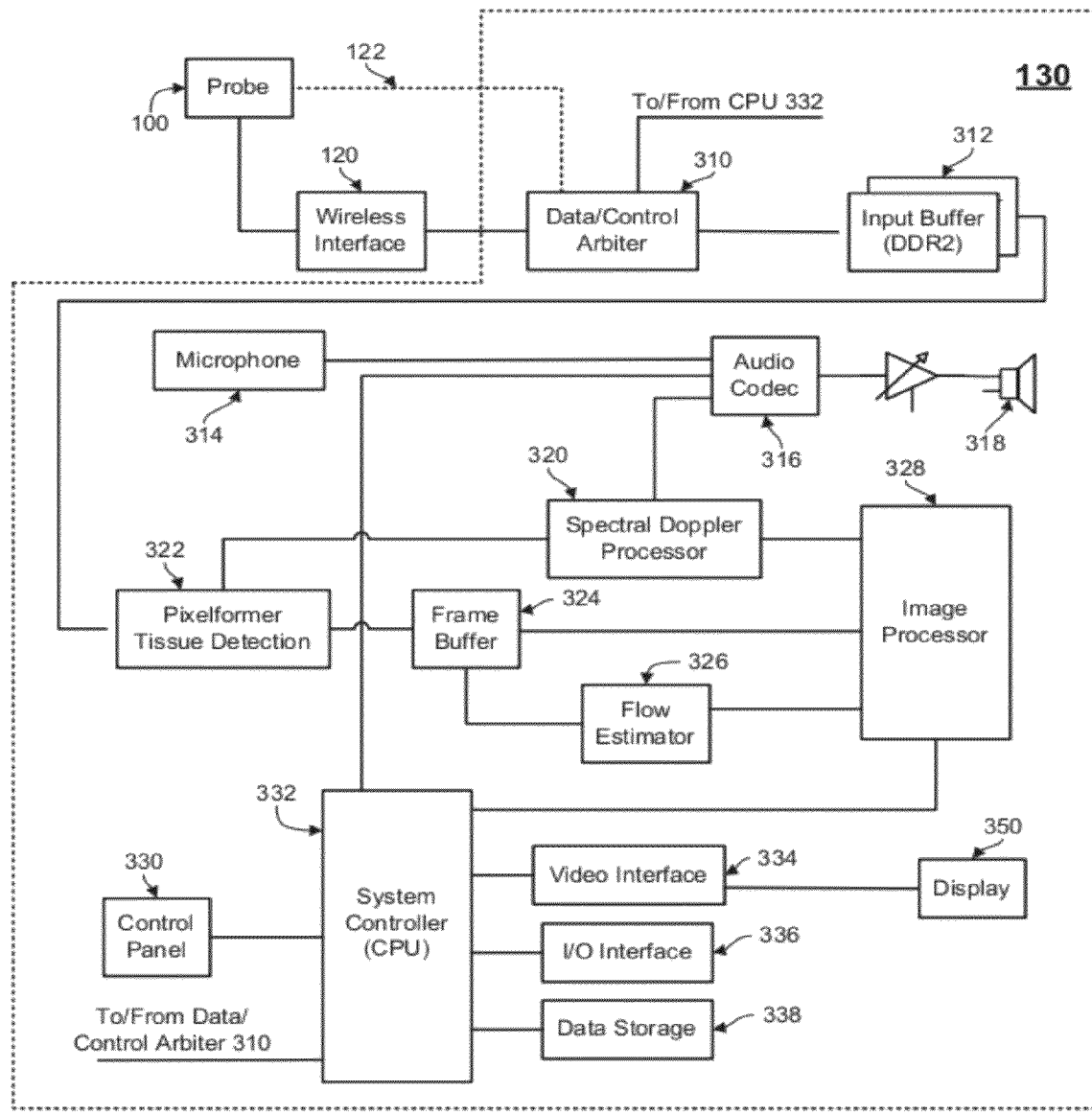
FIG. 2 is a block diagram illustrating various components of a main unit.

As shown in FIG. 2, the main unit may include or be in communication with a display unit. The display unit may display information about the main unit, a linked or other probe, and/or another device. With regard to the probe, the display may provide details regarding the probe type (e.g., frequency range, array configuration, etc.), an identifier code or number, a user pre-assigned name, etc. The name of the probe may be determined by the user and entered at the main unit, communicated to the probe, and written into non-volatile memory within the probe for future reference. Alternatively, it may be entered directed into the probe and communicated back to the main unit. The display also may show information relating to the probe's battery charge status, such as the amount of time the device has left of battery power. Such information may be relevant in some embodiments, for example, where an operator or user may be about to initiate an ultrasound exam and may need to change batteries before beginning the exam. The display also may provide low-battery warnings when the battery reaches a predetermined depleted state, for example. Also, the display may indicate any other operational errors with the system (i.e., main unit, probe, and/or other devices) during a diagnostic or self-test.

Instead of, or in addition to, providing a display indication related to the probe, some embodiments may have indications (e.g., LEDs) on the probe housing, main unit and/or other device. In some embodiments, it may not be desirable to have such indicators on the probe device because of the extra power drain on the battery that may result. In some embodiments, it may be desirable to provide detailed charge state information to the main unit at all levels of charge so the user can monitor and take appropriate action before the battery is depleted or nearly so. In these embodiments, by displaying a charge state on the main unit display instead of the probe device, there may be no additional battery discharge in the probe. Also, the display may permit a user to continuously or nearly so view the charge state during imaging, while still being able to view the remainder of the relevant information without interruption.

Power may be provided to the main unit, probe and other devices using a variety of techniques. For example, the main unit may operate on alternating current (AC) power, battery power or other alternative power sources. Similarly, the probe may operate on alternating current (AC) power, battery power or other alternative power sources. In the embodiments where the probe is wireless or thin-wire, or otherwise incapable of receiving power from an AC source for some period of time, it may be that the probe receives power from a battery, solar power, or other non-AC power source. Although the remainder of the disclosure may refer to battery power generally, it should be appreciated that such references include other power sources including, at least partially, AC power, solar power, and fuel cell sources. Because of the medically sensitive nature of the probe, it may be desirable to ensure that such battery power is available at all times. For example, a backup battery power source may be necessary in some embodiments.

In some embodiments, it may be desirable to conserve available probe power. Such conservation of energy may be limited to a certain period of time, in some embodiments. This may be accomplished using a variety of techniques contemplated by the disclosed embodiments. For example, the probe's circuitry may be turned off or powered down under certain predetermined conditions, like when such circuitry is deemed unnecessary, for example.

In some embodiments, the system may adapt to a change in battery charge by altering acquisition parameters and/or other system operating conditions. Such changing acquisition parameters may trade off image quality or frame rate for power usage, for example. For example, such changing acquisition parameters may include reducing the number of active receiver channels in the probe to reduce receiver power consumption. Reducing acquisition frame rate or transmit voltage may also lower power consumption, and hence, conserve battery power. Some embodiments may alert the user to changes in operating conditions caused by changes in battery charge state. For example, a message appearing on the system display may indicate a power saving mode level.

Similarly, in some embodiments, the system may adapt to the status of an optional thermal sensor located at the probe face by adjusting various system operating conditions to trade off image quality for lower transducer heat generation. Example parameters include the transducer drive voltage level, drive waveform, number of active transmitter elements, acquisition frame rate, etc.

In some embodiments, the main unit may operate on battery power, or perhaps also conserve electrical power usage. Therefore, like the probe, a main unit low-power state, a "standby" or "sleep" mode may be activated after some period of inactivity. The period of inactivity may be terminated automatically, by manual intervention, or some combination thereof. For example, in some embodiments a user may simply change the power status of the probe and/or main unit by pressing a button, or merely handling the probe via motion sensing (e.g., using an accelerometer and/or tilt switch, etc.). Also, the power status of the probe and/or main unit may be changed by the probe sensing a grip of the user's hand (e.g., by detecting heat, capacitance change, pressure, etc.). In some embodiments, it may be desirable to use a combination of sensing methods and/or to allow activation by deliberate operator action so it may not be triggered accidentally.

Other methods for conserving and controlling power status of the components in the system may include manual and/or automatic changing of power conditions (e.g., power off) to the components once a procedure is completed. The termination and/or changing of power conditions may be based on some predetermined period of time accrued by a timer in the system. For example, if a component like the probe is not operated for some period of time, the component may change its power state (e.g., turn itself off and/or place itself into a different power state). A different power state may include a relatively lower or higher power state. In some embodiments, this may be accomplished by changing the power state of a certain number of the portions of the probe or other device. For example, when imaging is in a "frozen" state (i.e., no live imaging) the probe's data acquisition and/or wireless interface transmitter circuitry may be turned off.

Initiating the change in power state may be accomplished in a number of ways all of which are contemplated by the disclosed embodiments. For example, some embodiments may contemplate various techniques for detecting a lack of activity, including the probe using motion, acceleration, heat and/or capacitance, or the like. Also, some embodiments may measure inactivity dictated by a period of time where controls on the probe, main unit, and/or other device are not operated. Also, following such inactivity, the component could power down either immediately and/or after some delay. The time period could be specified by the user and/or by some component in the system, including the probe, main unit or other device. Because in some embodiments, the main unit may communicate control information (e.g., periodically) to the probe, it may be desirable to allow the probe to detect a lack of control commands (e.g., over an extended period of time) from the main unit. For example, the probe may power itself down for a variety of reasons including because the main unit is either no longer turned on, is inoperable, and/or has been moved to a location out of wireless communication range, etc.

Figure 10:
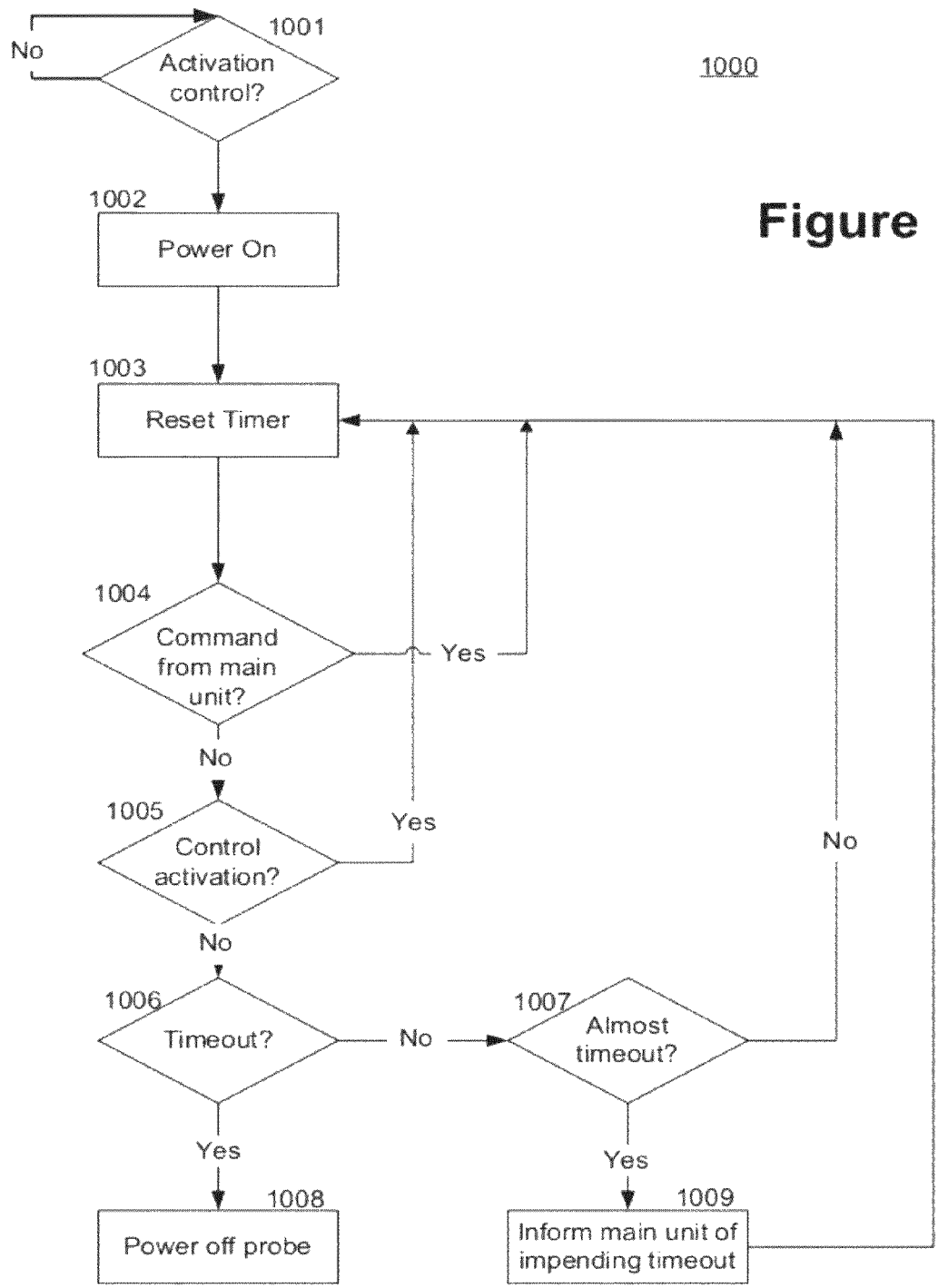
FIG. 10 is a flow diagram of an inactivity timeout.

FIG. 10 provides just one example of a flow diagram 1000 for a probe inactivity timeout. As shown in FIG. 10, it is determined at 1001 whether an activation control has been activated. If, at 1001, it is determined that an activation control has not been activated, a loop will continue to check to see if an activation control has been activated. If, on the other hand, at 1001 an activation control has been activated, power is provided to the probe at 1002. At 1003, a timer is reset. The timer may be used to count to a predetermined time to determine if the probe has been inactive long enough to turn off the probe.

At 1004, it is determined whether a command is received by the probe, for example, from a main unit and/or another device. If, at 1004, a command is received by the probe, the timer is reset at 1003. If, on the other hand, at 1004, it is determined that a command is not received by the probe, it is determined at 1005 whether activation control is received by the probe. If, at 1005, it is determined that activation control is not received by the probe, the timer is reset at 1003. If, on the other hand, at 1005, it is determined that activation control is received by the probe, it is determined at 1005 whether a timeout has occurred. If, at 1005, it is determined at 1005 that a timeout 1006 has occurred, the probe is powered off at 1008. If, on the other hand, at 1005, it is determined at 1005 that a timeout has not occurred, at 1007, it is determined whether the timeout almost has occurred. If, at 1007, the timeout almost has occurred, the main unit may be informed of the impending timeout at 1009. If, on the other hand, at 1007, it is determined that the timeout almost has not occurred, the timer is reset at 1003.

In some embodiments, it may be desirable to permit the probe to remain active for some predefined time period after initial linkup, for example. It may be such that when the predefined period of time is about to run out, some indicator may be displayed for the user either on the probe (e.g., via a LED), the main unit (e.g., via a display), and/or both.

In addition, it should be appreciated that in some embodiments, the main unit and other devices may include similar non-AC power concerns and capabilities described above with regard to the probe.

In addition to providing and controlling power, some embodiments may include monitoring a charge or other status of the battery while in use and/or dormant. For example, in some embodiments, a controller may monitor the battery. The controller may be a separate part of the system and/or built into the battery pack. In some embodiments, the controller may track the characteristics of the battery and its use. For example, the controller may keep track of the amount of time the battery has been used, as well as the charge and discharge cycles. Also, the controller may provide feedback to the system and display such information to the user regarding the battery's current charge state. This may be accomplished, for example, by monitoring such parameters as the battery's open-circuit voltage, integrated current in and out since last full charge, etc. In some embodiments, such information may be transferred between the battery and probe or other devices using communication channels. Also, in some embodiments, estimating battery charge state may be accomplished using battery open-circuit voltage, load current integration over time (e.g., coulomb counting), and/or battery source resistance, for example.

In this way, the controller may facilitate real-time understanding of the battery's capability as well as predict future performance of the battery.

It also should be appreciated that the battery interface may include some physical characteristics specific to medical environments. For example, the battery interface may need to be tolerant and/or resistive of gel and/or other conductive liquids.

Figure 11:
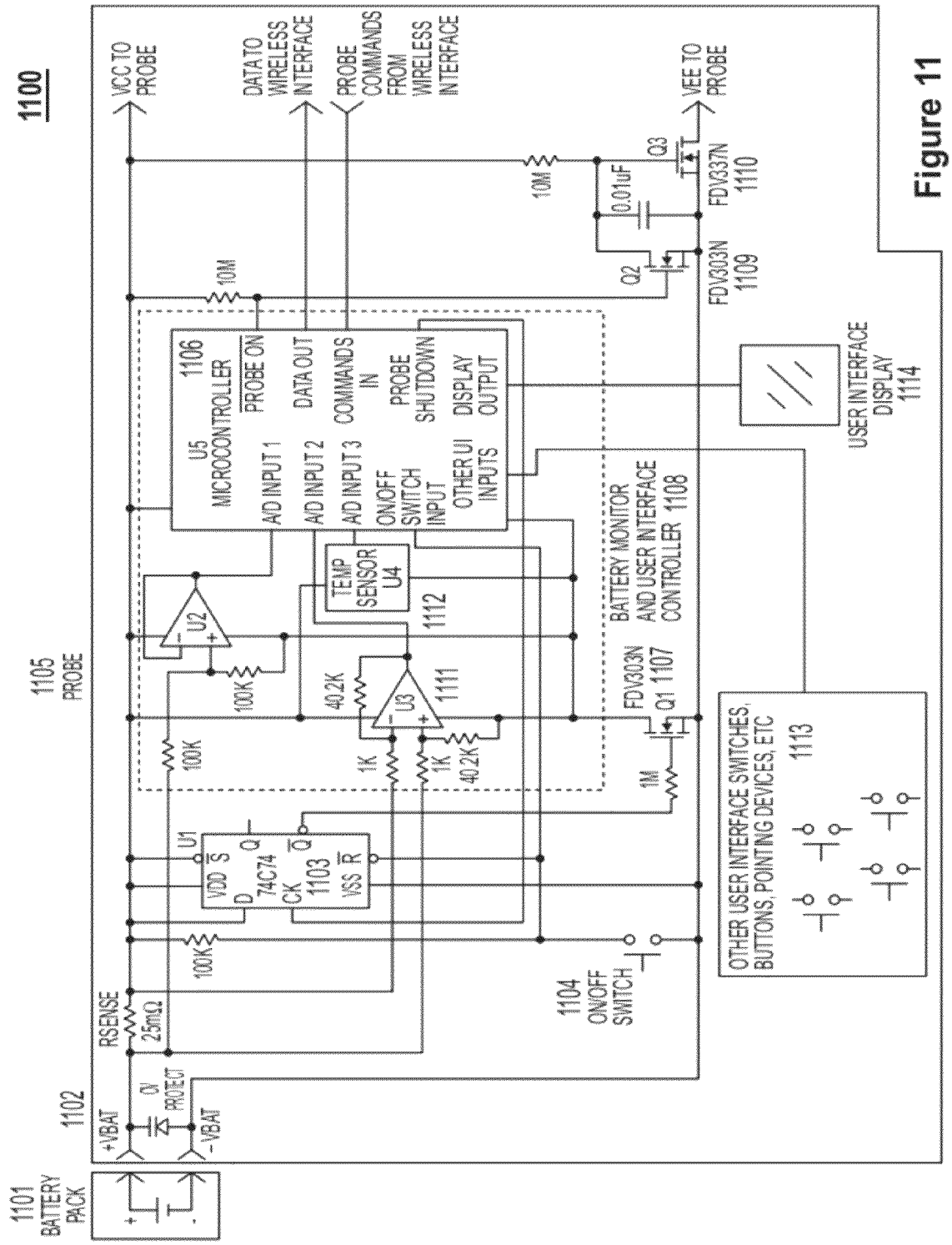
FIG. 11 is a block diagram of an example battery monitoring and control circuit.

FIG. 11 is a diagram of an example battery monitoring and control circuit 1100 that may be used to monitor and/or control a battery for use with a probe 1105. In some embodiments, the battery may be a rechargeable type of battery for example, a Lithium ion battery. An over-voltage (OV) diode 1102 may be used to protect internal circuitry from electrostatic discharge (ESD) events. Also, a flip-flop device 1103 may be used to store a current on-off state, and may be connected to an ON/OFF switch 1104. Switch 1104 also may have other additional functionality, for example, after probe 1105 is operating.

To activate probe 1105, a user may press switch 1104, for example, by depressing it for a certain period of time (e.g., 100 mS or more). To turn probe 1105 off, a microcontroller 1106 may monitor switch 1104 to determine whether it has been depressed for a certain period of time, for example, 3 seconds or more. In some embodiments, after switch 1104 is released after being depressed for a predetermined period of time, microcontroller 1106 may send a battery monitor shutdown command. The command may provide a rising edge on a clock input of flip-flop device 1103, and operate to turn off probe 1105.

When flip-flop device 1103 is in a reset state, transistor 1107 is turned on, and power is connected to battery monitor and user interface controller (BMUIC) 1108. In some embodiments, BMUIC 1108 may be a microcontroller with analog/digital inputs, two op-amps and a temperature sensor. Once power is provided to BMUIC 1108, it may begin gathering data about battery 1101. For example, if battery 1101 has sufficient capacity, BMUIC 1108 may provide power to the remainder of probe 1105. BMUIC 1108 may have control of power provided to the remainder of probe 1105 by driving transistors 1109 and 1110. BMUIC 1108 also may power itself down in some embodiments, for example, if battery 1101 has a reduced charge to some degree, and/or if probe 1105 is turned off by the user and/or by command from the main unit or some other device.

Output of op-amp 1111, available at A/D input 2 of microcontroller 1106 may measure current drawn by probe 1105. Full scale range of the current load sensor may be approximately 2 amps. Average current load of probe 1105 in operation may be 0.5-1.0 amps. Once probe 1105 is running, source resistance of battery 1101 may be monitored continuously by microcontroller 1106. The load current of probe 1105 may vary, for example, depending on the operating mode, and by monitoring load current and terminal voltage of battery 1101. Source resistance of battery 1101 may be calculated as a change in the battery terminal voltage divided by a change in load current. Knowing resistance, current load and terminal voltage of battery 1101, for example, it may be possible to calculate a virtual open-circuit voltage of battery 1101.

Also, available to microcontroller 1106 may be the temperature of probe 1105 housing. A temperature sensor 1112 may be located near battery 1101, and may be used to sense ambient temperature. As is well known to those skilled in the art, battery temperature may have a relatively significant effect on its capacity. In some embodiments, for example, in hospital and clinical environments, normal conditions will have ambient temperatures of approximately 20-30° C. In some embodiments, battery 1101 may have a charge reserve of about 1 ampere-hour, so that a fully charged battery may supply approximately an hour of operational time. Typically, within a relatively short period of time after being attached to probe 1105, battery 1101 may be fairly close to the ambient temperature, even if it started out at a significantly different temperature. Therefore, in some embodiments, sensing of the temperature of battery 1101 may not have a relatively large effect on the overall circuit accuracy.

Measurements of current consumption, battery terminal voltage and ambient temperature, for example, may be communicated through a wired and/or wireless interface back to the main unit and/or some other device. Estimate of the remaining battery capacity may be made at the main unit, probe 1105, and/or some other device. In some embodiments where determination is made at a place other than probe 1105, the complexity of the algorithm used to estimate the remaining capacity in battery 1101 may not be constrained by the likely reduced processing capacity of microcontroller 1106.

The main unit may display on the main imaging display screen an estimate of the remaining battery capacity based on current and expected probe usage patterns. In some embodiments, such usage data may not be available to microcontroller 1106, and so it may be desirable to implement a battery capacity estimation algorithm in the main unit.

BMUIC 1108 also may implement numerous safety features. For example, BMUIC 1108 may allow probe 1105 to discharge the battery only to a certain predetermined level, after which it may terminate operation. Also, in some embodiments, BMUIC 1108 may provide over-current protection for probe 1105, and perhaps terminate probe operation to protect the probe and battery pack. In some embodiments, thresholds for these values may have default values and/or also may be modifiable by the main unit, for example, as probe commands.

It should be appreciated that in some embodiments, measurements of battery terminal voltage, current consumption, temperature and estimated battery source resistance and open-circuit voltage may be sent back to the main unit through a wired and/or wireless link. These values may be communicated at various intervals, for example, every 10-30 seconds.

BMUIC 1108 also may act as a user interface controller for probe 1105. It may receive switch inputs, potentiometer settings, pointing device inputs, etc. from user interface input devices 1113, and supply these controls to the main unit through a wired and/or wireless interface. The user interface may include a number of features that allow a user to interact with probe 1105. For example, the user interface may include a depressable button, a motion detector, an acceleration detector, a heat detector, and a microphone. Also, the user interface may provide an indication to the user of a number of things. For example, although not exclusive, the user interface may provide power status, designation of remote unit, type of remote unit, frequency range, array configuration, power warnings, capability of the remote unit, quality of transmission of digital data, quantity of errors in transmission of digital data, availability of power required for transmission of digital data, change in transmission rate, completion of transmission, quality of data transmission, transmission characteristics of the non-beamformed ultrasound wave, processing characteristics of the echoed ultrasound wave, processing characteristics of the digital data, and transmission characteristics of the digital data, etc.

BMUIC 1108 also may receive display data from the main unit and/or other device and present it on user interface display 1114. It should be appreciated that microcontroller 1106 may provide additional operational functions for other subsystems within probe 1105.

Figure 12:
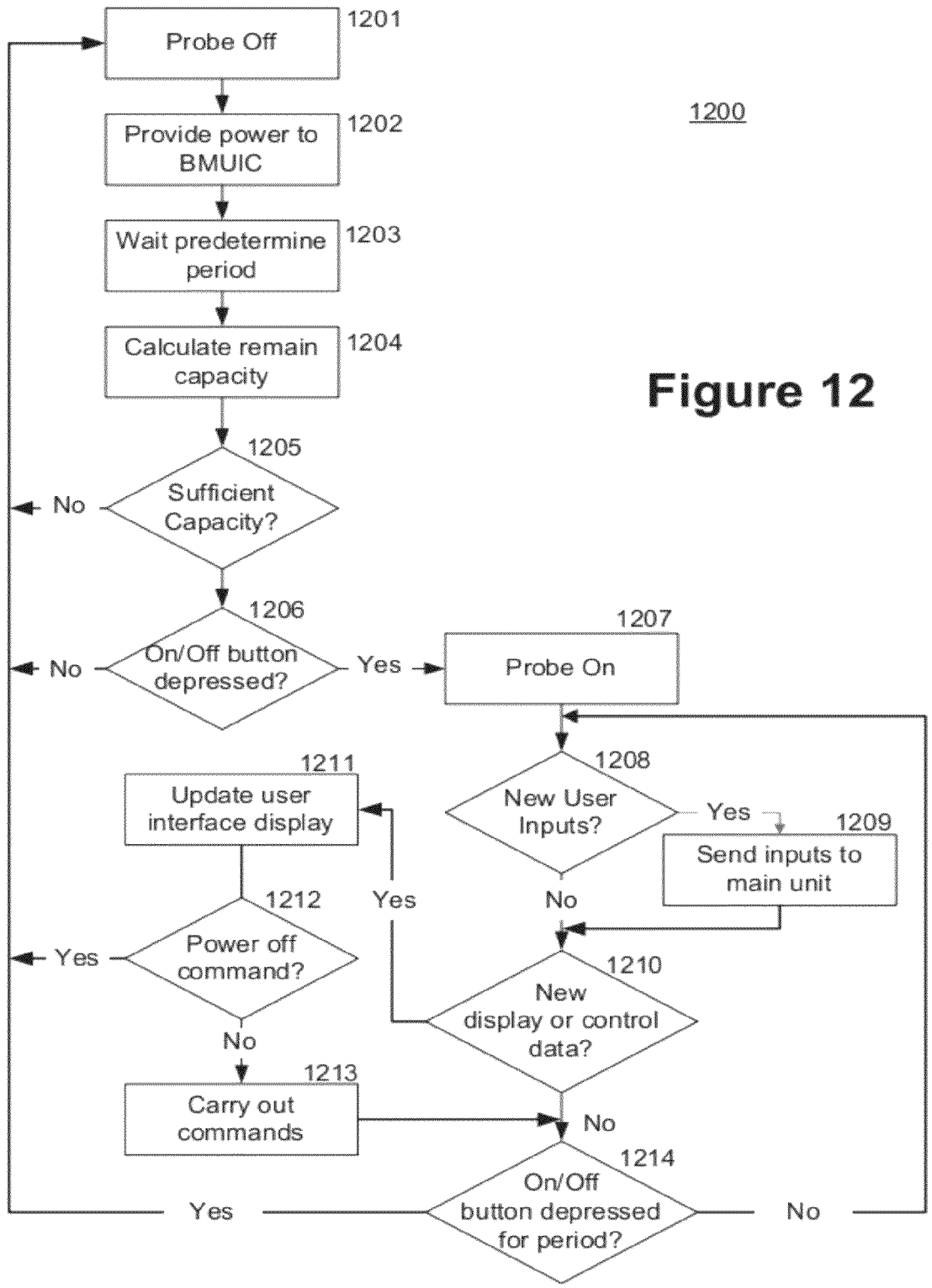
FIG. 12 is a flow diagram of a power control technique.

FIG. 12 is a flow diagram 1200 of a power control technique that may be implemented by BMUIC 1108. It should be appreciated that the disclosed embodiments contemplate a number of power control techniques. For example, the disclosed embodiments may include a power controller that controls the power the power source and adjusts the electrical energy from the power source. Such control may be accomplished by changing a load, like the transducer and the transceiver, for example. Also, the power controller may adjust the electrical energy from the power source based an amount of the ultrasound data communicated by the transceiver. Similarly, the transceiver may adjust communication of the ultrasound data based on a characteristic of the power source, like capacity, type, charge state, power state, and age of power source. The power source may be a direct current source, like a battery. The power control techniques may also increase, interrupt, and/or reduce power from the power source depending upon time immediate or after a certain amount of time, like a duration from an initial application of the electrical energy, a predetermined threshold of available electrical energy, a predetermined amount of time, and a predetermined amount of inactivity. The inactivity may include a user pressing a button, a motion detector located somewhere within the system, an acceleration detector, a heat detector, and a microphone (e.g., for voice-activated commands).

It should be appreciated that the power controller may adjust the electrical energy provided any of the components of the system including the transducer, analog-to-digital converter and transceiver, etc. A command to power down any of these components may be received from a probe, a remote unit, the main unit, or another unit.

As shown in FIG. 12, when the ON/OFF button is pushed in 1201, flip-flop 1103 will reset, turning on transistor 1107 and supplying power to BMUIC 1108 in 1202. BMUIC 1108 powers up and waits at 1203, for example for 100 mS. The waiting period may allow the power supply to settle and stabilize, and/or provide a "debouncing" delay for the ON/OFF switch. In 1204, BMUIC 1108 measures battery terminal voltage and ambient temperature and makes an estimate of the remaining capacity. If the capacity is not above the minimum capacity threshold, probe 1105 may be turned off at 1201. If, on the other hand, it is determined at 1205 that the capacity of the battery is above the minimum capacity threshold, at 1206, it is determined whether the on/off button is still depressed. If it determined at 1206 that the button is not depressed, probe 1105 may be turned off at 1201. If, on the other hand, at 1206, it is determined that the on/off button is still depressed, BMUIC 1108 may issue a "probe on" command that drives transistors 1109 and 1110 and supplies power to the remainder of probe 1105 to run the probe at 1207.

While probe 1105 is running, BMUIC 1108 monitors user interface inputs 1113 to determine whether new inputs are being provided, at 1208. If, at 1208, it is determined that new user inputs are being received, the new user inputs may be sent to the main unit and/or another device at 1209. The data may be communicated via a wired and/or wireless interface. If, on the other hand, at 1208 it is determined that no new user inputs are being received, it may be determined at 1210 whether any additional data and/or information from the probe or another device needs to be displayed by BMUIC 1108 on the user interface display. If, at 1210, it is determined that such new data and/or information should be displayed, the user interface display may be updated at 1211. For example, in some embodiments, user interface inputs may be "soft keys" whose function depends on the current operational state of probe 1105. Such soft key labels may be displayed on the user interface display to convey their function. In some embodiments, this labeling information may be maintained locally in BMUIC 1108 and provided to the display. Also, there may be special diagnostic modes of operation wherein internal data and measurements within probe 1105 may be displayed on the user interface display. It should be appreciated that other types of data and/or information may be updated.

If, at 1212, it is determined that a power off command has not been received from the main unit and/or another device, the control data commands may be executed at 1213. If, at 1212, it is determined that the power off command has been received from the main unit and/or another device, probe 1105 may be turned off at 1201. After the commands have been executed at 1213, it may be determined whether the on/off button has been depressed for a predetermined period of time. If, at 1214, it is determined that the on/off button has not been depressed for a predetermined period of time, process 1200 will return to 1208. If, on the other hand, at 1214, it is determined that the on/off button has been depressed for a predetermined period of time, probe 1105 may be turned off at 1201.

In some embodiments, particularly those perhaps involving a wireless probe for example, it may be that certain interfaces may be created to maintain a sterile environment. For example, some embodiments may create a user interface that permits operation of the system with little or no need to access portions of the system beyond the sterile boundary. In the context of a user interface to the probe, some embodiments may keep an operator from having to manually reach out beyond the sterile field to change system settings or make adjustments. Instead, such embodiments may permit the user to make such adjustments and control the system from the probe housing that may be located within the sterile field. In those embodiments where the probe is located within a sterile sheath, the interface may remain operable. In order to facilitate such sterility, some embodiments may provide a control interface on the probe. The control interface may include a touch pad, an LCD touch screen with soft-keys, another pointing device, etc.

Also, "hands-free" operation of the system may be facilitated by allowing voice-based commands to be processed by the system via a microphone. The microphone may, for example, be built into the probe, the main unit, and/or any other parts of the system to allow a user to control the system with voice commands. In some embodiments, particularly where the microphone is installed on the wireless probe, the voice-based command may be converted and communicated over a wired or wireless link with the main unit and/or other system component.

In some embodiments, the wired or wireless link may be the same as, or distinct from, the link over which the ultrasound data is communicated in the system. For example, image acquisition data, control data and microphone data may be packetized and sent to the main unit over the wired or wireless interface. In some embodiments, where more than one data stream is sent across the same communication channel, the data streams may be multiplexed. It should also be appreciated that if the wired or wireless channel cannot handle the amount of data, one or more of the data sources may be adaptively altered to accommodate the available bandwidth. For example, the microphone signal sampling rate and/or dynamic range may be scaled down if the wireless communication link is not large enough.

Figure 13:
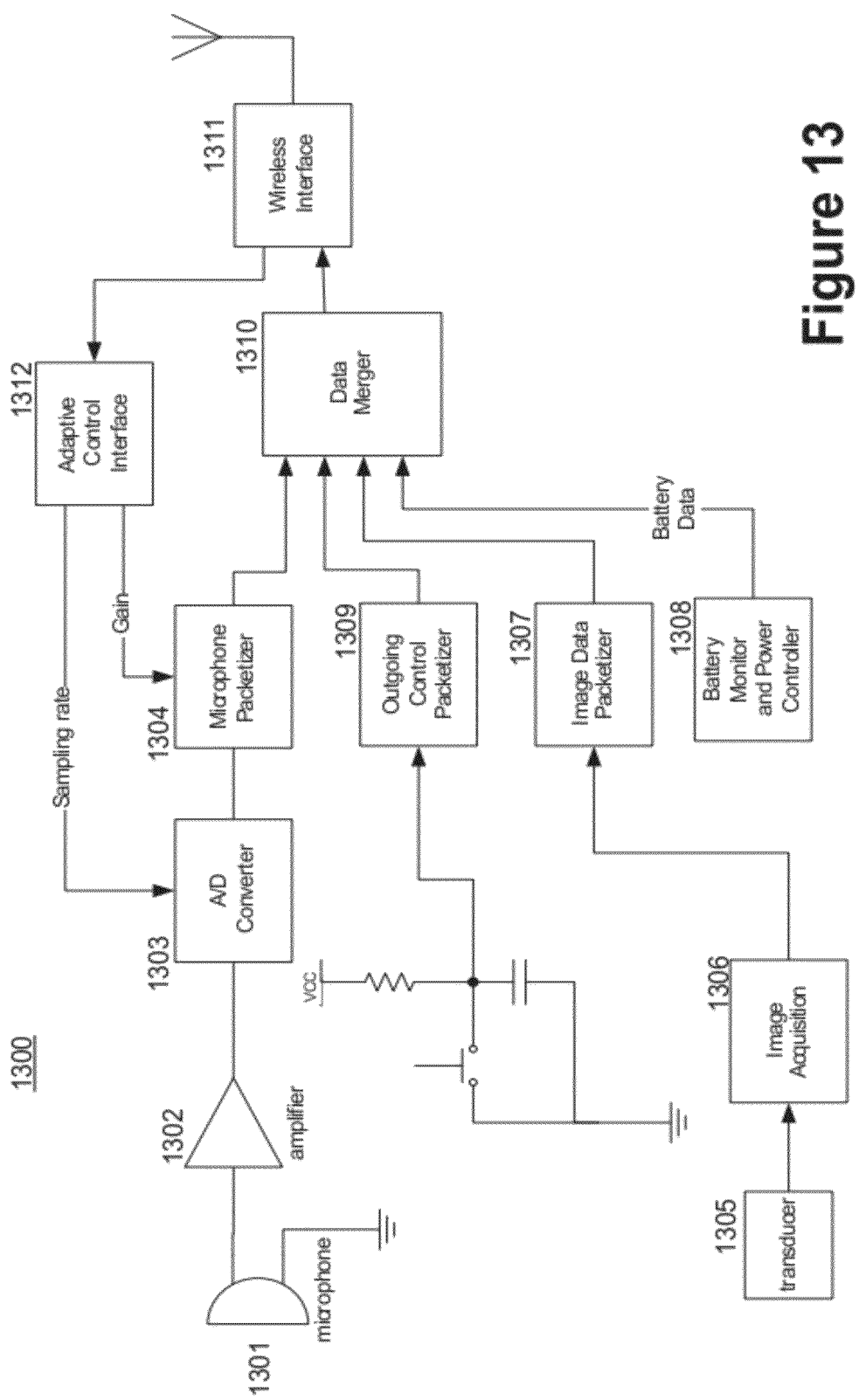
FIG. 13 is a block diagram illustrating data merger and adaptive control.

FIG. 13 is a block diagram illustrating data merger and adaptive control system 1300. As shown in FIG. 13, a microphone 1301 is in communication with an amplifier 1302. Amplifier 1302 is in communication with an analog-to-digital (A/D) converter 1303. A/D converter 1303 may operate to sample and digitize a signal from microphone 1301. A/D converter 1303 may have a sampling rate that may be adjusted by an adaptive control interface 1312 that may be responsive to a controller within the probe, the main unit, and/or another device. A microphone packetizer 1304 in communication with A/D converter 1303 may provide an adjustable number of bits per sample and/or dynamic range of the microphone signal data. Microphone packetizer 1304 also may encode the data in a compressed format using any number of standard and/or proprietary audio compression techniques (e.g., MP3) for further data reduction and possibly with variable compression parameters responsive to the adaptive control interface 1312. Microphone packetizer 1304 also may arrange the microphone audio data into discrete packets before merging with other data sources via a data merger 1310.

Also, as shown in FIG. 13, an outgoing control packetizer 1309 may receive control inputs from pushbuttons, knobs, trackballs, etc. and may arrange the associated control data into discrete packets before merging with other data sources via data merger 1310. Image data also may be packetized via an image data packetizer 1307 before data merger 1310. Image data packetizer may receive an image via transducer 1305 and image acquisition 1306. Battery status information may be generated by battery monitor and power controller 1308 function and passed to data merger 1310 to merge with other data sources. A thermal sensor (e.g., a thermistor) may be located where the probe makes contact with the body in order to sense probe temperature at the patient interface. The thermal sensing functionality may translate a signal from the thermal sensor into thermal status information to be sent to the main unit, for example, via data merger 1310. Both the battery and thermal status information may be made available in discrete data packets. Data merger 1310 may prioritize multiple data sources according to a predetermined and/or adaptively adjusted priority level. Data merger 1310 also may merge the data packets into one or more data streams leading to the wired and/or wireless interface 1311.

It should be appreciated that this description encompasses many types of probe designs including non-invasive, external probes as well as semi-invasive and/or invasive probes such as percutaneous, catheter-based, endo-cavitary, transesophageal, and/or laparoscopic probes in wired and/or wireless embodiments. For example, certain catheter-based, endocavitary, transesophageal, and/or laparoscopic probes are contemplated as wired and/or wireless probes.

Catheter-based ultrasound transducer probes may be used for intra-luminal and intra-cardiac ultrasonic imaging. There are various types contemplated by the disclosed embodiments including rotating single element, radial array and linear phased array. Rotating single element probes may be simpler to manufacture but may provide relatively poorer images due to their fixed focal depth. Also, in some embodiments, the scan plane rotating single element probes may be diametral to the catheter shaft. Linear arrays may be oriented along an axis of the shaft of the catheter, and therefore provide an image in a plane that is longitudinal to the catheter shaft. Linear arrays are typically more useful on larger vessels because they generally require a larger catheter shaft. Matrix and/or two-dimensional catheter-based transducers are also contemplated. In addition to side-fire methods, these may employ end-fire array geometries as is the case with other types of probes, in some embodiments, sterility may be desirable for catheter probes. As a result, embodiments that include a wireless catheter probe facilitate greater sterility by reducing and/or eliminating a need for a wired connection to the main unit.

In some embodiments, the probe or other components may be able to be configured, programmed and/or calibrated over the wired and/or wireless link from the main unit or other component. For example, in some embodiments, when the probe powers up for the first time, it may be that the wireless link and its support circuitry are fully functioning. The probe may include support circuitry that may be a field-programmable gate array (FPGA) with a boot EEPROM. The FPGA may be an Altera Cyclone™ FPGA or the like, that are provided with configuration data or calibration data. In some embodiments, the FPGA may be programmed from the wired or wireless interface without the need for a boot EEPROM. Alternatively, the boot EEPROM may be reprogrammable via the wireless interface to facilitate firmware updates. In this case, the FPGA may be initially programmed with the current EEPROM contents upon power up, after which time new programming code is loaded into the EEPROM from the wireless interface. The next time the probe is powered up, the FPGA may be loaded with the new EEPROM contents.

In some embodiments, other components like an acquisition controller, signal processing blocks and probe identification circuitry may be programmed after power up. After establishing the wireless link between the probe, main unit, and/or other components, an FPGA programming command may be communicated over the link to program the acquisition controller and the signal processing blocks. These blocks may also be reprogrammed to support different user input controls modes (i.e., color vs. b-mode, etc.) and/or reprogrammed to optimize for different tissue types and/or various other operating conditions. Reprogramming may occur while the image is frozen, on a frame-by-frame basis, and/or before each transmit event if necessary.

In some embodiments, a control interface for an FPGA may include control lines along with one or more data lines. Alternatively, if any of the hardware in the probe is a microcontroller, software could be downloaded in a manner similar to that described for the FPGA. Configuration tables for acquisition timing and coefficients for filtering and other signal processing functions may be loaded over the link. These configurations may be different for various user-controlled settings such as depth changes and/or mode changes, for example.

Configuration data or information may be provided from any of the components in the system Such configuration data, may include without limitation, power status, designation of device, type of device, frequency range, array configuration, power warnings, capability of a remote unit, quality of transmission of digital data, quantity of errors in transmission of digital data, availability of power required for transmission of digital data, change in transmission rate, completion of transmission, quality of data transmission, look-up tables, programming code for field programmable gate arrays and microcontrollers, transmission characteristics of the non-beamformed ultrasound wave, processing characteristics of the echoed ultrasound wave, processing characteristics of the digital data, and transmission characteristics of the digital data, etc.

Probe identification like serial number, probe type, bandwidth, revision number, and calibration data, for example, may be programmed into non-volatile memory either over the wireless link or a wired programming port. With respect to calibration, a calibration feedback loop may be initiated where acquired data is transmitted to the main unit to perform calculations. The main unit may then communicate such information as offset and gain data back to the probe where the data may be stored in a memory. In some embodiments, calibration may occur periodically and/or only once during probe production. In the latter case, the storage memory device may be non-volatile such as flash memory or EEPROM.

In some embodiments, it may be desirable to allow the user to locate a probe. For example, it may be that the probe is misplaced or the user needs to select one of many available probes and needs the proper probe to be distinguished for the operator. The system may include locator functionality that operates in a variety of ways contemplated by the disclosed embodiments. For example, some embodiments may include locator functionality with limited detection or geographic range, such that probes within the predetermined range (e.g., 10 meters) may be detected, while probes outside the range may be ignored in some embodiments. Also, the locators may have different characteristics, which may include active, passive or hybrid locator functionality, and the like.

Active locator functionality, for example, may include a receiver that may be of low power. The receiver would monitor (e.g., constantly, intermittently, etc.) for a particular electronic signature of the probe. For example, the electronic signatures may include RF emission characteristics, identification number, magnetic field signatures (e.g., magnetic field of circuitry, magnetic fields modulated with a particular signature, etc.).

In some embodiments, the probe may be identified to the user by a number of audible or visible techniques. For example, the system may emit an identifiable audible response, such as a beep for example, when it detects the proper probe (e.g., receives a particular RF signature). In some embodiments, the system may provide a visual indication, like the flashing of an indicator light when it detects the proper probe. Alternatively or in addition, it should be appreciated that these indicators may work by indicating an improper probe to prevent the user from selecting and using the wrong probe. It should also be appreciated that other techniques for providing indication of and locating for probes are contemplated by the disclosed embodiments. Also, in some embodiments, the indicators may be able to indicate a direction and/or distance that the user may travel to find the probe. For example, the indicator and locator functionality may use global positioning techniques, well known to those skilled in the art.

The communication between the locator components (e.g., receiver) may be the same wireless and/or wired channel used to communicate the image and/or control information between the probe, main system and other devices. Also, in some embodiments the locator functionality may have the option to use alternate communication channels.

Some embodiments may allow the locator communication channel to operate using techniques that allow reduced power consumption. For example, the locator's receiver may be powered for relatively shorter periods of time as needed, and then powered off when not needed (e.g., when waiting or after probe has been located).

Passive locator functionality also is contemplated by the disclosed embodiments. These passive techniques may not require active or powered circuitry in the probe, or other devices. This embodiment may be desirable where conservation of power in the system is a consideration. In this embodiment, for example, the locator functionality and components may produce an identifiable signature when placed into electrical and/or magnetic presence of an external source (e.g., an RF field).

In some embodiments, the external source may be attached to or housed in the main unit of the system and/or other systems or non-system devices. Also, the external source may be removable from being anchored to the system so as to facilitate searching for a lost probe. The external source may be AC powered or battery operated for greater portability. In some embodiments, the external source may emit a signal (e.g., a RF beacon signal). Some embodiments may use a signal having a particular frequency that is responsive with the passive receiver. As with the active locator functionality, upon detecting and/or locating the probe, an indication may be made to the user. Some embodiments may include the locator functionality within the probes such that one probe could be used to find another probe and/or to locate or distinguish itself, for example. For example, it may be able to ignore itself and find another probe by disabling the locator functionality while the probe is helping to find another probe.

It should also be appreciated that a combination of the passive and active techniques may be used in a hybrid system. For example, some embodiments may include a passive circuit sensitive to a particular RF signature that generates a trigger signal to activate a remainder of the locator components so that the probe can identify itself as described.

In some embodiments, the locator functionality may use relatively low-frequency RF, and magnetic coupling to communicate. In this way, the locator functionality may be able to operate over greater environmental circumstances and conditions. For example, using the low frequency, allows the generated magnetic fields to travel through more materials like conductive enclosures. In this way, the probe may be located even if it is placed in a metal cabinet, trash can and/or patient. Also, some embodiments may eliminate conditions like multi-path nulling by allowing the coupling between the antennae and devices to create a near-field phenomenon. In this way, the signal strength may be more accurately calculated as a function of distance and allow the locator functionality to be set to a power level that reliably covers a desired finding distance, yet not so far as to stimulate probes at a greater distance.

In some embodiments, because of the relatively lower frequency, the required power of the locator circuit may be reduced. For example, the power level may be nominal as compared to battery capacity. In this way, in some embodiments, the locator functionality may be run continuously (or nearly so) as may be necessary to find a lost probe, yet use relatively little battery power.

Figure 14:
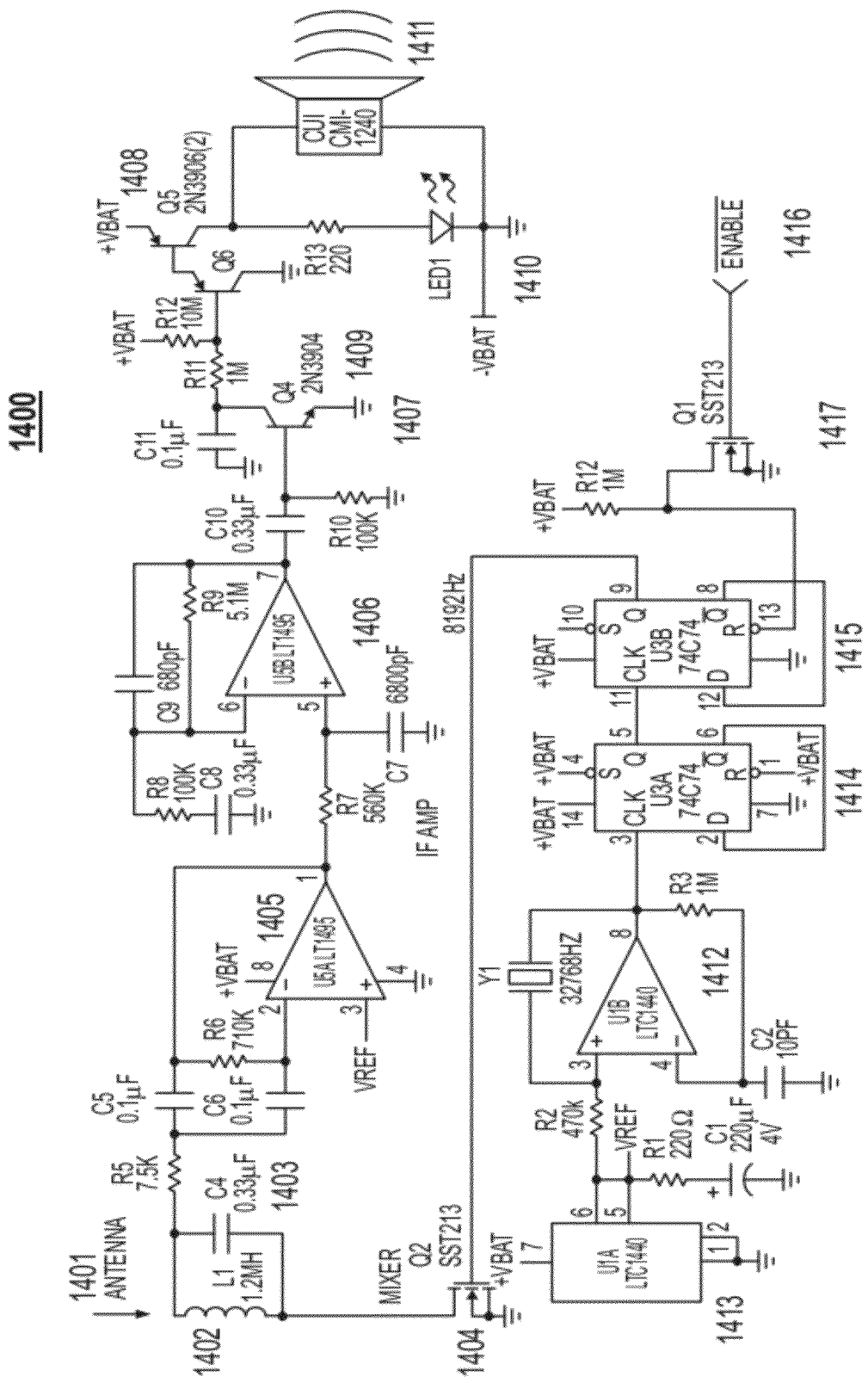
FIG. 14 is a block diagram of a circuit that provides locator functionality.

FIG. 14 is a block diagram of a circuit 1400 that provides locator functionality. Although FIG. 14 is an example of a specific circuit, it should be appreciated that this is just one example of such a circuit and does not preclude the use of other components in the circuit or even other circuits. The components shown and discussed may not represent all of the components that may be used, but are limited for the purposes of clarity and brevity.

The probe locator circuitry may allow a probe to find a main unit, a main unit to find a probe, and/or a main unit and probe to find another unit, or vice versa. The locator functionality may be a part of a module that is located within the main unit, the probe, and/or another unit. The module may use global positioning, triangulation, radio frequency identification, and/or ultrawideband communication, for example. Communication for the locator functionality may be accomplished wirelessly and/or over a wire. The locator may work independently of and/or in conjunction with a proximity sensor using optical, infrared, capacitive, inductive, electrically conductive, and/or radio frequency techniques. The locator functionality may be initiated by a user that interacts with the user interface, such as a momentary switch that the user depresses continuously (or nearly so) to activate the locator functionality.

The locator functionality may operate by providing an audible and/or visible signal module that emits a sound or shows when the locator module identifies the remote unit, the main unit, and/or another unit. Of course, the indications also may be used to identify an improper remote unit, main unit, and/or other unit, and to prevents a user from selecting the improper unit. The locator module may be designed, in some embodiments, to identify a location of the unit when the unit is within 10 meters. Also, in some embodiments, perhaps to conserve resources like power, the locator functionality may attempt to identify the location of the remote unit intermittently. Also, the locator functionality may provide an indication of a direction and distance that a user should travel to precisely locate the unit and/or units. Also, the locator functionality may passively produce a locator signal such that when placed into an electrical field and/or magnetic field, a signal is generated. The magnetic field may operate with a relatively low frequency to permit the magnetic field to travel through obstructions (e.g., trash can, file cabinet, etc.) to the locator module.

As shown in FIG. 14, an antenna 1401 may be constructed with an open magnetic path. For example, the magnetic path may be an air coil with a large radius and/or a solenoid having a high permeability ferrite rod. In some embodiments, the open magnetic path may permit magnetic fields to couple through the windings of antenna 1401. The magnetic field may be created with a particular frequency, for example, centered at 8192 Hz. Also, the magnetic field may have a certain spatial orientation, for example, such that the magnetic flux path is substantially parallel to the central axis of antenna 1401. In some embodiments, a tuned circuit with inductor 1402 and capacitor 1403 may resonate with the impinging magnetic field.

In some embodiments, a mixer transistor 1404 may be used and may be switched on and off at a magnetic field frequency (e.g., 8192 Hz) that may include some mixing functionality to demodulate 8192 Hz to a DC level of 0 Hz. For some embodiments, any modulation on the magnetic field may be translated in frequency by 8192 Hz. Amplifiers 1405 and 1406, and their associated components, may comprise an intermediate frequency (IF) amplifier and bandpass filter with a predetermined center frequency (e.g., 20 Hz). In this way, the IF amplifier output may respond to any double-sideband or single-sideband modulation that is approximately at the center frequency from the carrier (e.g., 8212 Hz or 8172 Hz). Also, the output of the IF amplifier may be AC coupled to transistor 1407 to operate as a simple voltage threshold comparator and rectifier. In some embodiments, for example when there is 20 Hz modulation on the 8192 Hz carrier, and the received signal is of sufficient amplitude, transistor 1407 may pull its collector low and hold it there while the signal is present. This may be buffered by transistor 1408 to drive transistor 1409. Transistor 1409 may pull its collector node high, turning on the indicator LED 1410 and sounding beeper 1411.

Clock 1413 and amplifier 1412 may generate a clock signal (e.g., 32768 Hz) that may be divided down by a certain factor (e.g., four) in clocks 1414 and 1415 to generate a clock value (e.g., 8192 Hz) that may be required to run the gate of mixer transistor 1404. In some embodiments, for example when operation of circuit 1400 is not needed, a high voltage level (e.g., greater than 3V) on ENABLE input 1416 may disable operation of circuit 1400 by holding clock 1415 in reset, such that mixer transistor 1404 does not run. It may be that no input can be detected because the antenna input is floating, and thus the enable input may be used to terminate operation of locator circuit 1400 or portions thereof. This termination may occur in many instances, including for example, when the probe is imaging in association with a main unit, and when it is being used as a finder for another probe. In either instance, ENABLE 1416 may be taken to a positive supply (e.g., greater than 3V) in order to disable operation of circuit 1400. For example, ENABLE 1416 may be driven from transistor 1417.

In the example circuit shown in FIG. 14, operational power supply current of the above circuit may be about 7 µA, which in some embodiments may be low enough that the circuit can be connected to the battery continuously without harm (e.g., battery capacity may be approximately 1 amp-hour). In this example, even if the battery has been depleted to 10% of its total capacity, enough energy would exist to power the circuit for more than 1.5 years. As a result, in some embodiments, the locator may be connected directly or indirectly to the battery pack leads. Also, in some embodiments it may be that the locator does or does not have separate battery management control.

Figure 15:
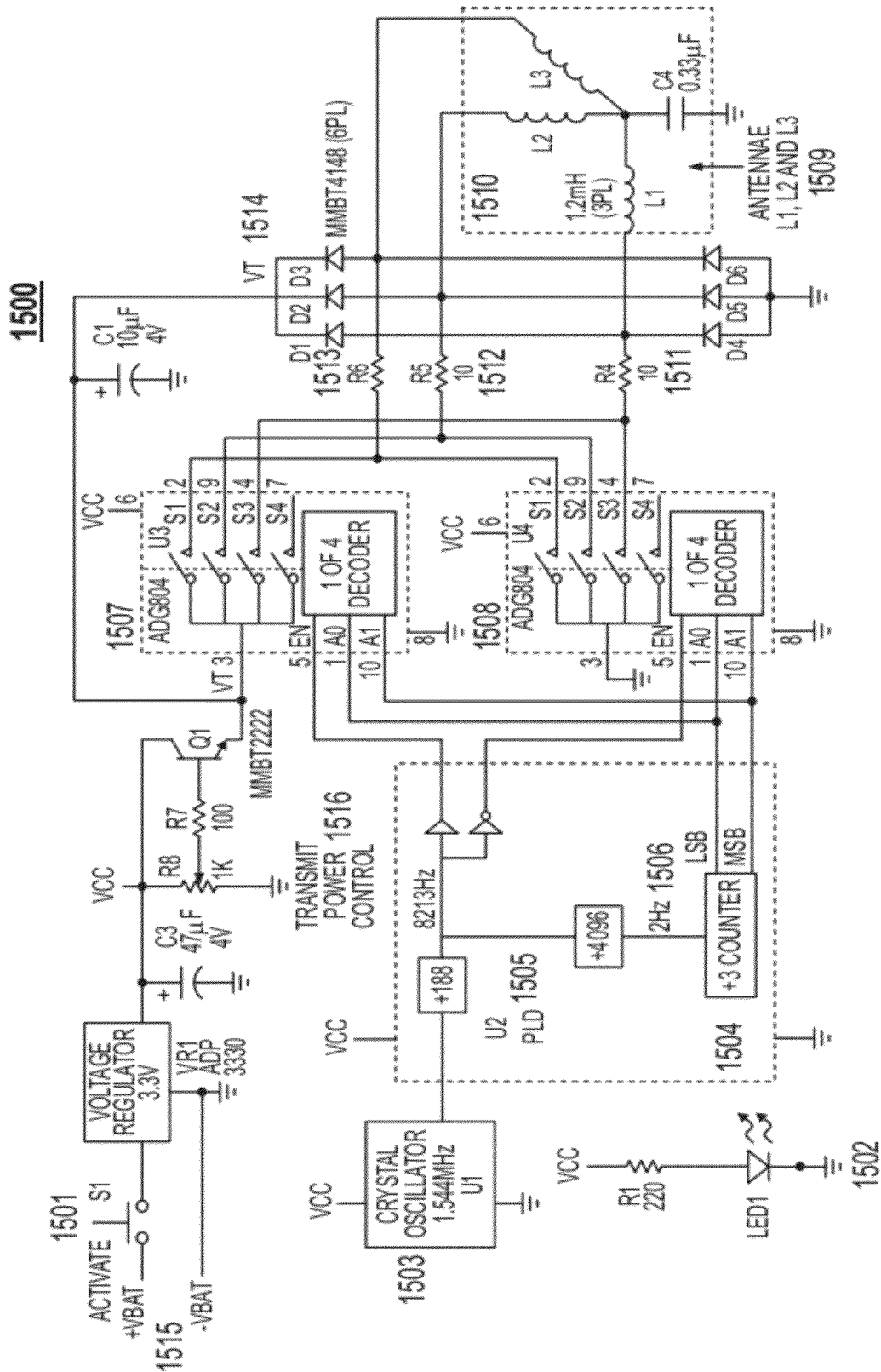
FIG. 15 is a block diagram of a circuit that provides external source functionality, for example in a passive locator environment.

FIG. 15 is a block diagram of a circuit 1500 that provides external source functionality, for example in a passive locator environment. Circuit 1500 may be designed to emit a field to which locator circuit 1500 may respond. Although FIG. 15 is an example of a specific circuit, it should be appreciated that this is just one example of such a circuit and does not preclude the use of other components in the circuit or even other circuits. The components shown and discussed may not represent all of the components that may be used, but are limited for the purposes of clarity and brevity.

As shown in FIG. 15, the external source used in the passive locator, for example, may begin operation when a user presses switch 1501 and provides power (e.g., via battery 1515) to the remainder of circuit 1500. In some embodiments, switch 1501 may be a momentary switch, such that the user may have to hold down switch 1501 for the circuit to interrogate its surroundings. Having a momentary switch instead of another type of switch may facilitate circuit 1500 not using additional power accidentally, when not in use. Indicator 1502 may indicate to the user that circuit 1500 is operating. Circuit 1500 may take on various forms. For example, circuit 1500 may be built into the main unit, it may be a hand-held module that docks in the main unit, but is removable to search for probes. Also, circuit 1500 may be integrated into a probe, such that one probe may be used to find another, etc.

In operation, the crystal oscillator 1503 output may be fed to a simple programmable logic device (PLD) 1504 that may include clock dividers 1505 and a counter 1506. In this example, a first clock divider may generate an 8213 Hz signal, that may be some frequency (e.g., 21 Hz) above a center frequency (e.g., 8192 Hz). This may create a simple single sideband (SSB) modulation at 21 Hz. The clock may be fed to components 1507 and 1508, and cause them to alternately pull their outputs to some voltage (Vt) or ground. This may drive the series-tuned output circuit and stimulate the output antennae to emit a magnetic field at a frequency of 8213 Hz, for example.

Output antennae 1509 may have an open magnetic path, such that their magnetic flux couples through free space. The open magnetic path may be necessary to couple to the antenna of locator circuit 1500. Output antennae 1509 may be of the same design as the receiving antenna inductor of locator circuit 1500. Some embodiments may include three output antennae because the coupling from transmitter to receiver may be dependent on the relative orientation of the two, in some embodiments. Therefore output antennae 1509 may be mounted in such a way that their magnetic axes may be mutually perpendicular.

The field generated by circuit 1500 may couple the transmitter and receiver in proportion to the cosine of the angle between their central magnetic axes. For example, if the antenna is a solenoid, it is the central axis of the solenoid. As a result, in some embodiments, it may be necessary to emit fields in a number of different orientations to ensure that the transmitter magnetic axis is not substantially perpendicular to the receiver magnetic axis. In those embodiments that employ three mutually perpendicular axes of orientation in the transmitter, the receiver axis may not be more than 54.7° from one of the axes of the three transmitter antennae. Therefore, PLD 1504 may use a divide-by-3 counter that sequences through three states on a 2 Hz time base to sequentially stimulate the three antenna axes for 0.5 s each.

Some embodiments may use a transmitter power control 1516 to possibly allow setting of an output drive level to the antennae. The output drive level may be set to a stimulus level that may be sufficient to be detected by the locator circuit at about five meters, for example. Five meters may be of sufficient distance to allow finding probes within the immediate vicinity of the user without extending the reach of the finder too far. For example, it may not be of much use to extend the reach too far because the probe needs to be within view or hearing of a user in order to be found anyway. Of course, some embodiments may include tracking at a distance greater than five meters for other purposes.

Output antennae 1509 may be driven based on the state of counter 1505 used in PLD 1504. Because in some embodiments output antennae 1509 may be inductive, when the transmit drive to one of them becomes disconnected, it will generate an inductive voltage spike as it dissipates any energy stored in its magnetic field. As a result, resistors 1511-1513 and diodes 1514 may be used to shunt this voltage spike to the power supplies and protect components 1507 and 1508. Resistors 1511-1513a or other resistors also may be used to set the Q of the series tuned output circuits. In particular, the impedance of the output circuit 1510 at resonance may have a minimum of 10 ohms to allow the drive current (and the proportional magnetic field) to be sufficiently controlled.

Although circuit 1500 is shown connected to battery 1515, it should be appreciated that circuit 1500 may receive power from an AC power source. In some embodiments, circuit 1500 may use as much as 130 mA. In these embodiments, it may be necessary for the battery must have substantial drive capability. Also, because in some embodiments the circuit may not be used for extended periods (e.g., more than a few minutes at a time) the total energy capacity of the battery may not need to be very high. For example, in some embodiments, a battery capacity of 100 mA-hours may suffice. Also, it should be appreciated that these values are just estimates that may be changed, for example, if there is the possibility of recharging, for example, while circuit 1500 is docked in the main unit. For example, an even lower capacity battery may be sufficient.

In some embodiments, the data transmission rate may be based upon the product of a minimum acceptable frame rate and an amount of data per frame. Some embodiments may be required to deliver a minimum acceptable frame rate, for example, because of some external clinical requirements. In these embodiments, it may be that for a given data transmission rate, an amount of data per frame may be less than some maximum amount. In some embodiments, if the amount of data per frame is assumed fixed, the data transmission rate may be above some minimum value. Typically, the minimum frame rate may be set by the clinical requirements, and a number of embodiments are contemplated to vary the amount of data per frame. Also, in these embodiments, various possible approaches are available to gain different data transmission rates. In some embodiments, it may be desirable to reduce frame rate in order to reduce the required data transmission rate from the probe, for example.

In some embodiments, several hundred million bits of data may be generated per frame. For example, a probe with center frequency Fc=6 MHz and 20 bits of baseband data spanning 4 cm (i.e., approximately 350 samples), may produce 350×20 bits of data per transmit/receive element combination. Sparse array techniques may be used to limit the number of transmit/receive element combinations per frame to approximately 2048. For a 480 Mbps data rate, the resulting frame rate for these example operating parameters may be $480 \times 10^6/(350 \times 20 \times 2048)=33$ fps.

It should be appreciated that some embodiments may be influenced by reduction of system power requirements. Also, some embodiments may make it desirable to move functions between the probe, main unit and other components, and vice versa, for example to perhaps reduce the size of the required circuitry in those devices. In those embodiments where functionality is moved out of the probe, relatively higher bandwidth requirements may be found. This reduction of bandwidth requirements may be accomplished using a number of techniques contemplated by the disclosed embodiments.

In certain contexts, these embodiments may be impacted by the fact that the communication link may be relatively shorter (e.g., 3 meters from an ultrasound wireless probe to the main unit). Generally, some embodiments may make it desirable to reduce an amount of data communicated between the probe (i.e., either wired or wireless), the main unit, and/or other devices. Such techniques may be desirable whether the system uses synthetic transmit focus techniques, acoustic transmit focus techniques, and/or some combination thereof.

Although certain methods are disclosed, it should be appreciated that the embodiments are not limited to such methods. Instead, the disclosed embodiments include numerous techniques to reduce data between the probe, the main unit, and other devices. For example, certain of the contemplated methods may manipulate system processes related to resolution, field of view, dynamic range, and/or any other parameters associated with the image display and any other points throughout the processing chain. Such methods also may be, for example, based on various system components such as the transducer, signal processor, display, and the like. In some embodiments, the methods may involve dependency on certain user settings, including depth range, displayed dynamic range, and the like. Also, these data reduction techniques may be dependent or independent on the type of ultrasound techniques employed, like acoustic transmit focusing, synthetic transmit focusing, beamforming and/or non-beamforming, etc.

The methods include, but are not limited to, tissue dynamic range, lateral resolution, region of interest, axial resolution, and color flow clutter to signal ratio (CSR). Although some of the methods may be discussed in the context of synthetic transmit focus and/or acoustic transmit focus, it should be appreciated that the methods are not so limited, but may be applied to other techniques including a combination of approaches. Also, the methods may include various imaging techniques, including color flow mode, B-mode imaging, spectral Doppler mode, etc.

With respect to tissue dynamic range, a displayed dynamic range, for example, of a B-mode tissue image typically is selected by the user. The particular range is predetermined to be within some range made available by the system. The dynamic range may refer to a ratio of the largest displayed signal level to the smallest visible level. In some embodiments, the system may provide a default dynamic range, depending upon the particular application. In some embodiments, excess signal dynamic range may be carried through the signal processing path to accommodate a maximum allowable setting (e.g., greater than 60 dB).

Because in some embodiments the displayed dynamic range may be limited at some point in the image processing prior to display, it may be possible to reduce the dynamic range earlier in the processing path. Reducing the dynamic range may allow for reduction of the required data bandwidth. For example, dynamic range may be set to support just what is required to display the image at the selected setting, for example. In some embodiments, this reduction may be accomplished without sacrificing any image quality, or with sacrificing a level of image quality that is acceptable to the user.

In some embodiments, dynamic range may be varied by mapping the digital data a different number or values. This, for example, may accomplish data compression of the digital data. For example, the data compression may be lossless compression of the digital data. The mapping may be accomplished by mapping one digital data value to a number and/or mapping more than one digital data value to a number. Also, the mapping may be accomplished based on certain predetermined ranges, such that a digital data value within a first range may be mapped a certain way, while a digital data value within a second range may be mapped another way.

In some embodiments, the mapping techniques may include selecting a portion of the digital data and/or varying the selected portion over a time. The time over which the portion is varied may include a distance traveled by the ultrasound echo wave, a displayed image, and a depth of penetration of the ultrasound interrogation wave. Also, the particular selection may be based on characteristics of ultrasound echo wave and/or characteristics of the digital data. The values may be represented by a number of data bits, such that the selected portion of the digital data represents a number of bits at least equal to a number of bits of the digital data. The technique may also include comparing a characteristic of the digital data to a predetermined threshold, and determining a portion of the digital data as a function of the predetermined threshold. The portion of the digital data may include a number of bits of data, and a number of transmitted bits may be less than a number of available bits.

In some embodiments, the dynamic range may vary throughout the image processing. Just one example of such variation occurs with integration or antenna gain, where the dynamic range of a beamformed signal may be greater than individual channel signals. The increase in dynamic range may be caused by an integration gain (IG) that is approximately equal to $10 \log_{10}(N)$ dB, where N is the number of combined channels. In those embodiments that include typical phased array systems, N may represent the receive channels combined in the receive beamformer, for example. In embodiments that include synthetic transmit focus techniques, N may include the element combinations used for both transmit and receive focusing, for example. In some embodiments, N typically will be approximately an order of magnitude greater than a phased array system, or have a greater dynamic range of at least 10 dB.

It should also be appreciated that dynamic range may vary with depth of penetration of the interrogating wave. For example, as the required depth increases for the interrogating wave to hit a target, the strength of the echoed wave may be reduced, for example, because of signal attenuation and transmit beam characteristics. As a result, in some embodiments, it may be that lower intensity echo signals require relatively less dynamic range than larger signals. As a result, it may be desirable in some embodiments to adjust dynamic range to the varying signal requirements to reduce the required amount of data. For example, reducing the number of data bits for signal data in the far-field where echo signals are the most attenuated, may permit greater data reduction.

In those embodiments that include phased array techniques, it may be that beam intensity is a maximum at some focal point, yet decreases farther from the focal point. In those embodiments that include a synthetic transmit focus system, because unfocused or defocused transmit beams may be used, the beam may be divergent with some near field effects due to the fixed elevation focus and the element factor of the transducer. Typically, with synthetic transmit focus, the echoed wave may attenuate relatively more quickly and have relatively lower intensity echoes compared to systems using focused transmit beams, for example. There may be, however, an increase of dynamic range on the receive side as a result of the dynamic transmit focusing used in synthetic transmit focus systems, for example.

Calculating required signal dynamic range depends on a channel signal level, integration gain, and the displayed dynamic range, for example. Available signal dynamic range may be determined by subtracting noise floor from peak signal level. In some embodiments, available signal dynamic range may be increased by the integration gain, for example, to levels that may exceed the displayed dynamic range. Integration gain and available signal dynamic range may vary with depth, so a resulting combined signal dynamic range also may be a function of depth. While the available signal dynamic range typically decreases with depth, the integration gain may cause the dynamic range to increase with depth due to an f-number and/or acceptance angle criterion, which is well known in the art as referring to the ratio of the focal length of a lens (or lens system) to the effective diameter of its aperture. With respect to ultrasound arrays, for example, the f-number may refer to the ratio of the focal distance to the width of the array aperture (typically controlled by the number of active array elements or some weighting function applied across the aperture). Therefore, the aperture grows larger proportional to the distance from the transducer. For example, for an f-number of 2, the aperture width is set to half the focal distance, so at a point 2 cm deep, a 1 cm aperture will be used. For an element pitch of 1 mm, this corresponds to 10 active array elements.

In some embodiments, before displaying the image, the integrated and detected image data may be compressed to a set dynamic range, such that any excess dynamic range may be clipped to some maximum level. In those embodiments that use such clipping, it may be desirable to conserve data and optimize the dynamic range and required signal bandwidth earlier in the image processing. For example, dynamic range in excess of the clipping may be limited by appropriate gain adjustments and/or data bit allocation.

Other techniques may contemplate varying the dynamic range with depth, so as to accommodate just what is required. This may be accomplished using a number of techniques contemplated by the disclosed embodiments. Just two of such techniques may include applying gain adjustment based on measured peak signal levels, and adjusting a data quantization (e.g., number of bits) throughout the depth range. In some embodiments these functions may be either fixed by being based on typical signal levels and known display dynamic range, and/or dynamic so as to provide for widely varying signal levels.

For some embodiments, the gain adjustment technique may include both an analog time-gain control function, a digital gain control, and/or a combination thereof. In those embodiments where the analog-to-digital converters provide adequate dynamic range by themselves, it may be desirable to set the analog time-gain control to a default setting with gains set as high as possible to prevent loss of smaller than expected signals. In these embodiments, any dynamic control may be provided digitally prior to transmitting data from the probe to the main unit. Also, in some embodiments, digital signal levels may be monitored either on the probe, the main unit, and/or some other device. In some embodiments, because the main unit may allow for greater data processing capabilities, it may be desirable to perform such processing at the main unit. In these embodiments, the associated data may be passed, for example via a resultant control table, from the main unit to the probe to establish the gain control function.

The gain control function may be specified as a fairly simple set of transition points. For example, at more shallow penetration depths, signals may be set to a maximum dynamic range of approximately 10 bits and shifted to some amplitude level based on peak signal levels. Some embodiments may permit, at a given range sample, the bit width to be decreased and/or the range shifted down to accommodate the requirements of the value of the range. In some embodiments, it may be that the process is continued throughout a part of or the entire depth range of interest. At greater depths, the signal may drop below some noise floor or minimum, such that a minimum number of bits may be required to represent the data. Also, in some embodiments, it may be that when the signal amplitude is either above or below some predetermined level of the gain control function, it is clipped.

Figure 16:
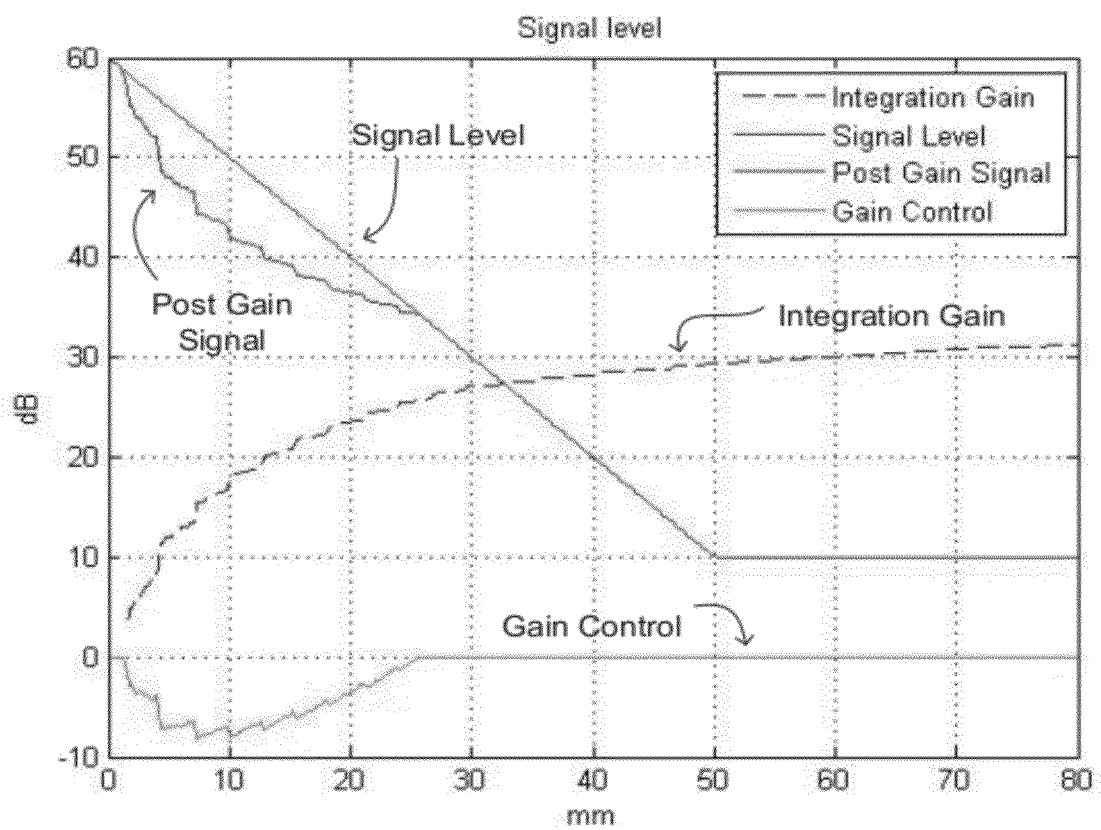
FIG. 16 is a graphical depiction of the signal levels, integration gain, gain control factor, and attenuated signal levels.

FIG. 16 is a graphical depiction of the signal levels, integration gain, gain control factor, and attenuated signal levels over an 80 mm range. The example illustrated in FIG. 16 provides an illustration of tissue dynamic range based on synthetic transmit focus techniques having a divergent or defocused transmit beam. Although the example is provided in this context, the disclosed embodiments are not so limited, but may be applied to other contexts including acoustic transmit focus techniques. Also, while the example provides values for the purposes of clarity and brevity, it should be appreciated that any such values are contemplated by the disclosed embodiments.

A maximum analog front-end gain is set such that the noise following the analog-to-digital converter is approximately 7.5 dB above the analog-to-digital converter noise floor. Also, the total front-end in addition to analog-to-digital converter noise is 10 dB RMS. On average, the received echo signal plus noise in the near field occupies 60 dB and is attenuated at a constant rate of 1 dB/mm. It should be appreciated that these values may be fixed in the system and/or may be dynamically computed by the system based on acquired signals. The displayed dynamic range is set to 50 dB. There are 96 transducer elements and may be decimated by a factor of 3, and there may be a maximum receive aperture of 48 elements. The transmit f-number is 1.5 and receive f-number is 1.0. A maximum 10-bit limit is assigned to the channel data prior to transmission.

As shown in FIG. 16, because the noise floor is 10 dB at a gain of 0 dB, the skin-line dynamic range is 60−10=50 dB. Also, because 50 dB equals the display dynamic range, in some embodiments no gain adjustment is required. As shown in FIG. 16, at 10 mm, even though the signal level has dropped 10 dB, the integration gain has increased by 18 dB making the total dynamic range 50−10+18=58 dB. Because 8 dB may be above the display range, some embodiments may be reduced by 8 dB. At 26 mm the integration gain is almost 26 dB but the signal level has decreased to only 34 dB so the effective dynamic range again equals 50 dB and, in some embodiments, no gain adjustment may be needed. Beyond 26 mm, the effective dynamic range is less than 50 dB so the gain remains at the maximum of 0 dB.

In some embodiments, the signal level post-gain adjustment may determine the required data. Typically, near the skin-line or surface of the medium, little dynamic range comes from the integration gain. As a result, in some embodiments, most of the dynamic range may be carried in the main channel data, and perhaps require more data. As the signal levels decrease, in some embodiments less data is required. As shown in FIG. 16, eventually at 48 mm, the signal drops below the noise floor and only the minimum number of bits may be required, in this case 3 bits.

Figure 17:
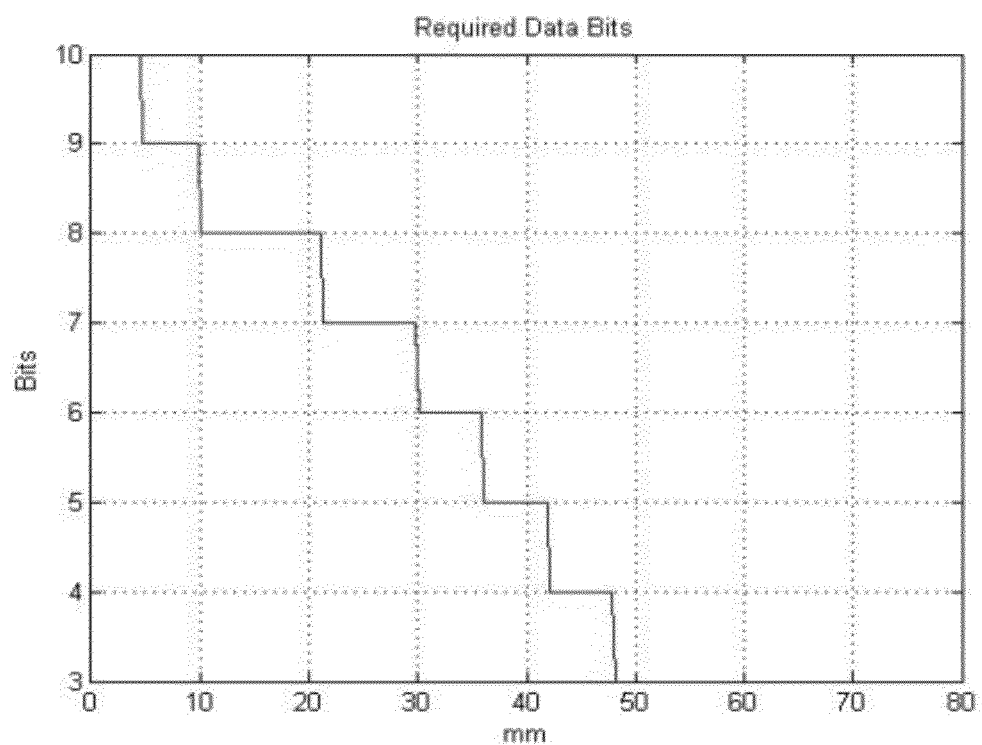
FIG. 17 is a graphical depiction of the number of bits of data required over a depth range of 0 to 80 mm for the parameters discussed with reference to FIG. 16.

FIG. 17 is a graphical depiction of the number of bits of data required over a depth range of 0 to 80 mm for the parameters discussed with reference to FIG. 16. As shown in FIG. 17, in this example, the number of required bits decreases monotonically with depth. Of course, this graph does not represent all imaging conditions, and the signal levels may peak higher at a point beyond the shallowest depth. For example, signal levels may peak higher at a point beyond the shallowest depth in a focused transmit beam context. Also, in some embodiments, signals that fall below 0 dB may be clipped. In addition, any signals reaching above a range allowed by the number of data bits provided may be clipped to the maximum attainable level, in some embodiments.

With respect to lateral resolution, a total number of data bits transferred from the probe to the main unit or other device may depend on the bit width provided (B), the number of receive channels per transmit (R), and the number of transmit events (T). Both I & Q components may also be represented, and may add another factor of two. The resulting calculation is as follows: Total Bits=2×B×T×R.

In some embodiments, the aperture growth (or the number of transducer elements used) may be varied based on the transmit and receive acceptance angles. As a result, in some embodiments, not all the near-field data may be required for each transmission. Also, in some embodiments, for each transmit event data from receive channels extending beyond the sum of the transmit and receive apertures may not need to be sent to the main unit, because they are outside the aperture bounds. Therefore, data may be reduced in these embodiments because some of the larger bit-width near-field data need not be sent to the main unit.

Also, some embodiments may limit the maximum aperture size and reduce the amount of data sent from the probe to the main unit. Because lateral resolution typically is proportional to aperture size, some embodiments may reduce lateral resolution to permit greater data bandwidth. This may be accomplished, for example, by restricting the maximum aperture size and/or the acceptance angle.

Figure 18:
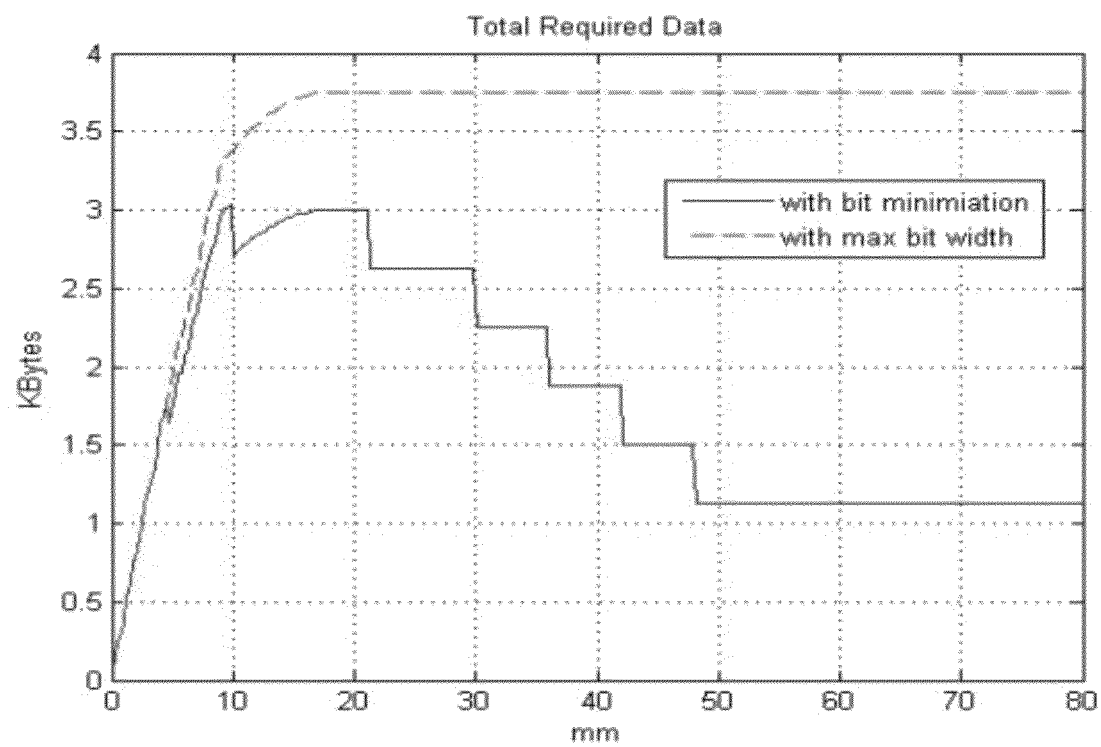
FIG. 18 is a graphical depiction of a total amount of data required from a probe to a main unit with respect to depth of the acceptance angle and edge effects.

FIG. 18 is a graphical depiction of the total amount of data required from the probe to the main unit with respect to depth, considering the acceptance angle and edge effects. When transmitting at or near the edges of the transducer array, the receive aperture may be truncated. As a result, in some embodiments, less data may be sent from the probe to the main unit relating to edge element transmissions. FIG. 18 illustrates the sum of the transmit and receive channels for an entire image frame. As shown in FIG. 18, the dashed line represents the total data assuming the maximum number of bits (10), while the solid line incorporates the bit width optimization as discussed with reference to FIG. 17.

FIG. 18 illustrates that with no savings from aperture reduction, there would be a required 3.75 Kbytes over the full depth range. The aperture restrictions results in a 7% reduction in data, while the bit width minimization results in a 49% reduction of the aperture-restricted data and a total reduction of 52% compared to the non-reduced data. In terms of transmitted frames per second (fps), the maximum achievable frame rate with no data reduction is 37 fps, while with data reduction a frame rate of 78 fps is achievable.

A region of interest (ROI) of an imaging system may refer to a geometric dimension represented by the displayed image. For example, for a linear array, an image's width typically extends to the edges of the array but, in some embodiments, may be steered to go beyond the edges. For example, with phased array systems, beams may be steered such that the beam vectors converge at a relatively common apex. In some embodiments, a maximum steering angle may be dependent on probe frequency and element pitch.

With respect to B-mode imaging, for example, an image may be formed from a linear array probe with little or no steering. The depth range of the image may be considered to be the distance between the shallowest image point and the deepest, for example. Signal acquisition time may be proportional to the depth range, and the depth range may be a determining factor in a number of data samples that are transferred from the probe to the main unit. In some embodiments, in order to minimize data, it may not be required to transfer data that does not contribute to the formation of image pixels. Therefore, data acquired either before a minimum required sample time and/or after a maximum required time may not need to be transferred to the system in some embodiments.

In some embodiments, factors that may be considered in signal acquisition time may include consideration of path lengths. For example, signal acquisition time may be based upon an echo path length of the closest element to the minimum depth point (path_min), and/or an echo path length of the furthest element to the maximum depth point (path_max). These path lengths may depend on a number of various factors including steering angle, aperture size, and/or aperture growth rate, for example.

A maximum acquisition time may be proportional to a difference between the shortest and longest echo path lengths (i.e., path_max−path_min). In some embodiments, the data sample range transferred from the probe to the main unit may be constrained to this time period so as to provide optimal wireless bandwidth conservation, for example.

Figure 19:
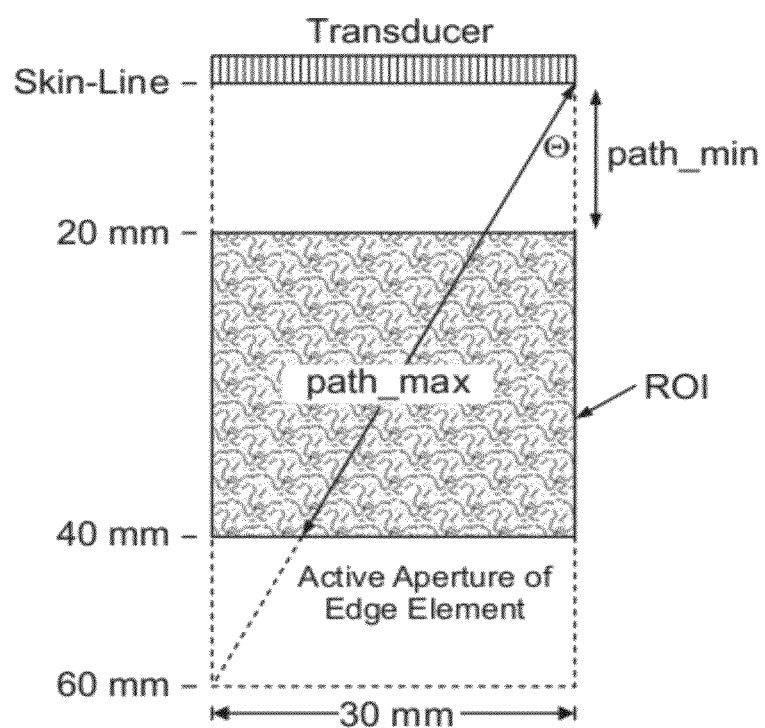
FIG. 19 is an illustration of an example image region of interest for a linear array transducer.

FIG. 19 is an illustration of an example image ROI for a linear array transducer with a 30 mm width. The values defined with reference to FIG. 19 provide just one example for the purpose of clarity and brevity and are not meant to be exclusive values. In some embodiments the minimum path length (path_min) is the distance of the perpendicular line from the transducer to the shallowest image ROI point of 20 mm, and the maximum path length (path_max) is the distance from an edge element to the furthest image ROI point from it. As shown in FIG. 19, the f-number is set to 1.0 so the aperture may not be completely on at the ROI bottom depth of 40 mm. While there may be a dependence on aperture growth it may be to a substantially lesser degree.

The acceptance angle ($\Theta$) is equal to $\tan^{-1}(30/60)=26.56°$, and the path_max distance is $40/\cos(\Theta)=44.72$ mm. Therefore, the maximum acquisition time is as follows: acquisition_time=1.3(path_max−path_min)=1.3(44.72−20)=32.1 µs, where 1.3 is the roundtrip travel time of sound in µs/mm. If the ROI is extended to the skin-line or surface of the medium, an acquisition time may be 1.3×44.72=58.1 µs. As a result, in some embodiments, with either starting depth, the elements have a same minimum path length, but with perhaps different maximum path lengths. For example, when transmitting at the center element location, the path_max value from the skin-line may be $\sqrt{15^2+40^2}=42.7$ mm, giving an acquisition time of 1.3×42.7=55.5 µs, or 4.5% less than the edge element time.

Therefore, it may be desirable in some embodiments to specify individual acquisition times for each transmit/receive transducer element combination, perhaps to minimize an amount of data to be transferred between the probe to the main unit or other device.

Communication bandwidth may place an upper limit on axial resolution, because the displayed resolution may be determined by various parameters including transducer characteristics and the display device. For example, it is well understood by those skilled in the art that the Nyquist criterion prescribes that a desirable resolution may be attained by adequately sampling a received echo signal by at least twice its bandwidth. For example, with quadrature sampling using in-phase and quadrature components, each component may be sampled at a rate equal to or greater than the signal bandwidth. Bandpass sampling techniques may produce a quadrature baseband signal from each receiver channel that is ideally sampled at a rate adequate to capture the information content provided by the transducer bandwidth. Therefore, in some embodiments, producing data at this rate is relatively efficient because it produces a minimum amount of data necessary to avoid loss of image quality. Other embodiments may use over-sampling techniques to provide benefits like greater SNR, at the expense of producing more data than perhaps needed. Therefore, in just some embodiments, in order to minimize data required to be transferred from the probe to the main unit, the probe may transfer baseband data sampled at less than or equal to the ideal sampling rate based on the transducer's bandwidth.

The baseband representation of the data signal may retain the full signal bandwidth with the energy centered perhaps around zero frequency (DC) instead of Fc. The baseband signal may be considered in analytic form as I+j*Q where I is the in-phase component and Q is the quadrature component. It should be appreciated that the baseband signal may be derived by quadrature demodulation of the data signal. This may be accomplished, for example, using a complex mixer followed by a low-pass filter on the I and Q components.

In those embodiments where baseband conversion is performed prior to analog-to-digital conversion, the analog-to-digital converter sampling rate may be less than that required to capture the data signal information. For example, for a data signal with 100% bandwidth, the sampling rate may be at least 3 times Fc (e.g., to satisfy the Nyquist criterion). In some embodiments, baseband signal may need to be sampled at Fc for each of the analytic components for a combined sampling rate of 2 times Fc. Therefore, the sampled data may produce 50% more data samples than baseband sampled data. It should be appreciated that the increase may be greater yet for smaller probe bandwidths.

Some embodiments may provide baseband conversion using a quadrature sampling, well known to those skilled in the art. For example, quadrature sampling may be conducted by sampling the data signal at 4 times Fc followed by decimation of the other pair of samples. In this example, remaining sample pairs may approximately represent I and Q baseband sample pairs. Although this embodiment, known in the art as second-order sampling, may be simplistic it also may reduce an amount hardware and software complexity, which may be desirable in some embodiments. Also, in some embodiments using second-order sampling, component (e.g., probe) complexity and circuitry may be minimized via multiplexing techniques, like time and frequency techniques. For example, two receiver channels may be multiplexed into a single analog-to-digital converter on alternate pairs of I and Q samples. Via multiplexing techniques the data may be arranged, interleaved and/or multiplexed using a number of techniques. Some of the multiplexing techniques may serve to reduce data bandwidth as well as serve other objectives. For example, data may be manipulated after converting the received echoed ultrasound wave to digital data and/or data may be manipulated to converting the received echoed ultrasound wave to digital data. The multiplexing techniques may include time-division multiplexing, frequency-division multiplexing, code-division multiplexing, and/or pulse width-division multiplexing. The data also may be interleaved as a function of time, position of transducer channels, and/or data bit position.

Interpolation may be used to overcome some inherent time misalignment of I and Q components. In some embodiments, such sample interpolation may be used in combination with other sample interpolation techniques, like coherence preservation techniques.

Third-order sampling techniques also may be used to improve the time alignment of I and Q sample pairs. For example, this third-order sampling technique may be implemented by subtracting the 180° phase sample from the 0° phase sample and dividing the result by 2 to form the in-phase component. The quadrature component may be acquired as the 90° phase sample just as in second-order sampling.

Some embodiments may maintain greater axial resolution with relatively low drive voltages. This may be accomplished using a number of techniques, including for example, coded transmitted excitations that use a relatively large time-bandwidth product codes. In order to ensure greater axial resolution under relatively basic excitation conditions, an acoustic pulse provided by the transmitting transducer may be an impulse response. In those embodiments that employ coded excitation techniques, the acoustic pulse may be relatively longer than the transducer's typical impulse response. For example, coded excitation may transmit a long "chirp" or sequences of orthogonal signals, known by those skilled in the art as Golay codes. The received echoes may be correlated with a reference waveform to regain axial resolution of a short pulse, for example. A relatively longer pulse provided by coded excitation may increase signal-to-noise ratio that may otherwise be sacrificed due to other factors (e.g., general synthetic transmit focus techniques).

In some embodiments, transducer bandwidth may not be matched to a final display resolution. For example, a single transducer element sampled using bandpass sampling with a center frequency (Fc) of 6 MHz, may have a bandpass sampling rate of approximately 6 MHz. In some embodiments it may be that this sampling rate would be adequate if the signal energy was negligible at frequencies lower than 3 and greater than 9 MHz, for example. Also, the 6 MHz rate with an image ROI from the skin-line to 40 mm may yield a worst-case number of samples of 58.1×6=349 samples, where the 58.1 μs was derived in the above ROI example. In some embodiments, this may be reduced by, for example, applying different acquisition times to the various element combinations and/or to each transmit location.

In this example, while it may be necessary to acquire and transfer approximately 349 samples per element combination, the vertical dimension of the displayed image may require just 1.3×40×6=312 samples. If, as in some embodiments, the samples can be mapped directly to displayed image pixels, this would require a display pixel density of 312/40=7.8 pixels/mm. In other embodiments, it may be desirable to ensure square pixels, such that the 30 mm wide image may require 234 horizontal columns of pixels. The 349×234 pixel grid may represent a maximum resolution supported by a particular transducer. Of course, depending on the properties of the display, this image may or may not provide a desirable perceptible resolution from a typical viewing distance. Therefore, for displays with very high pixel densities, for example, in some embodiments it may be desirable to scale the image up to larger pixel dimensions. This may be accomplished using various techniques, including for example, interpolation.

If in the example, an image ROI includes a depth range from the skin-line to 80 mm, it may be that twice the number of samples (i.e., 624) may be produced at the same 6 MHz sampling rate. Of course, in some embodiments the displayed image may have a span on the screen that is less than 624 pixels, such that the signal bandwidth may be reduced and the data resampled at a more suitable (e.g., lower) rate. Alternatively, in some embodiments, it may be desirable instead or in addition to trade-off axial resolution for reduced wireless data rates at relatively larger depth ranges in order to maintain higher frame-rates. In either case, typically it may be desirable to perform the data rate reduction early in the system processing to avoid transferring and managing more data than is necessary to attain the desired image resolution. This may be accomplished in some embodiments using a data resampler function following the analog-to-digital converter, for example, for each receiver channel within the probe.

The following example provides just one scenario contemplated by the disclosed embodiments. In just this one example, a 2D ultrasound image display may be composed of a pixel grid with a spacing based on the properties of the display device and the image acquisition parameters. For example, a typical display device may have a maximum pixel resolution of 800×600. The image may be created to fit a portion of this display grid. The imaging distance as a result of the pixel spacing may be determined by a relationship between the data rate (e.g., sampling rate of the data presented to the display) and the speed of sound (e.g., approximately 1540 m/s in a human body, for example). This relationship may be defined as: $D=c\div(2\times R)$, where c is the one-way speed of sound, R is the data rate, and the factor of 2 derives from the roundtrip travel of the pulse. The relationship may be considered in the context of a pulse traveling from a single element in a direction perpendicular to the transducer array. For purposes of this one example, it may be considered that the returning echo signal is converted to baseband, envelope-detected, sampled periodically, and mapped to the display in a direct (i.e., sample-to-pixel) relationship. If the sampling rate (R) is 6 MHz and the image display is composed of a column of 300 pixels, the representative image depth range would be: 300×1540÷(2×6)=38.5 mm.

In those embodiments where it may be desirable to display twice that depth range, it can be seen from this relationship that either twice the number of samples may be acquired corresponding to twice the number of pixels, and/or the sampling rate may be reduced by a factor of 2.

In some embodiments the relationship between the sampling rate and signal bandwidth may be manipulated. As is well known to those skilled in the art, sampling theory designates the signal sampling rate to be at least twice the signal bandwidth (i.e., Nyquist rate). In some embodiments, this may avoid corrupting the resultant signal by a phenomenon well known to those skilled in the art as aliasing. For example, in some embodiments where the signal of interest is represented as a quadrature pair of signal components, the sampling rate of each quadrature component may be equal to or greater than the bandwidth represented by the component pair. Therefore, some embodiments may include a relationship between transducer bandwidth and display resolution.

In some embodiments it may be that the signal may be sampled at a different rate than the Nyquist rate, for example, unless the quadrature signal bandwidth is confined to that rate. For example, although it may be sufficient to sample at a rate higher than the transducer bandwidth and display the full signal resolution for even the deepest desired depth range, it should be appreciated that in some embodiments, this may be impacted by the resolution of the display device. For example, in some embodiments the display may be able to display less than a required number of pixels for full resolution imaging. It some embodiments, it may be desirable to reduce some resolution if larger depth range is desired, for example, by filtering the signal to a desired bandwidth and/or resampling the signal to a desired rate. In some embodiments such resampling may occur within the main unit (e.g., after the beamformer), the probe and/or some other device.

Resampling typically is a linear process, such that output samples may be formed as linear combinations of neighboring input samples through a filtering process. Also, it may be that beamforming is linear, because it may include linear combinations of a set of time-delayed signals. It should be appreciated in these embodiments that superposition may hold for linear systems, such that resampling each data sequence prior to beamforming, for example, may be analogous to resampling after. In some embodiments, it may be desirable to perform resampling as early as possible in the processing.

Data resampling may be limited to rational numbers (e.g., P/Q). Resampling to a rate of P/Q may be accomplished by first up-sampling by a factor of P by zero-padding the data sequence with P-1 zeros. A zero-padded sequence (XP) is shown as follows for P=4:

$X = X_1 X_2 X_3 X_4 X_5 X_6$ $XP = X_1\ 0\ 0\ 0\ X_2\ 0\ 0\ 0\ X_3\ 0\ 0\ 0\ X_4\ 0\ 0\ 0\ X_5\ 0\ 0\ 0\ X_6\ 0\ 0\ 0$

In some embodiments, a zero-padded sequence may be filtered with a finite-impulse response (FIR) filter, for example. The filter characteristics may be chosen as a function of desired data bandwidth and/or resampling factors. The sequence XPF below represents the XP sequence described above with the zero samples altered due to the filter. In some embodiments, it should be appreciated that the original signal samples may or may not be altered by the filter, although shown here as unaltered.

$XPF = X_1 X_{11} X_{12} X_{13} X_2 X_{21} X_{22} X_{23} X_3 X_{31} X_{32} X_{33} X_4 X_{41} X_{42} X_{43}$

In some embodiments, the filtered sequence may be decimated in various ways, including for example, by discarding Q-1 samples after a retained sample, resulting in the final desired data rate. The decimated sequence is shown, in just one example, for Q=3 and the resulting rate of 4/3 the original data rate.

$XPFD = X_1 X_{13} X_{22} X_{31} X_4 X_{43} X_{52} X_{61}$

For color flow data acquisition, front-end gains may be set at a maximum throughout most of a field of view. In some embodiments, for example, such a value may provide optimum sensitivity of red blood cell echo waves. Also, some signal saturation around strong reflectors may be acceptable, for example, where some arbitration may be provided to reject artifacts. With color flow techniques, the data signal may carry both tissue-level echoes or clutter, and blood echoes. For example, in some embodiments, clutter-to-signal ratio (CSR) may be approximately 60 dB. In some embodiments, the clutter filter may reduce dynamic range.

Some embodiments may reduce color flow data via clutter filtering, for example, prior to wireless data transfer from the probe. This may be performed, for example, with beamformed, non-beamformed, and other types of data. Color flow clutter filters may include high-pass filter characteristics. For example, color flow clutter filters may be implemented with a finite impulse response (FIR). Such embodiments may minimize filter settling time, because color flow usually operates with relatively short data ensembles.

An example filter may be a single DC canceller characterized as $Y(n)=X(n)-X(n-1)$, where $X(n)$ is the input signal at time "n" and $Y(n)$ is the filtered output. Such a filter may provide a single zero at DC and a slow roll-off, high-pass frequency response, well known to those skilled in the art. Some embodiments may use such an approach because of its ease of implementation, need for just a single storage state, and just one settling pulse.

Other embodiments may use a similar design that provides two zeros at DC, called a double canceller, and implemented as $Y(n)=X(n)-2\times(n-1)+X(n-2)$, where $X(n)$ is the input signal at time "n" and $Y(n)$ is the filtered output. The double canceller filter may provide greater low frequency clutter attenuation and greater transient rejection. Also, some embodiments may implement color flow in a continuous acquisition so as to allow the use of filters with significantly longer settling times. In these embodiments, a first-order IIR filter may be used described as $(1-\alpha)Y(n)=X(n)-X(n-1)+\alpha Y(n-1)$, where $X(n)$ is the input signal at time "n" and $Y(n)$ is the filtered output. This filter may provide a sharper response than either FIR filter, but with similar computational complexity and storage requirements as the double canceller.

In some embodiments, quantization may be more difficult to manage with IIR type filters. In some embodiments, an IIR with two zeros at DC may provide greater transient cancellation. The length of the transient and steepness of the cutoff may be proportional to a (i.e., larger a requires longer settling but provides steepest roll-off).

It should be appreciated that the discussion of filters is not limited and many other filters may be used, some with greater hardware complexity and storage requirements. Also, some embodiments may implement just a part of the overall clutter filter in the probe to provide most of the attenuation required to reduce the signal dynamic range, while performing any remaining filtering in the main unit. Any combination thereof is contemplated by the disclosed embodiments.

Embodiments that use continuous acquisition may reduce or eliminate usual limitations on clutter filtering, well known to those skilled in the art. For example, filters may be designed specifically for transient suppression. For continuous acquisition color flow, greater design freedom is recognized and may allow for a variety of different filter design methodologies.

In some embodiments, data collection methods may vary. For example, one method that may be used is to gather a single frame of data sequentially as quickly as possible to minimize phase errors across the frame. Also, in some embodiments, it may be desirable to continue data collection regardless of interruptions in the data transfer, while in other embodiments it may be desirable to cease data collection.

One way to manage data flow from the data collection process to the data transmission process may be to use a "ping-pong" buffer (e.g., two frames deep) to store entire frames of data. A ping-pong buffer may be implemented using a variety of standard random access memory (RAM) storage devices, for example. One alternative to a ping-pong buffer may be a first-in-first-out (FIFO) storage device, for example. In the case of a ping-pong buffer, the data collection process may continue at a maximum rate until a full frame is acquired. If the data transmission process is slower than the data collection process, the data collection may fill the second frame buffer before the first is emptied. In this case, data collection may be stopped after completing that frame, and may wait until one of the frames of the ping-pong buffer is emptied (e.g., transmitted), such that it is ready to accept an entire frame of new data, for example, gathered at the maximum rate set by the collection process.

Figure 21:
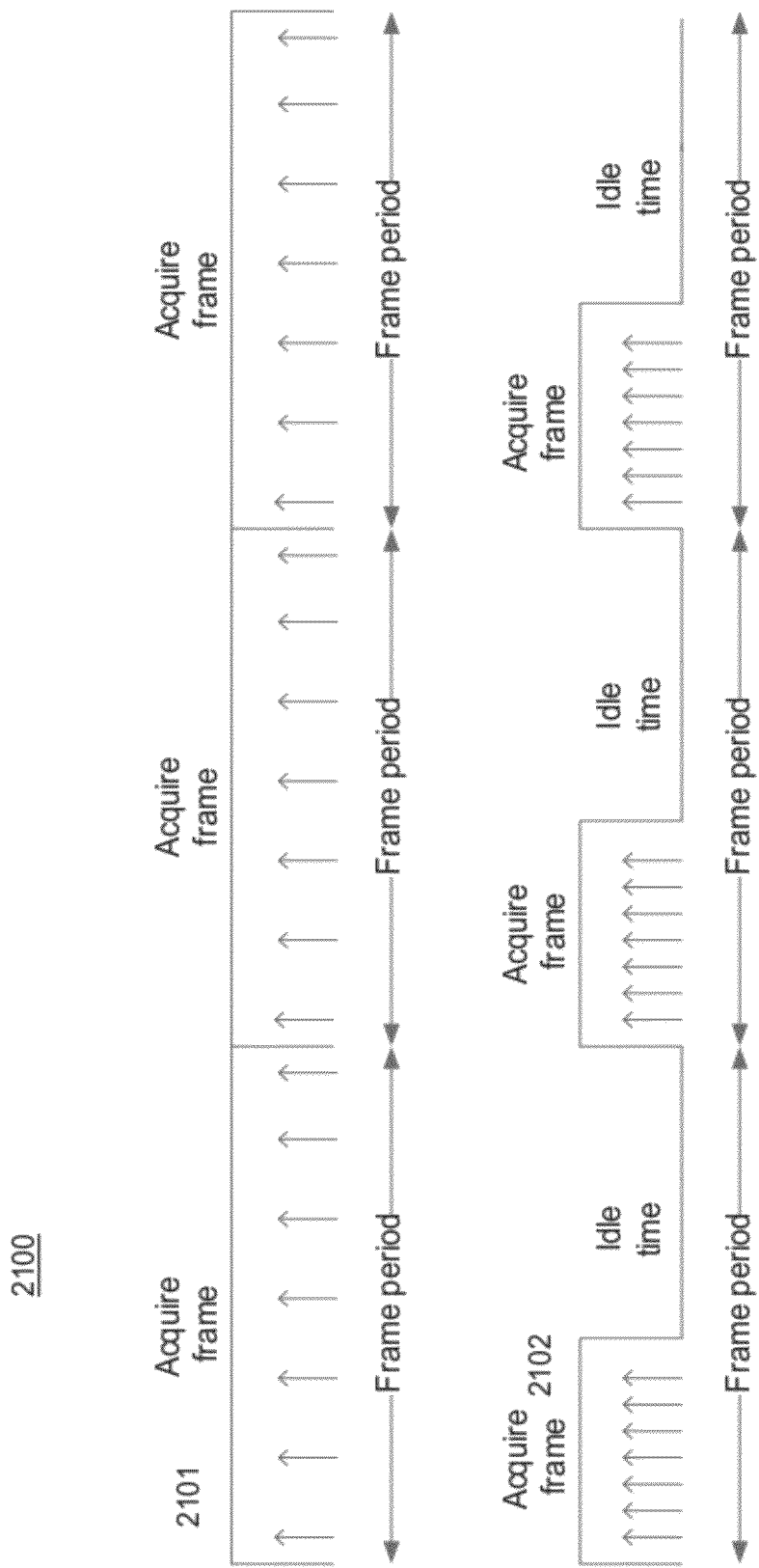
FIG. 21 is a timing diagram illustrating the acquisition of frames of data.

FIG. 21 is a timing diagram 2100 illustrating the acquisition of frames of data, using two methods 2101 and 2102. In method 2101, acquisition may be spread out over a frame period with each transmission period evenly divided over the available frame time. In method 2102, time between transmissions may be shortened so that the frame acquisition may occur in a compressed time period, while the average data rate over a frame period may be the same or substantially similar to method 2101. Method 2102 is allowed by frame buffer.

In some embodiments, where bandwidth restricts a frame rate by a factor of two or more, for example, it may be advantageous to acquire multiple data sets and combine the data within the probe, and/or some other device, before transmission to the main unit. This coherent combination may provide improved signal-to-noise ratio and/or some other image enhancement.

In some embodiments, the communication medium or link may not provide consistent bandwidth. In these embodiments, it may be desirable to adaptively adjust data acquisition parameters in response to the available bandwidth. These parameters may include, but are not limited to, acquisition frame rate, transmit aperture size, receive aperture size, and/or sparsity of transmit and/or receive apertures.

Figure 20:
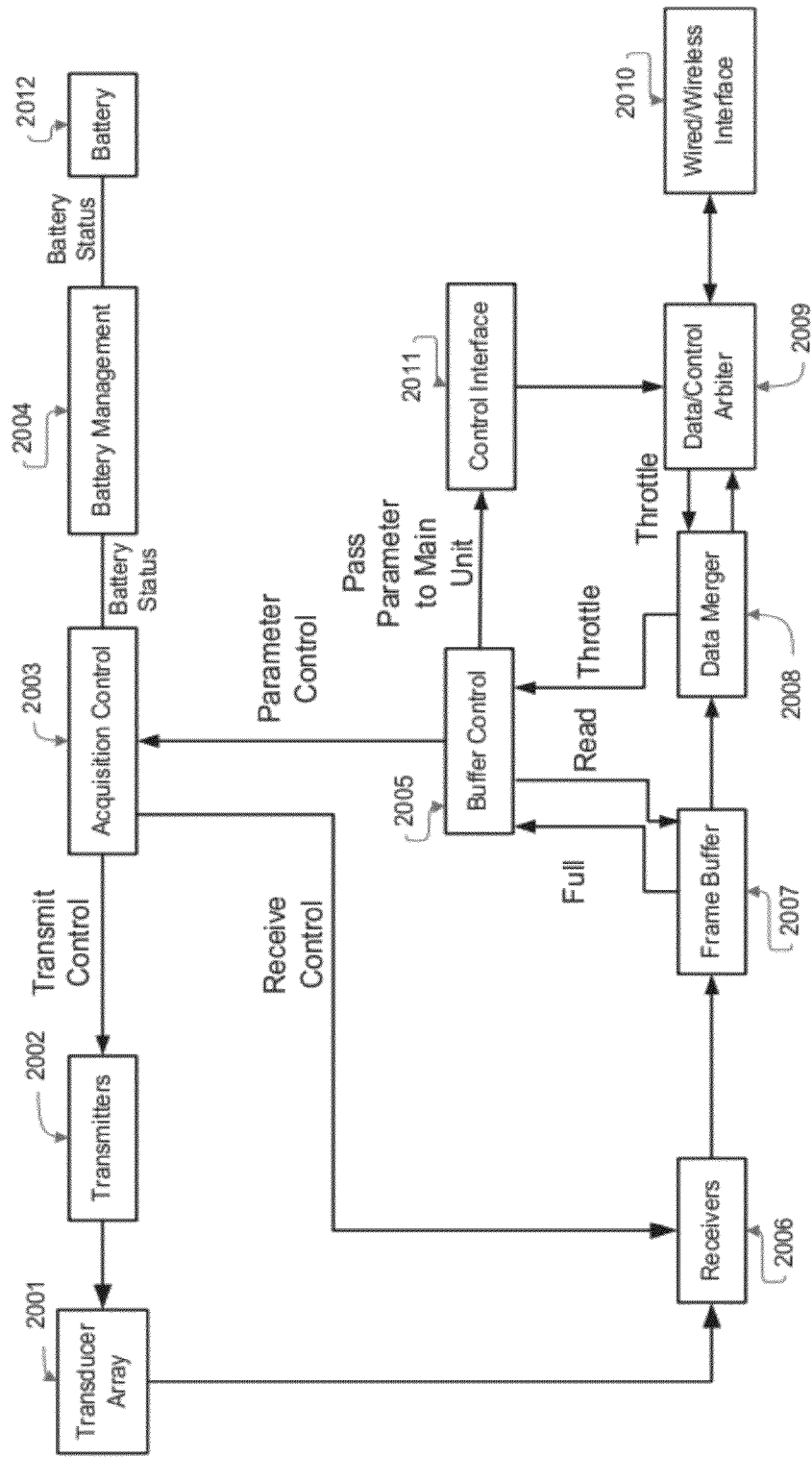
FIG. 20 is a block diagram employing a ping-pong frame buffer.

In addition, coherent combination for improved signal-to-noise ratio may be dynamically controlled in response to the available bandwidth. FIG. 20 provides a block diagram to provide such dynamic control using a ping-pong frame buffer.

With any wired and/or wireless link there exists a possibility of interference that may cause the communication link to be lost, at least temporarily. One way to accommodate and prevent such loss of data is through packetization techniques so as to allow data to be recovered from a temporary loss of signal by re-transmitting the lost data packets. While the data is eventually re-transmitted successfully, it may increase the amount of data transfer and the rate at which it is transferred.

In those embodiments that use acoustic transmit focus techniques, it may be that an entire frame of data is captured sequentially as fast as possible to minimize phase errors across the frame. In these embodiments, it may be undesirable to stop the data collection process in response to interruptions in the data transfer. One possible solution contemplated by the disclosed embodiments is to use a ping-pong buffer (also known as a double buffer) for entire frames of data. In this way, the data collection process may continue at a maximum rate until a full frame is acquired. If the data transmission process becomes slower than the data collection process, the data collection may, at some point, fill the second frame buffer before the first is emptied. In this case, data collection may be stopped after filling the second frame, and may wait until one of the frames of the ping-pong buffer is emptied (e.g., transmitted), and is ready to accept an entire frame of new data, gathered at the maximum rate set by the collection process. Of course, other alternatives are contemplated by the disclosed embodiments, including using a larger ping-pong buffer and/or using memory from other parts of the system. Also, instead or in addition to the ping-pong buffer, a first-in-first-out (FIFO) memory device may be used that is large enough to accommodate two entire frames, and with a means of detecting when there is enough room in the FIFO to hold an entire frame of data.

Figure 22:
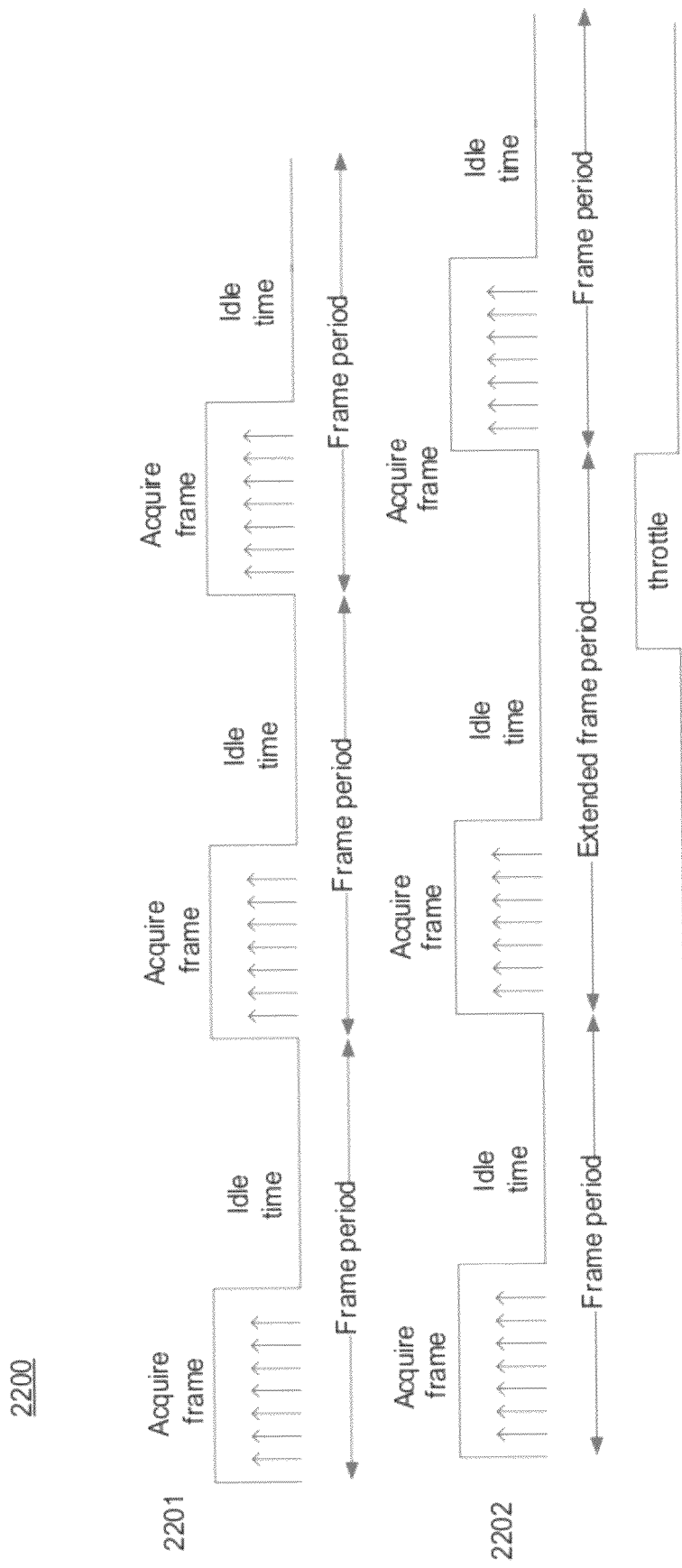
FIG. 22 is a timing diagram illustrating this frame adjustment.

Referring to FIG. 20, a feedback loop 2000 may be used to implement such methods. As shown in FIG. 20, a throttle signal shown on the diagram may instruct the data merger 2008 and buffer control 2005 as to when the wireless interface 2010 can and cannot accept data. The wireless interface 2010 may communicate with the data merger 2008 through data/control arbiter 2009. For example, if the throttle prevents a frame of data from being transmitted at its maximum possible rate (i.e., the acquisition rate), the buffer control 2005 may inform acquisition control 2003 to adjust its frame acquisition period accordingly. The buffer control 2005 may receive a full indication from the frame buffer 2007 and may instruct the frame buffer 2007 to read. The buffer control 2005 may communicate parameters to the control interface 2011. The acquisition control 2003 may receive a battery status from battery management 2004 which may be in communication with battery 2012. The acquisition control 2003 may also communicates transmit control to transmitters 2002, which may communicate to the transducer array 2001. The acquisition control 2003 may also communicate receive control to the receivers 2006. FIG. 22 is a timing diagram 2200 illustrating this frame adjustment, where two different timing cycle examples 2201 and 2202 are depicted.

FIG. 23 is a chart representing a sequence of writes and reads to a ping-pong frame buffer for a frame of 5 samples, for example. As shown in FIG. 23, at time units 1 through 5, the 5 frame samples are written to frame buffer addresses 1a through 5a, substantially consecutively. Similarly, at time units 6 through 10, the next 5 frame samples are written to frame buffer addresses 1b through 5b, where a and b represent the two pages of the ping-pong buffer. Once the first full frame of data has been written to the buffer, reading of the buffer may commence as indicated at time unit 6. In this example, the first frame requires twice as long to read out than to write with each address persisting for 2 time units. During time units 11 through 15, the write side of the buffer is throttled (as indicated by the letter T) while waiting for the first frame to be completely read out. At time units 16 through 20, the third acquired frame is written to addresses 1a through 5a. The read out of the second acquired frame begins at time unit 16 immediately after the read out of the first acquired frame. Starting with the forth sample, the addresses persist for 4 time units instead of 2 indicating, perhaps, a decrease in the data transmission rate. The throttle condition exists for time units 21 through 29, 4 units longer than the previous throttle period. Entire frames of data may be written in just 5 consecutive time units indicating that data acquisition may be confined to a 5 time unit interval even though the acquisition frame period is longer and variable.

In some embodiments, acquisition control may be instructed to change other acquisition parameters. For example, with respect to synthetic receive aperture imaging, multiple transmissions may be required to collect a receive aperture. In response to the throttle signal, acquisition control may be made to reduce the receive aperture size and, therefore, fire fewer transmissions so as to reduce an amount of data necessary to send to the main unit and/or some other device.

In these embodiments, the main unit or the other device may require some information regarding the receive aperture size reduction for its beamformation and/or pixelformation processing, for example. Therefore, this information may be included in a control data sent along with the acquired image data, for example. It should be appreciated that various other acquisition parameters may be adjusted to achieve the same effect, and are contemplated by the disclosed embodiments.

While the embodiments have been described in connection with various embodiments of the various figures, it is to be understood that other similar embodiments may be used or modifications and additions may be made to the described embodiment for performing the same function of the disclosed embodiments without deviating therefrom. Therefore, the disclosed embodiments should not be limited to any single embodiment, but rather should be construed in breadth and scope in accordance with the appended claims.

What is claimed is:

1. A method for conducting ultrasound interrogation of a medium, comprising:
    receiving an ultrasound echo wave at a first transducer element of a transducer array in a handheld probe of an ultrasound system;
    receiving the ultrasound echo wave at a second transducer element of the transducer array in the handheld probe of the ultrasound system;
    receiving the ultrasound echo wave at a third transducer element of the transducer array in the handheld probe of the ultrasound system;
    converting the received ultrasound echo waves into digital data;
    processing into digital data the ultrasound echo wave received at the first transducer element and the ultrasound echo wave received at the second transducer element, the processing precluding data representative of the ultrasound echo wave received at the third transducer element from being included in the digital data, and the processing including reducing the digital data without beamforming data representative of the ultrasound echo wave received at the first transducer element with data representative of the ultrasound echo wave received at the second transducer element; and
    transmitting the digital data to a location relatively remote from the handheld probe.

2. The method of claim 1, wherein the reducing the digital data comprises restricting the digital data to an area in a region of interest.

3. The method of claim 1, wherein the reducing the digital data comprises resampling from a first sampling rate to a second sampling rate, the second sampling rate being lower than the first sampling rate.

4. The method of claim 1, wherein the reducing the digital data comprises clutter filtering.

5. The method of claim 1, wherein the reducing the digital data varies with a distance traveled by the ultrasound echo wave.

6. The method of claim 1, wherein the reducing the digital data is based on an amplitude of the ultrasound echo wave.

7. The method of claim 1, wherein the reducing the digital data comprises a mapping from a first data value to a second data value.

8. The method of claim 7, wherein the second data value has fewer bits than the first data value.

9. The method of claim 7, wherein the mapping varies across a data frame.

10. The method of claim 1, wherein the reducing the digital data is based on achieving a target dynamic range.

11. The method of claim 1, wherein the reducing the digital data reduces a quality of an image formed from the digital data.

12. The method of claim 1, wherein the reducing the digital data substantially maintains a quality of an image formed from the digital data.

13. The method of claim 1, wherein the reducing the digital data is based on a rate of transmission of the digital data.

14. The method of claim 1, wherein the reducing the digital data comprises translating the ultrasound echo wave to baseband data.

15. The method of claim 1, wherein the reducing the digital data comprises at least one of the following: filtering, quantization, frequency translation, data compression, clipping, dynamic range transfer, or domain transform.

16. A device for conducting ultrasound interrogation of a medium, the device being a handheld probe of an ultrasound system, the device comprising:
    a transducer array, the transducer array configured, at least in part, to:
        receive an ultrasound echo wave at a first transducer element of the transducer array;
        receive the ultrasound echo wave at a second transducer element of the transducer array; and
        receive the ultrasound echo wave at a third transducer element of the transducer array;
    a converter to convert the received ultrasound echoes into digital data;
    a processor, the processor configured, at least in part, to:
        process into digital data the ultrasound echo wave received at the first transducer element and the ultrasound echo wave received at the second transducer element, the processing precluding data representative of the ultrasound echo wave received at the third transducer element from being included in the digital data, and the processing including reducing the digital data without beamforming data representative of the ultrasound echo wave received at the first transducer element with data representative of the ultrasound echo wave received at the second transducer element; and
    a transmitter, the transmitter configured, at least in part, to:
        transmit the digital data to a location relatively remote from the handheld probe.

17. The device of claim 16, wherein the processor is further configured such that the reducing the digital data comprises restricting the digital data to an area in a region of interest.

18. The device of claim 16, wherein the processor is further configured such that the reducing the digital data comprises resampling from a first sampling rate to a second sampling rate, the second sampling rate being lower than the first sampling rate.

19. The device of claim 16, wherein the processor is further configured such that the reducing the digital data comprises clutter filtering.

20. The device of claim 16, wherein the processor is further configured such that the reducing the digital data varies with a distance traveled by the ultrasound echo wave.

21. The device of claim 16, wherein the processor is further configured such that the reducing the digital data is based on an amplitude of the ultrasound echo wave.

22. The device of claim 16, wherein the processor is further configured such that the reducing the digital data comprises a mapping from a first data value to a second data value.

23. The device of claim 22, wherein the processor is further configured such that the second data value has fewer bits than the first data value.

24. The device of claim 22, wherein the processor is further configured such that the mapping varies across a data frame.

25. The device of claim 16, wherein the processor is further configured such that the reducing the digital data is based on achieving a target dynamic range.

26. The device of claim 16, wherein the processor is further configured such that the reducing the digital data reduces a quality of an image formed from the digital data.

27. The device of claim 16, wherein the processor is further configured such that the reducing the digital data substantially maintains a quality of an image formed from the digital data.

28. The device of claim 16, wherein the processor is further configured such that the reducing the digital data is based on a rate of transmission of the digital data.

29. The device of claim 16, wherein the processor is further configured such that the reducing the digital data comprises translating the ultrasound echo wave to baseband data.

30. The device of claim 16, wherein the processor is further configured such that the reducing the digital data comprises at least one of the following: filtering, quantization, frequency translation, data compression, clipping, dynamic range transfer, or domain transform.

* * * * *